(12) United States Patent
Heller et al.

(10) Patent No.: US 9,157,064 B2
(45) Date of Patent: Oct. 13, 2015

(54) METHODS FOR GENERATING INNER EAR CELLS IN VITRO

(75) Inventors: Stefan Heller, Stanford, CA (US); Mohammad Ronaghi, Stanford, CA (US); Kazuo Oshima, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 44 days.

(21) Appl. No.: 13/980,837

(22) PCT Filed: Jan. 23, 2012

(86) PCT No.: PCT/US2012/022222
§ 371 (c)(1),
(2), (4) Date: Sep. 23, 2013

(87) PCT Pub. No.: WO2012/103012
PCT Pub. Date: Aug. 2, 2012

(65) Prior Publication Data
US 2014/0004556 A1    Jan. 2, 2014

Related U.S. Application Data

(60) Provisional application No. 61/435,541, filed on Jan. 24, 2011, provisional application No. 61/484,095, filed on May 9, 2011.

(51) Int. Cl.
*C12N 5/0793* (2010.01)
*G01N 33/50* (2006.01)

(52) U.S. Cl.
CPC ............ *C12N 5/062* (2013.01); *G01N 33/5044* (2013.01); *C12N 2501/105* (2013.01); *C12N 2501/115* (2013.01); *C12N 2501/119* (2013.01); *C12N 2501/155* (2013.01); *C12N 2501/727* (2013.01); *C12N 2506/02* (2013.01); *C12N 2506/45* (2013.01); *C12N 2533/52* (2013.01); *C12N 2533/54* (2013.01)

(58) Field of Classification Search
None
See application file for complete search history.

(56) References Cited

U.S. PATENT DOCUMENTS

2005/0287127 A1   12/2005   Li et al.
2008/0267929 A1   10/2008   Li et al.

OTHER PUBLICATIONS

Lefebvre et al. "Retinoic acid stimulates regeneration of mammalian auditory hair cells", Science 260: 692-5, 1993.*
Diensthuber; et al. "Stem/Progenitor Cells Derived from the Cochlear Sensory Epithelium Give Rise to Spheres with Distinct Morphologies and Features", J Assoc Res Otolaryngol (Jun. 2009), 10(2):173-190.
Freter; et al. "Progressive restriction of otic fate: the role of FGF and Wnt in resolving inner ear potential", Development (Oct. 2008), 135(20):3415-3424.
Li; et al. "BMP4 signaling is involved in the generation of inner ear sensory epithelia", BMC Dev Biol (Aug. 2005), 5:16.
Li; et al. "Generation of hair cells by stepwise differentiation of embryonic stem cells", Proc Natl Acad Sci USA (Nov. 2003), 100(23):13495-13500.
Oshima; et al. "Mechanosensitive Hair Cell-like Cells from Embryonic and Induced Pluripotent Stem Cells", Cell (May 2010), 141(4):704-716.
Streit; et al. "The preplacodal region: an ectodermal domain with multipotential progenitors that contribute to sense organs and cranial sensory ganglia", Int J Dev Biol (2007), 51(6-7):447-461.
Zhao; et al. "Sonic hedgehog promotes mouse inner ear progenitor cell proliferation and hair cell generation in vitro", Neuroreport (Feb. 2006), 17(2):121-124, abstract only.
Nishimura et al., "Potential of Pluripotent Stem Cells for the Replacement of Inner Ears" Embryonic Stem Cells—Recent Advances in Pluripotent Stem Cell-Based Regenerative Medicine, pp. 203-210 (Apr. 2011).
Rivolta et al., "Generation of inner ear cell types from embryonic stem cells" Methods in Molecular Biology 330(1):71-92 (Jan. 2006).

* cited by examiner

*Primary Examiner* — Ruth Davis
*Assistant Examiner* — Emily Cordas
(74) *Attorney, Agent, or Firm* — Shweta Chandra; Edward J. Baba; Bozicevic, Field & Francis LLP

(57) ABSTRACT

Methods, compositions and kits are provided for generating inner ear cells in vitro. These methods find use a number of applications, such as in preparing inner ear cells for in vitro screening for agents that are toxic to inner ear cells, for in vitro screening for agents that prevent against, mitigate, or reverse the toxic effects of such agents, and for in vitro screening for agents that promote otoregeneration.

19 Claims, 45 Drawing Sheets

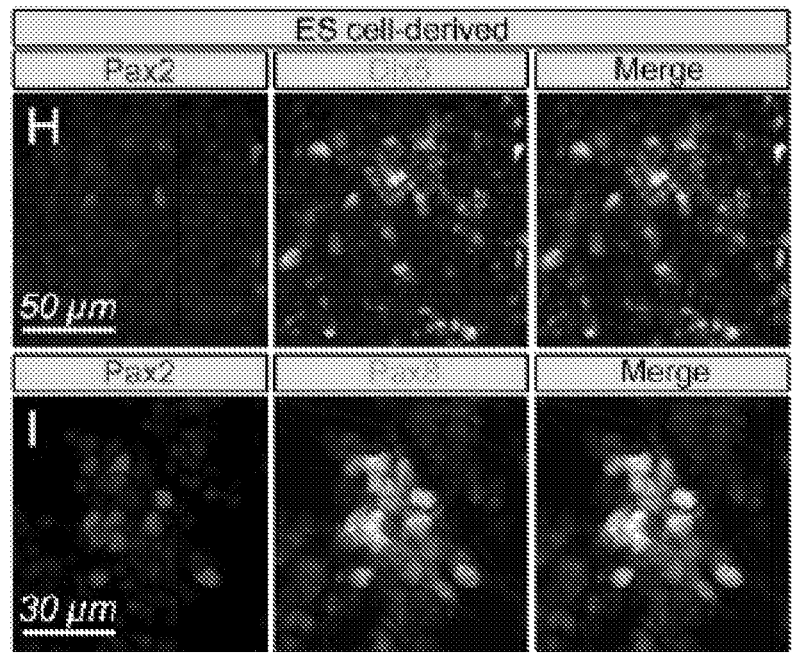
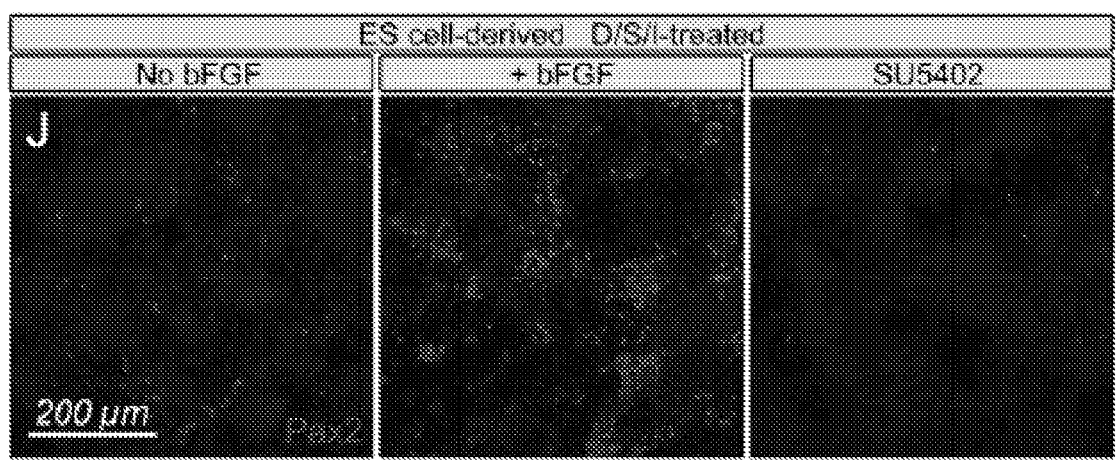
Figure 6H-6J

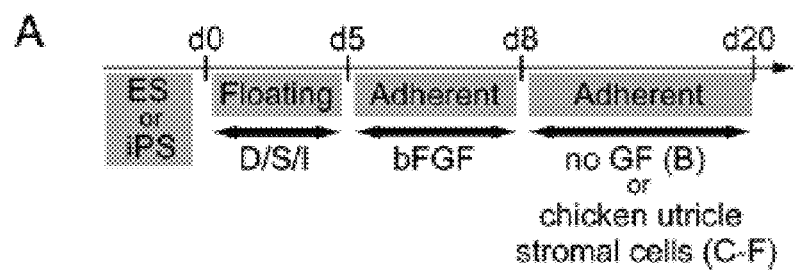
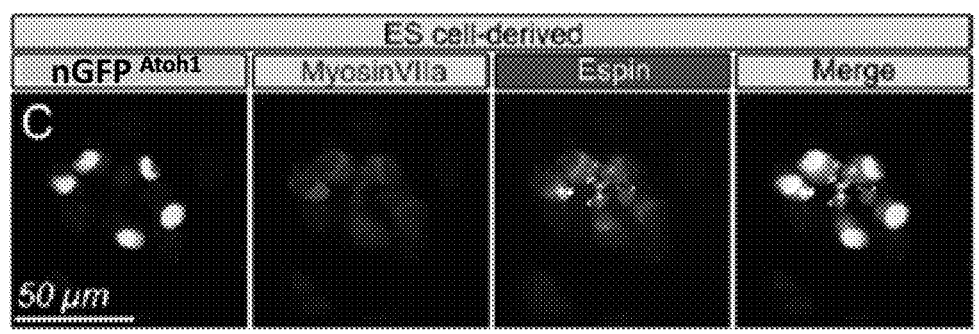
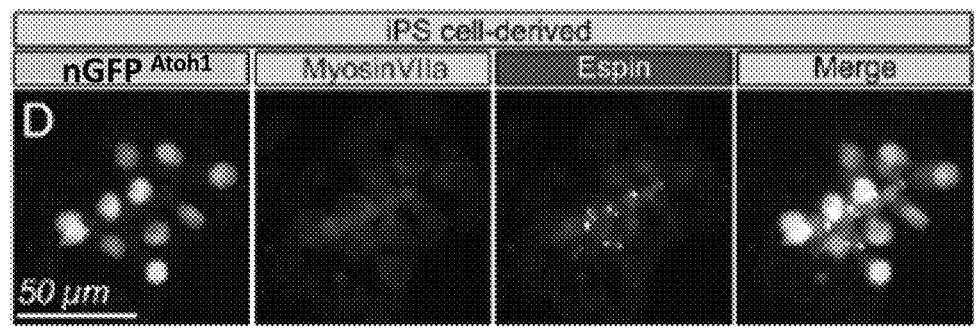
Figure 8A-8D a.

b.

| Number of days cultured with DKK1/SIS3/IGF-1 | Number of days cultured with IGF-1 | % PAX2-expressing cells |
|---|---|---|
| 5 | 3 | 8.3 | c.

| Number of days cultured with DKK1/SIS3/IGF-1 | Number of days cultured with IGF-1 | % PAX2-expressing cells |
|---|---|---|
| 3 | 2-10 | 4.5 |
| 4 | 2-10 | 12.7 |
| 5 | 2-10 | 19.5 |
| 6 | 2-10 | 10.9 |
| 7 | 2-10 | 8.9 |
| 8 | 2-10 | 6.2 |
| 9 | 2-10 | 3.3 |
| 10 | 2-10 | 1.4 |

A.

B.

C.

A.

B.

Human Es Cells (Day 0)  EBs (Day 4)

SEQUENCE LISTING

<160> NUMBER OF SEQ ID NOS: 118

<210> SEQ ID NO 1
<211> LENGTH: 21
<212> TYPE: DNA
<213> ORGANISM: Artificial Sequence

```
<220> FEATURE:
<223> OTHER INFORMATION: Synthetic Oglionucleotide

<400> SEQUENCE: 1
cctccagcag atgcaagaac t                                              21

<210> SEQ ID NO 2
<211> LENGTH: 21
<212> TYPE: DNA
<213> ORGANISM: Artificial Sequence
<220> FEATURE:
<223> OTHER INFORMATION: Synthetic Oglionucleotide

<400> SEQUENCE: 2
agtcctcccc gaagttatgg a                                              21

<210> SEQ ID NO 3
<211> LENGTH: 21
<212> TYPE: DNA
<213> ORGANISM: Artificial Sequence
<220> FEATURE:
<223> OTHER INFORMATION: Synthetic Oglionucleotide

<400> SEQUENCE: 3
atgatggaga cggagctgaa g                                              21

<210> SEQ ID NO 4
<211> LENGTH: 21
<212> TYPE: DNA
<213> ORGANISM: Artificial Sequence
<220> FEATURE:
<223> OTHER INFORMATION: Synthetic Oglionucleotide

<400> SEQUENCE: 4
tccgggaagc gtgtacttat c                                              21

<210> SEQ ID NO 5
<211> LENGTH: 20
<212> TYPE: DNA
<213> ORGANISM: Artificial Sequence
<220> FEATURE:
<223> OTHER INFORMATION: Synthetic Oglionucleotide

<400> SEQUENCE: 5
gtttctgaag tgcccgaagc                                                20

<210> SEQ ID NO 6
<211> LENGTH: 20
<212> TYPE: DNA
<213> ORGANISM: Artificial Sequence
<220> FEATURE:
<223> OTHER INFORMATION: Synthetic Oglionucleotide

<400> SEQUENCE: 6
cagagcagtg acgggaacag                                                20

<210> SEQ ID NO 7
<211> LENGTH: 21
<212> TYPE: DNA
<213> ORGANISM: Artificial Sequence
<220> FEATURE:
<223> OTHER INFORMATION: Synthetic Oglionucleotide

<400> SEQUENCE: 7
tgcctggtca gactgctcat a                                              21
```

<210> SEQ ID NO 8
<211> LENGTH: 21
<212> TYPE: DNA
<213> ORGANISM: Artificial Sequence
<220> FEATURE:
<223> OTHER INFORMATION: Synthetic Oglionucleotide

<400> SEQUENCE: 8
cgaatagcga acctgctaac g                                           21

<210> SEQ ID NO 9
<211> LENGTH: 20
<212> TYPE: DNA
<213> ORGANISM: Artificial Sequence
<220> FEATURE:
<223> OTHER INFORMATION: Synthetic Oglionucleotide

<400> SEQUENCE: 9
atgccaaaga aagaaacgac                                             20

<210> SEQ ID NO 10
<211> LENGTH: 20
<212> TYPE: DNA
<213> ORGANISM: Artificial Sequence
<220> FEATURE:
<223> OTHER INFORMATION: Synthetic Oglionucleotide

<400> SEQUENCE: 10
agaggctgta gaacatgatt                                             20

<210> SEQ ID NO 11
<211> LENGTH: 28
<212> TYPE: DNA
<213> ORGANISM: Artificial Sequence
<220> FEATURE:
<223> OTHER INFORMATION: Synthetic Oglionucleotide

<400> SEQUENCE: 11
accttatggc gtagaaatgc tgagggtg                                    28

<210> SEQ ID NO 12
<211> LENGTH: 28
<212> TYPE: DNA
<213> ORGANISM: Artificial Sequence
<220> FEATURE:
<223> OTHER INFORMATION: Synthetic Oglionucleotide

<400> SEQUENCE: 12
ctgaatactt gaggtcactg ttctcggg                                    28

<210> SEQ ID NO 13
<211> LENGTH: 24
<212> TYPE: DNA
<213> ORGANISM: Artificial Sequence
<220> FEATURE:
<223> OTHER INFORMATION: Synthetic Oglionucleotide

<400> SEQUENCE: 13
catcgccagc ctcggaacaa acag                                        24

<210> SEQ ID NO 14
<211> LENGTH: 24
<212> TYPE: DNA
<213> ORGANISM: Artificial Sequence
<220> FEATURE:
<223> OTHER INFORMATION: Synthetic Oglionucleotide

<400> SEQUENCE: 14
tgcgcaaatg gaactggagg caac                                    24

<210> SEQ ID NO 15
<211> LENGTH: 18
<212> TYPE: DNA
<213> ORGANISM: Artificial Sequence
<220> FEATURE:
<223> OTHER INFORMATION: Synthetic Oglionucleotide

<400> SEQUENCE: 15
cagcctttcc acccaacg                                           18

<210> SEQ ID NO 16
<211> LENGTH: 18
<212> TYPE: DNA
<213> ORGANISM: Artificial Sequence
<220> FEATURE:
<223> OTHER INFORMATION: Synthetic Oglionucleotide

<400> SEQUENCE: 16
gtggcggtca taggcagc                                           18

<210> SEQ ID NO 17
<211> LENGTH: 23
<212> TYPE: DNA
<213> ORGANISM: Artificial Sequence
<220> FEATURE:
<223> OTHER INFORMATION: Synthetic Oglionucleotide

<400> SEQUENCE: 17
ccaccccttc ctctttatct agc                                     23

<210> SEQ ID NO 18
<211> LENGTH: 23
<212> TYPE: DNA
<213> ORGANISM: Artificial Sequence
<220> FEATURE:
<223> OTHER INFORMATION: Synthetic Oglionucleotide

<400> SEQUENCE: 18
caggcctcac tgtaggagga ata                                     23

<210> SEQ ID NO 19
<211> LENGTH: 23
<212> TYPE: DNA
<213> ORGANISM: Artificial Sequence
<220> FEATURE:
<223> OTHER INFORMATION: Synthetic Oglionucleotide

<400> SEQUENCE: 19 aaccccctacc agtaccagta cca                                    23

<210> SEQ ID NO 20
<211> LENGTH: 23
<212> TYPE: DNA
<213> ORGANISM: Artificial Sequence
<220> FEATURE:
<223> OTHER INFORMATION: Synthetic Oglionucleotide

<400> SEQUENCE: 20
ctgtgtttgc gtcagtccta gag                                     23

<210> SEQ ID NO 21

```
<211> LENGTH: 22
<212> TYPE: DNA
<213> ORGANISM: Artificial Sequence
<220> FEATURE:
<223> OTHER INFORMATION: Synthetic Oglionucleotide

<400> SEQUENCE: 21
taagaaccgg aggcaaagag ac                                              22

<210> SEQ ID NO 22
<211> LENGTH: 22
<212> TYPE: DNA
<213> ORGANISM: Artificial Sequence
<220> FEATURE:
<223> OTHER INFORMATION: Synthetic Oglionucleotide

<400> SEQUENCE: 22
taggaaccca agtccaccaa ac                                              22

<210> SEQ ID NO 23
<211> LENGTH: 22
<212> TYPE: DNA
<213> ORGANISM: Artificial Sequence
<220> FEATURE:
<223> OTHER INFORMATION: Synthetic Oglionucleotide

<400> SEQUENCE: 23
aagtcacgtg gccgaggcag aa                                              22

<210> SEQ ID NO 24
<211> LENGTH: 24
<212> TYPE: DNA
<213> ORGANISM: Artificial Sequence
<220> FEATURE:
<223> OTHER INFORMATION: Synthetic Oglionucleotide

<400> SEQUENCE: 24
tccacaccac ctcggacacc agtt                                            24

<210> SEQ ID NO 25
<211> LENGTH: 29
<212> TYPE: DNA
<213> ORGANISM: Artificial Sequence
<220> FEATURE:
<223> OTHER INFORMATION: Synthetic Oglionucleotide

<400> SEQUENCE: 25
attcttcgtt gtcaagccgc caaagtgga                                       29

<210> SEQ ID NO 26
<211> LENGTH: 29
<212> TYPE: DNA
<213> ORGANISM: Artificial Sequence
<220> FEATURE:
<223> OTHER INFORMATION: Synthetic Oglionucleotide

<400> SEQUENCE: 26
agttgtttgc tgcggagttg tcatctcgt                                       29

<210> SEQ ID NO 27
<211> LENGTH: 18
<212> TYPE: DNA
<213> ORGANISM: Artificial Sequence
<220> FEATURE:
<223> OTHER INFORMATION: Synthetic Oglionucleotide

<400> SEQUENCE: 27
```
aacgggaagc ccatcacc                                                    18

<210> SEQ ID NO 28
<211> LENGTH: 18
<212> TYPE: DNA
<213> ORGANISM: Artificial Sequence
<220> FEATURE:
<223> OTHER INFORMATION: Synthetic Oglionucleotide

<400> SEQUENCE: 28
cagccttggc agcaccag                                                    18

<210> SEQ ID NO 29
<211> LENGTH: 20
<212> TYPE: DNA
<213> ORGANISM: Artificial Sequence
<220> FEATURE:
<223> OTHER INFORMATION: Synthetic Oglionucleotide

<400> SEQUENCE: 29
tcaccaccac ccaggtcagc                                                  20

<210> SEQ ID NO 30
<211> LENGTH: 20
<212> TYPE: DNA
<213> ORGANISM: Artificial Sequence
<220> FEATURE:
<223> OTHER INFORMATION: Synthetic Oglionucleotide

<400> SEQUENCE: 30
ccctgcagca gaaggaccga                                                  20

<210> SEQ ID NO 31
<211> LENGTH: 20
<212> TYPE: DNA
<213> ORGANISM: Artificial Sequence
<220> FEATURE:
<223> OTHER INFORMATION: Synthetic Oglionucleotide

<400> SEQUENCE: 31
cgcgtaccca tccaggagca                                                  20

<210> SEQ ID NO 32
<211> LENGTH: 20
<212> TYPE: DNA
<213> ORGANISM: Artificial Sequence
<220> FEATURE:
<223> OTHER INFORMATION: Synthetic Oglionucleotide

<400> SEQUENCE: 32
gggccactgg gggattcact                                                  20

<210> SEQ ID NO 33
<211> LENGTH: 20
<212> TYPE: DNA
<213> ORGANISM: Artificial Sequence
<220> FEATURE:
<223> OTHER INFORMATION: Synthetic Oglionucleotide

<400> SEQUENCE: 33 tcccctttcta ccagcgcagc                                                 20

<210> SEQ ID NO 34
<211> LENGTH: 20
<212> TYPE: DNA

```
<213> ORGANISM: Artificial Sequence
<220> FEATURE:
<223> OTHER INFORMATION: Synthetic Oglionucleotide

<400> SEQUENCE: 34
tcccagcagc cactgtggag                                                20

<210> SEQ ID NO 35
<211> LENGTH: 20
<212> TYPE: DNA
<213> ORGANISM: Artificial Sequence
<220> FEATURE:
<223> OTHER INFORMATION: Synthetic Oglionucleotide

<400> SEQUENCE: 35
agtgtcccct tcgctcctgc                                                20

<210> SEQ ID NO 36
<211> LENGTH: 20
<212> TYPE: DNA
<213> ORGANISM: Artificial Sequence
<220> FEATURE:
<223> OTHER INFORMATION: Synthetic Oglionucleotide

<400> SEQUENCE: 36
gcttggcggc catcttcagc                                                20

<210> SEQ ID NO 37
<211> LENGTH: 20
<212> TYPE: DNA
<213> ORGANISM: Artificial Sequence
<220> FEATURE:
<223> OTHER INFORMATION: Synthetic Oglionucleotide

<400> SEQUENCE: 37
ccgcctcggt caagtcggaa                                                20

<210> SEQ ID NO 38
<211> LENGTH: 20
<212> TYPE: DNA
<213> ORGANISM: Artificial Sequence
<220> FEATURE:
<223> OTHER INFORMATION: Synthetic Oglionucleotide

<400> SEQUENCE: 38
gcgaggagct gggatgtggt                                                20

<210> SEQ ID NO 39
<211> LENGTH: 20
<212> TYPE: DNA
<213> ORGANISM: Artificial Sequence
<220> FEATURE:
<223> OTHER INFORMATION: Synthetic Oglionucleotide

<400> SEQUENCE: 39 ccagccccctt ttcccctgga                                               20

<210> SEQ ID NO 40
<211> LENGTH: 20
<212> TYPE: DNA
<213> ORGANISM: Artificial Sequence
<220> FEATURE:
<223> OTHER INFORMATION: Synthetic Oglionucleotide

<400> SEQUENCE: 40
gggcagctgc agtggagaga                                                20
```

<210> SEQ ID NO 41
<211> LENGTH: 20
<212> TYPE: DNA
<213> ORGANISM: Artificial Sequence
<220> FEATURE:
<223> OTHER INFORMATION: Synthetic Oglionucleotide

<400> SEQUENCE: 41
agcacggcgc agtcgtttct                                               20

<210> SEQ ID NO 42
<211> LENGTH: 20
<212> TYPE: DNA
<213> ORGANISM: Artificial Sequence
<220> FEATURE:
<223> OTHER INFORMATION: Synthetic Oglionucleotide

<400> SEQUENCE: 42
ttgggggctc aggggaaagg                                               20

<210> SEQ ID NO 43
<211> LENGTH: 20
<212> TYPE: DNA
<213> ORGANISM: Artificial Sequence
<220> FEATURE:
<223> OTHER INFORMATION: Synthetic Oglionucleotide

<400> SEQUENCE: 43
gtgacgcagg tgtcctcggt                                               20

<210> SEQ ID NO 44
<211> LENGTH: 20
<212> TYPE: DNA
<213> ORGANISM: Artificial Sequence
<220> FEATURE:
<223> OTHER INFORMATION: Synthetic Oglionucleotide

<400> SEQUENCE: 44
tctccccgca tctgcttccg                                               20

<210> SEQ ID NO 45
<211> LENGTH: 20
<212> TYPE: DNA
<213> ORGANISM: Artificial Sequence
<220> FEATURE:
<223> OTHER INFORMATION: Synthetic Oglionucleotide

<400> SEQUENCE: 45
cgccgacgag accggatcaa                                               20

<210> SEQ ID NO 46
<211> LENGTH: 20
<212> TYPE: DNA
<213> ORGANISM: Artificial Sequence
<220> FEATURE:
<223> OTHER INFORMATION: Synthetic Oglionucleotide

<400> SEQUENCE: 46
gttctggggc agcaacagcg                                               20

<210> SEQ ID NO 47
<211> LENGTH: 20
<212> TYPE: DNA
<213> ORGANISM: Artificial Sequence
<220> FEATURE:

<223> OTHER INFORMATION: Synthetic Oglionucleotide

<400> SEQUENCE: 47
acctgagctc cgtggaaggc                                               20

<210> SEQ ID NO 48
<211> LENGTH: 20
<212> TYPE: DNA
<213> ORGANISM: Artificial Sequence
<220> FEATURE:
<223> OTHER INFORMATION: Synthetic Oglionucleotide

<400> SEQUENCE: 48
gctgctgcgt ttgggggaag                                               20

<210> SEQ ID NO 49
<211> LENGTH: 20
<212> TYPE: DNA
<213> ORGANISM: Artificial Sequence
<220> FEATURE:
<223> OTHER INFORMATION: Synthetic Oglionucleotide

<400> SEQUENCE: 49
cgacctggct ttccctcgct                                               20

<210> SEQ ID NO 50
<211> LENGTH: 20
<212> TYPE: DNA
<213> ORGANISM: Artificial Sequence
<220> FEATURE:
<223> OTHER INFORMATION: Synthetic Oglionucleotide

<400> SEQUENCE: 50
cttgtgatcg gggtcggcct                                               20

<210> SEQ ID NO 51
<211> LENGTH: 20
<212> TYPE: DNA
<213> ORGANISM: Artificial Sequence
<220> FEATURE:
<223> OTHER INFORMATION: Synthetic Oglionucleotide

<400> SEQUENCE: 51
tcaccgcggt cactgcctac                                               20

<210> SEQ ID NO 52
<211> LENGTH: 20
<212> TYPE: DNA
<213> ORGANISM: Artificial Sequence
<220> FEATURE:
<223> OTHER INFORMATION: Synthetic Oglionucleotide

<400> SEQUENCE: 52
gggagcccca ggttcacaca                                               20

<210> SEQ ID NO 53
<211> LENGTH: 20
<212> TYPE: DNA
<213> ORGANISM: Artificial Sequence
<220> FEATURE:
<223> OTHER INFORMATION: Synthetic Oglionucleotide

<400> SEQUENCE: 53
cgacttcccc atgtccgcct                                               20

<210> SEQ ID NO 54
<211> LENGTH: 20
<212> TYPE: DNA
<213> ORGANISM: Artificial Sequence
<220> FEATURE:
<223> OTHER INFORMATION: Synthetic Oglionucleotide

<400> SEQUENCE: 54
acatccgcct cccggacttg                                          20

<210> SEQ ID NO 55
<211> LENGTH: 20
<212> TYPE: DNA
<213> ORGANISM: Artificial Sequence
<220> FEATURE:
<223> OTHER INFORMATION: Synthetic Oglionucleotide

<400> SEQUENCE: 55
cgtgtgggcc gtgaggatga                                          20

<210> SEQ ID NO 56
<211> LENGTH: 20
<212> TYPE: DNA
<213> ORGANISM: Artificial Sequence
<220> FEATURE:
<223> OTHER INFORMATION: Synthetic Oglionucleotide

<400> SEQUENCE: 56
tccgtccagg ggctctaggt                                          20

<210> SEQ ID NO 57
<211> LENGTH: 20
<212> TYPE: DNA
<213> ORGANISM: Artificial Sequence
<220> FEATURE:
<223> OTHER INFORMATION: Synthetic Oglionucleotide

<400> SEQUENCE: 57
caaccccgtc cccagtggaa                                          20

<210> SEQ ID NO 58
<211> LENGTH: 20
<212> TYPE: DNA
<213> ORGANISM: Artificial Sequence
<220> FEATURE:
<223> OTHER INFORMATION: Synthetic Oglionucleotide

<400> SEQUENCE: 58
tcactcctgg ctggatggcg                                          20

<210> SEQ ID NO 59
<211> LENGTH: 20
<212> TYPE: DNA
<213> ORGANISM: Artificial Sequence
<220> FEATURE:
<223> OTHER INFORMATION: Synthetic Oglionucleotide

<400> SEQUENCE: 59
ccacccgttg agccagtcct                                          20

<210> SEQ ID NO 60
<211> LENGTH: 20
<212> TYPE: DNA
<213> ORGANISM: Artificial Sequence
<220> FEATURE:
<223> OTHER INFORMATION: Synthetic Oglionucleotide

<400> SEQUENCE: 60
cggcagtgca ggcaatggac                                              20

<210> SEQ ID NO 61
<211> LENGTH: 20
<212> TYPE: DNA
<213> ORGANISM: Artificial Sequence
<220> FEATURE:
<223> OTHER INFORMATION: Synthetic Oglionucleotide

<400> SEQUENCE: 61
gtccagcaca ggcagggagt                                              20

<210> SEQ ID NO 62
<211> LENGTH: 20
<212> TYPE: DNA
<213> ORGANISM: Artificial Sequence
<220> FEATURE:
<223> OTHER INFORMATION: Synthetic Oglionucleotide

<400> SEQUENCE: 62
atgtgtctgg agagggcggc                                              20

<210> SEQ ID NO 63
<211> LENGTH: 20
<212> TYPE: DNA
<213> ORGANISM: Artificial Sequence
<220> FEATURE:
<223> OTHER INFORMATION: Synthetic Oglionucleotide

<400> SEQUENCE: 63
cgacagccct ccatacggca                                              20

<210> SEQ ID NO 64
<211> LENGTH: 20
<212> TYPE: DNA
<213> ORGANISM: Artificial Sequence
<220> FEATURE:
<223> OTHER INFORMATION: Synthetic Oglionucleotide

<400> SEQUENCE: 64
ccagcaggtc tgcactggga                                              20

<210> SEQ ID NO 65
<211> LENGTH: 20
<212> TYPE: DNA
<213> ORGANISM: Artificial Sequence
<220> FEATURE:
<223> OTHER INFORMATION: Synthetic Oglionucleotide

<400> SEQUENCE: 65
aagccgtgga gtgctgccaa                                              20

<210> SEQ ID NO 66
<211> LENGTH: 20
<212> TYPE: DNA
<213> ORGANISM: Artificial Sequence
<220> FEATURE:
<223> OTHER INFORMATION: Synthetic Oglionucleotide

<400> SEQUENCE: 66
gcccctccac acctcaccat                                              20

<210> SEQ ID NO 67
<211> LENGTH: 20

-continued

<212> TYPE: DNA
<213> ORGANISM: Artificial Sequence
<220> FEATURE:
<223> OTHER INFORMATION: Synthetic Oglionucleotide

<400> SEQUENCE: 67
ctggacacac acccctgcct                                               20

<210> SEQ ID NO 68
<211> LENGTH: 20
<212> TYPE: DNA
<213> ORGANISM: Artificial Sequence
<220> FEATURE:
<223> OTHER INFORMATION: Synthetic Oglionucleotide

<400> SEQUENCE: 68
gttggtgggg tcgtccaggt                                               20

<210> SEQ ID NO 69
<211> LENGTH: 20
<212> TYPE: DNA
<213> ORGANISM: Artificial Sequence
<220> FEATURE:
<223> OTHER INFORMATION: Synthetic Oglionucleotide

<400> SEQUENCE: 69
gggaggcgca ggcaagagta                                               20

<210> SEQ ID NO 70
<211> LENGTH: 20
<212> TYPE: DNA
<213> ORGANISM: Artificial Sequence
<220> FEATURE:
<223> OTHER INFORMATION: Synthetic Oglionucleotide

<400> SEQUENCE: 70
cttggggttc tccagggcca                                               20

<210> SEQ ID NO 71
<211> LENGTH: 20
<212> TYPE: DNA
<213> ORGANISM: Artificial Sequence
<220> FEATURE:
<223> OTHER INFORMATION: Synthetic Oglionucleotide

<400> SEQUENCE: 71
agacactgcc tgggctgacc                                               20

<210> SEQ ID NO 72
<211> LENGTH: 20
<212> TYPE: DNA
<213> ORGANISM: Artificial Sequence
<220> FEATURE:
<223> OTHER INFORMATION: Synthetic Oglionucleotide

<400> SEQUENCE: 72
gcggggacag gaccaaagga                                               20

<210> SEQ ID NO 73
<211> LENGTH: 20
<212> TYPE: DNA
<213> ORGANISM: Artificial Sequence
<220> FEATURE:
<223> OTHER INFORMATION: Synthetic Oglionucleotide

<400> SEQUENCE: 73
cgagtgtgac cccagccctt        20

<210> SEQ ID NO 74
<211> LENGTH: 20
<212> TYPE: DNA
<213> ORGANISM: Artificial Sequence
<220> FEATURE:
<223> OTHER INFORMATION: Synthetic Oglionucleotide

<400> SEQUENCE: 74
ccattgtggc agggtgcgtg        20

<210> SEQ ID NO 75
<211> LENGTH: 20
<212> TYPE: DNA
<213> ORGANISM: Artificial Sequence
<220> FEATURE:
<223> OTHER INFORMATION: Synthetic Oglionucleotide

<400> SEQUENCE: 75
gctgctaccc cagccagtgt        20

<210> SEQ ID NO 76
<211> LENGTH: 20
<212> TYPE: DNA
<213> ORGANISM: Artificial Sequence
<220> FEATURE:
<223> OTHER INFORMATION: Synthetic Oglionucleotide

<400> SEQUENCE: 76
cgtggacagg aagcgggtca        20

<210> SEQ ID NO 77
<211> LENGTH: 20
<212> TYPE: DNA
<213> ORGANISM: Artificial Sequence
<220> FEATURE:
<223> OTHER INFORMATION: Synthetic Oglionucleotide

<400> SEQUENCE: 77
agtgagaggc aacctggaga        20

<210> SEQ ID NO 78
<211> LENGTH: 20
<212> TYPE: DNA
<213> ORGANISM: Artificial Sequence
<220> FEATURE:
<223> OTHER INFORMATION: Synthetic Oglionucleotide

<400> SEQUENCE: 78
gtgaagtgag ggctcccata        20

<210> SEQ ID NO 79
<211> LENGTH: 22
<212> TYPE: DNA
<213> ORGANISM: Artificial Sequence
<220> FEATURE:
<223> OTHER INFORMATION: Synthetic Oglionucleotide

<400> SEQUENCE: 79
agaattcgct tgagtattct ga        22

<210> SEQ ID NO 80
<211> LENGTH: 22
<212> TYPE: DNA
<213> ORGANISM: Artificial Sequence
<220> FEATURE:
<223> OTHER INFORMATION: Synthetic Oglionucleotide

<400> SEQUENCE: 80
ggctttcagg ttatttgact ga                                    22

<210> SEQ ID NO 81
<211> LENGTH: 19
<212> TYPE: DNA
<213> ORGANISM: Artificial Sequence
<220> FEATURE:
<223> OTHER INFORMATION: Synthetic Oglionucleotide

<400> SEQUENCE: 81
gtactcagcg ccagcatcg                                        19

<210> SEQ ID NO 82
<211> LENGTH: 20
<212> TYPE: DNA
<213> ORGANISM: Artificial Sequence
<220> FEATURE:
<223> OTHER INFORMATION: Synthetic Oglionucleotide

<400> SEQUENCE: 82
agccacatcg ctcagacacc                                       20

<210> SEQ ID NO 83
<211> LENGTH: 20
<212> TYPE: DNA
<213> ORGANISM: Artificial Sequence
<220> FEATURE:
<223> OTHER INFORMATION: Synthetic Oglionucleotide

<400> SEQUENCE: 83
tgagggctgt gtgctgaggg                                       20

<210> SEQ ID NO 84
<211> LENGTH: 20
<212> TYPE: DNA
<213> ORGANISM: Artificial Sequence
<220> FEATURE:
<223> OTHER INFORMATION: Synthetic Oglionucleotide

<400> SEQUENCE: 84
ccgctcccac gtcactcctt                                       20

<210> SEQ ID NO 85
<211> LENGTH: 20
<212> TYPE: DNA
<213> ORGANISM: Artificial Sequence
<220> FEATURE:
<223> OTHER INFORMATION: Synthetic Oglionucleotide

<400> SEQUENCE: 85
tcaccctacc ccagcccta                                        20

<210> SEQ ID NO 86
<211> LENGTH: 20
<212> TYPE: DNA
<213> ORGANISM: Artificial Sequence
<220> FEATURE:
<223> OTHER INFORMATION: Synthetic Oglionucleotide

<400> SEQUENCE: 86
gctggcattg tggctcacgg                                       20

<210> SEQ ID NO 87
<211> LENGTH: 20
<212> TYPE: DNA
<213> ORGANISM: Artificial Sequence
<220> FEATURE:
<223> OTHER INFORMATION: Synthetic Oglionucleotide

<400> SEQUENCE: 87
ggaacccgaa gtggggagca                                            20

<210> SEQ ID NO 88
<211> LENGTH: 20
<212> TYPE: DNA
<213> ORGANISM: Artificial Sequence
<220> FEATURE:
<223> OTHER INFORMATION: Synthetic Oglionucleotide

<400> SEQUENCE: 88
gccaccttcc aggtgtccga                                            20

<210> SEQ ID NO 89
<211> LENGTH: 25
<212> TYPE: DNA
<213> ORGANISM: Artificial Sequence
<220> FEATURE:
<223> OTHER INFORMATION: Synthetic Oglionucleotide

<400> SEQUENCE: 89 agacccttg aagtcaagga caccg                                       25

<210> SEQ ID NO 90
<211> LENGTH: 24
<212> TYPE: DNA
<213> ORGANISM: Artificial Sequence
<220> FEATURE:
<223> OTHER INFORMATION: Synthetic Oglionucleotide

<400> SEQUENCE: 90
cattgctgaa gaccttagtg atgc                                       24

<210> SEQ ID NO 91
<211> LENGTH: 20
<212> TYPE: DNA
<213> ORGANISM: Artificial Sequence
<220> FEATURE:
<223> OTHER INFORMATION: Synthetic Oglionucleotide

<400> SEQUENCE: 91
tcaaggatgc caggaacaag                                            20

<210> SEQ ID NO 92
<211> LENGTH: 19
<212> TYPE: DNA
<213> ORGANISM: Artificial Sequence
<220> FEATURE:
<223> OTHER INFORMATION: Synthetic Oglionucleotide

<400> SEQUENCE: 92
gcttgcactg aagccagag                                             19

<210> SEQ ID NO 93
<211> LENGTH: 20
<212> TYPE: DNA
<213> ORGANISM: Artificial Sequence
<220> FEATURE:
<223> OTHER INFORMATION: Synthetic Oglionucleotide

```
<400> SEQUENCE: 93
tcctgccgct gtggagtctg                                              20

<210> SEQ ID NO 94
<211> LENGTH: 20
<212> TYPE: DNA
<213> ORGANISM: Artificial Sequence
<220> FEATURE:
<223> OTHER INFORMATION: Synthetic Oglionucleotide

<400> SEQUENCE: 94
cggagttggc tggcaggagt                                              20

<210> SEQ ID NO 95
<211> LENGTH: 20
<212> TYPE: DNA
<213> ORGANISM: Artificial Sequence
<220> FEATURE:
<223> OTHER INFORMATION: Synthetic Oglionucleotide

<400> SEQUENCE: 95
gtcaacacca ccatctgtgc                                              20

<210> SEQ ID NO 96
<211> LENGTH: 20
<212> TYPE: DNA
<213> ORGANISM: Artificial Sequence
<220> FEATURE:
<223> OTHER INFORMATION: Synthetic Oglionucleotide

<400> SEQUENCE: 96
ggcctttgag gaagaggagt                                              20

<210> SEQ ID NO 97
<211> LENGTH: 24
<212> TYPE: DNA
<213> ORGANISM: Artificial Sequence
<220> FEATURE:
<223> OTHER INFORMATION: Synthetic Oglionucleotide

<400> SEQUENCE: 97
ttccctcgac acccgattca aagt                                         24

<210> SEQ ID NO 98
<211> LENGTH: 24
<212> TYPE: DNA
<213> ORGANISM: Artificial Sequence
<220> FEATURE:
<223> OTHER INFORMATION: Synthetic Oglionucleotide

<400> SEQUENCE: 98
agctgttgct gttgtgctta accc                                         24

<210> SEQ ID NO 99
<211> LENGTH: 20
<212> TYPE: DNA
<213> ORGANISM: Artificial Sequence
<220> FEATURE:
<223> OTHER INFORMATION: Synthetic Oglionucleotide

<400> SEQUENCE: 99
ctccgctgcg agatggagca                                              20

<210> SEQ ID NO 100
```

```
<211> LENGTH: 20
<212> TYPE: DNA
<213> ORGANISM: Artificial Sequence
<220> FEATURE:
<223> OTHER INFORMATION: Synthetic Oglionucleotide

<400> SEQUENCE: 100
aaggacctgc tcgtgggtgg                                               20

<210> SEQ ID NO 101
<211> LENGTH: 25
<212> TYPE: DNA
<213> ORGANISM: Artificial Sequence
<220> FEATURE:
<223> OTHER INFORMATION: Synthetic Oglionucleotide

<400> SEQUENCE: 101
gcctgttctc ctggggcttt gctgc                                         25

<210> SEQ ID NO 102
<211> LENGTH: 25
<212> TYPE: DNA
<213> ORGANISM: Artificial Sequence
<220> FEATURE:
<223> OTHER INFORMATION: Synthetic Oglionucleotide

<400> SEQUENCE: 102
catccacctc acagatcgcc tacac                                         25

<210> SEQ ID NO 103
<211> LENGTH: 20
<212> TYPE: DNA
<213> ORGANISM: Artificial Sequence
<220> FEATURE:
<223> OTHER INFORMATION: Synthetic Oglionucleotide

<400> SEQUENCE: 103
ctcccagtct cctcctcgcc                                               20

<210> SEQ ID NO 104
<211> LENGTH: 20
<212> TYPE: DNA
<213> ORGANISM: Artificial Sequence
<220> FEATURE:
<223> OTHER INFORMATION: Synthetic Oglionucleotide

<400> SEQUENCE: 104
tgcggacgtc tggaacggag                                               20

<210> SEQ ID NO 105
<211> LENGTH: 20
<212> TYPE: DNA
<213> ORGANISM: Artificial Sequence
<220> FEATURE:
<223> OTHER INFORMATION: Synthetic Oglionucleotide

<400> SEQUENCE: 105
gcgttccctg ctgagaccct                                               20

<210> SEQ ID NO 106
<211> LENGTH: 20
<212> TYPE: DNA
<213> ORGANISM: Artificial Sequence
<220> FEATURE:
<223> OTHER INFORMATION: Synthetic Oglionucleotide

<400> SEQUENCE: 106
```
tgaggcccag gggcatcttc                                                    20

<210> SEQ ID NO 107
<211> LENGTH: 20
<212> TYPE: DNA
<213> ORGANISM: Artificial Sequence
<220> FEATURE:
<223> OTHER INFORMATION: Synthetic Oglionucleotide

<400> SEQUENCE: 107
tgggggcgtc aggtctttcc                                                    20

<210> SEQ ID NO 108
<211> LENGTH: 20
<212> TYPE: DNA
<213> ORGANISM: Artificial Sequence
<220> FEATURE:
<223> OTHER INFORMATION: Synthetic Oglionucleotide

<400> SEQUENCE: 108
caggcgaagg actggcagga                                                    20

<210> SEQ ID NO 109
<211> LENGTH: 20
<212> TYPE: DNA
<213> ORGANISM: Artificial Sequence
<220> FEATURE:
<223> OTHER INFORMATION: Synthetic Oglionucleotide

<400> SEQUENCE: 109
agggcaagca caactcggca                                                    20

<210> SEQ ID NO 110
<211> LENGTH: 20
<212> TYPE: DNA
<213> ORGANISM: Artificial Sequence
<220> FEATURE:
<223> OTHER INFORMATION: Synthetic Oglionucleotide

<400> SEQUENCE: 110
catgtcggcg tcggtgagga                                                    20

<210> SEQ ID NO 111
<211> LENGTH: 20
<212> TYPE: DNA
<213> ORGANISM: Artificial Sequence
<220> FEATURE:
<223> OTHER INFORMATION: Synthetic Oglionucleotide

<400> SEQUENCE: 111
cgggaggtgg aagaggaggg                                                    20

<210> SEQ ID NO 112
<211> LENGTH: 20
<212> TYPE: DNA
<213> ORGANISM: Artificial Sequence
<220> FEATURE:
<223> OTHER INFORMATION: Synthetic Oglionucleotide

<400> SEQUENCE: 112
gccgcgtccc ggctctaata                                                    20

<210> SEQ ID NO 113
<211> LENGTH: 20
<212> TYPE: DNA

```
<213> ORGANISM: Artificial Sequence
<220> FEATURE:
<223> OTHER INFORMATION: Synthetic Oglionucleotide

<400> SEQUENCE: 113
gcagaggtcc tatcccatga                                                    20

<210> SEQ ID NO 114
<211> LENGTH: 20
<212> TYPE: DNA
<213> ORGANISM: Artificial Sequence
<220> FEATURE:
<223> OTHER INFORMATION: Synthetic Oglionucleotide

<400> SEQUENCE: 114
ctgggtggaa agagaagctg                                                    20

<210> SEQ ID NO 115
<211> LENGTH: 20
<212> TYPE: DNA
<213> ORGANISM: Artificial Sequence
<220> FEATURE:
<223> OTHER INFORMATION: Synthetic Oglionucleotide

<400> SEQUENCE: 115
acgctctgca cttctcgact                                                    20

<210> SEQ ID NO 116
<211> LENGTH: 20
<212> TYPE: DNA
<213> ORGANISM: Artificial Sequence
<220> FEATURE:
<223> OTHER INFORMATION: Synthetic Oglionucleotide

<400> SEQUENCE: 116
acttgcctca tccgagtcac                                                    20

<210> SEQ ID NO 117
<211> LENGTH: 20
<212> TYPE: DNA
<213> ORGANISM: Artificial Sequence
<220> FEATURE:
<223> OTHER INFORMATION: Synthetic Oglionucleotide

<400> SEQUENCE: 117
cagccactgc tctaccatga                                                    20

<210> SEQ ID NO 118
<211> LENGTH: 20
<212> TYPE: DNA
<213> ORGANISM: Artificial Sequence
<220> FEATURE:
<223> OTHER INFORMATION: Synthetic Oglionucleotide

<400> SEQUENCE: 118
gcagctccct cttgtacgtc                                                    20
```

METHODS FOR GENERATING INNER EAR CELLS IN VITRO

CROSS REFERENCE TO RELATED APPLICATIONS

Pursuant to 35 U.S.C. §119 (e), this application claims priority to the filing date of U.S. Provisional Patent Application Ser. No. 61/435,541, filed Jan. 24, 2011, and U.S. Provisional Patent Application Ser. No. 61/484,095, filed May 9, 2011; the full disclosures of which are herein incorporated by reference.

GOVERNMENT RIGHTS

This invention was made with government support under contracts DC006167 and P30DC010363 awarded by the National Institutes of Health. The Government has certain rights in this invention. The invention was also made with support from the California Institute of Regenerative Medicine under grant No. RC1-00119.

FIELD OF THE INVENTION

This invention pertains to methods of producing inner ear sensory hair cells and supporting cells.

BACKGROUND OF THE INVENTION

Mechanosensitive sensory hair cells are the linchpin of our senses of hearing and balance. Our inner ear harbors about 15,000 cochlear and about the same number of vestibular sensory hair cells, which are the mechanoreceptors of our senses of hearing and balance. Because of their paucity, molecular studies on hair cells have been limited, and, consequently the molecular basis of their function is unknown. Aside from being scarce, hair cells are also sensitive to mechanical and chemical insults. Acoustical overstimulation, chemotherapy, aminoglycoside drug side effects, the effects of aging, and increasingly noisy environments contribute to the deterioration of hearing over time. As a result, hundreds of millions of patients worldwide are permanently debilitated by hearing loss and balance problems. The main reason for the permanence of these chronic disorders is the fact that mammalian cochlear hair cells do not spontaneously regenerate and that the limited regeneration observed in the vestibular system is inadequate to restore function. Protocols to generate inner ear sensory hair cells and supporting cells in vitro would find great use as a platform for testing compounds with respect to ototoxicity, otoprotection, and otoregeneration. The present invention addresses these issues.

PUBLICATIONS

Methods for generating hair cells from embryonic stem cells in mice are described in Li et al. (2003) PNAS 100(23): 13495-13500, Oshima et al. (2010) Cell 141:704-716, Published US Application No. 2005/0287127 and Published US Application No. 2008/0267929.

SUMMARY OF THE INVENTION

Methods, compositions and kits are provided for generating inner ear cells in vitro. These methods find use in a number of applications, such as in preparing inner ear cells for in vitro screening for agents that are toxic to inner ear cells, for in vitro screening for agents that prevent against, mitigate, or reverse the toxic effects of such agents, and for in vitro screening for agents that promote otoregeneration.

In some aspects of the invention, a method is provided for the generation of inner ear cells from pluripotent stem cells in vitro, the method comprising: (a) culturing pluripotent stem cells in the presence of at least one factor that suppresses the formation of endoderm and mesoderm, and at least one ectoderm rostralizing factor, wherein a population comprising preplacodal ectodermal cells is produced; (b) culturing the population comprising preplacodal ectodermal cells under adherent conditions in the presence of at least one FGF, wherein a population comprising otic progenitor cells is produced; and (c) culturing the population comprising otic progenitor cells under adherent conditions, wherein a population comprising inner ear cells is produced.

In some embodiments, the at least one factor that suppresses the formation of endodermal and mesoderm is selected from an inhibitor of Wnt signaling and an inhibitor of TGFB signaling. In some embodiments, the pluripotent stem cells are cultured in the presence of at least two factors that suppress the formation of endodermal and mesodermal cells. In some embodiments, the at least two factors include at least one inhibitor of Wnt signaling and at least one inhibitor of TGFB signaling. In some embodiments, the at least one ectoderm rostralizing factor is a factor that activates IGF signaling. In some embodiments, factor that suppresses the formation of endoderm and mesoderm and the ectoderm rostralizing factors are provided in a media of constant knockout serum replacement (KSR) concentration. In some embodiments, the factors are provided in a first media, a second media, and a third media provided sequentially over time, wherein the first media comprising a high concentration of KSR (e.g. 18-25%, e.g. 20% KSR), the second media comprises an intermediate concentration of KSR (e.g. 13-17% KSR, e.g. 15%), and the third media comprises a lower concentration of KSR (e.g. 5-12% KSR, e.g. 10%).

In some embodiments, the culturing of preplacodal ectodermal cells to produce a population of otic progenitor cells further comprises: i. culturing the preplacodal ectodermal cells under adherent conditions in the presence of at least one FGF and one or more additional factors that promote the induction of otic progenitor cells; and ii. culturing the induced otic progenitor cells under adherent conditions in the presence of FGF growth factors and one or more additional factors that promote the stabilization of otic progenitor cells. In some embodiments, the one or more additional factors that promote the induction of otic progenitor cells is selected from the group consisting of an inhibitor of BMP signaling, an activator of Wnt signaling, and FGF19. In some embodiments, the one or more additional factors that promote the stabilization of otic progenitor cells is selected from the group consisting of an activator of BMP signaling and FGF19.

In some embodiments, the population comprising preplacodal ectodermal cells is mechanically enriched for preplacodal ectodermal cells prior to culturing in the presence of at least one FGF. In some embodiments, the mechanical enrichment for preplacodal ectodermal cells is by selecting for preplacodal ectodermal cells by fluorescence activated cell sorting (FACS), magnetic-activated cell sorting (MACS), or immunopanning. In some embodiments, the population comprising otic progenitor cells is mechanically enriched for otic progenitor cells prior to culturing to produce inner ear cells. In some embodiments, the mechanical enrichment for otic progenitor cells is by fluorescence activated cell sorting (FACS), magnetic-activated cell sorting (MACS), or immunopanning.

In some embodiments, the otic progenitor cells are expanded prior to culturing to produce inner ear cells. In some embodiments, the expansion comprises culturing under adherent conditions in the presence of SHH. In some embodiments, the expansion comprises culturing under adherent conditions in the presence of at least one FGF. In some embodiments, the otic progenitors are cultured in the absence of growth factors. In some embodiments, the otic progenitors are cultures in the presence of factors that promote differentiation of inner ear cells. In some embodiments, as when the pluripotent stem cells are from human, the culturing of the population comprising otic progenitor cells occurs in the absence of feeder cells. In some embodiments, as when the pluripotent stem cells are from rodent, the culturing of the population comprising otic progenitor cells occurs in the presence of feeder cells, e.g., mesenchymal stromal cells.

In some aspects of the invention, a method is provided for generating human inner ear cells in vitro. In such methods, a population of cells that are enriched for otic progenitor cells is cultured under adherent conditions in the absence of feeder cells, e.g. mesenchymal stromal cells, to form inner ear cells. In some embodiments, the population of cells that is enriched for otic progenitor cells is mechanically enriched for otic progenitor cells, e.g. by enriching methods comprising fluorescence activated cell sorting (FACS), magnetic-activated cell sorting (MACS), or immunopanning. In some embodiments, the population of cells that is enriched for otic progenitor cells is enriched for otic progenitor cells by culturing pluripotent stem cells under conditions that promote the formation of otic progenitor cells. In some embodiments, the population of cells that is enriched for otic progenitor cells is enriched both by culturing for otic progenitor cells and by mechanically enriching for otic progenitor cells. In some embodiments, the enrichment for otic progenitor cells by culturing pluripotent stem cells comprises (a) culturing stem cells in the presence of at least one factor that suppresses the formation of endoderm and mesoderm and at least one ectoderm rostralizing factor, wherein a population comprising preplacodal ectodermal cells is produced; (b) culturing the population comprising preplacodal ectodermal cells under conditions that induce the formation of otic progenitor cells; and (c) culturing the population in which the formation of otic progenitor cells has been induced under conditions that promote the stabilization of otic progenitor cells; wherein a population of cells that are enriched for otic progenitor cells is formed. In some embodiments, the population comprising preplacodal ectodermal cells is mechanically enriched for preplacodal ectodermal cells prior to culturing in step (b). In some embodiments, the otic progenitor cells are expanded prior to culturing to produce inner ear cells. In some embodiments, the expansion is by culturing under adherent conditions in the presence of SHH. In some embodiments, the expansion is by culturing under adherent conditions in the presence of at least one FGF.

In some aspects of the invention, inner ear cells are generated from pluripotent stem cells. In these methods, pluripotent stem cells are cultured in the presence of a Wnt inhibitor, a TGFB inhibitor, and an ectoderm rostralizing factor to produce a population of cells that is enriched for preplacodal ectodermal cells. This enriched population of preplacodal ectodermal cells is then cultured in a second step under adherent conditions in the presence of one or more FGFs to produce a population that is enriched for otic progenitor cells. In some embodiments this culture step comprises a first step, in which the cells are cultured in the presence of an inhibitor of BMP signaling, an activator of Wnt signaling, and/or FGF19 to promote the induction of an otic progenitor cell fate; and a second step, in which the cells are cultured in the presence of an activator of BMP signaling and/or FGF19 to promote the stabilization of otic progenitor cell fate. The population that is enriched for otic progenitor cells is then cultured in a third step under adherent conditions to produce inner ear cells. In some embodiments, e.g. when the otic progenitor cells are mouse cells, the culturing of otic progenitor cells to produce inner ear cells is in the presence of feeder cells. In some embodiments, e.g. when the otic progenitor cells are human cells, the culturing of otic progenitor cells to produce inner ear cells is in the absence of feeder cells.

In some aspects of the invention, a method is provided for screening a candidate agent for toxicity to inner ear cells, the method comprising contacting inner ear cells generated in vitro by methods of the invention with a candidate agent; and comparing the viability and/or function of the inner ear cells contacted with the candidate agent to the viability and/or function of inner ear cells that were not contacted with the candidate agent; wherein a reduction in viability and/or function of inner ear cells contacted with the candidate agent indicates that the candidate agent is toxic to the inner ear cells.

In some aspects of the invention, a method is provided for screening a candidate agent for the ability to protect inner ear cells from a toxic agent, mitigate the effects of a toxic agent on an inner ear cell, or reverse the effects of a toxic agent on an inner ear cell, the method comprising: contacting inner ear cells generated in vitro by methods of the invention with a toxic agent; contacting the inner ear cells with a candidate agent; and comparing the viability and/or function of the inner ear cells contacted with candidate agent to the viability and/or function of inner ear cells that were contacted with toxic agent and were not contacted with the candidate agent; wherein an enhancement in viability and/or function of inner ear cells contacted with the candidate agent indicates that the candidate agent protects inner ear cells from the toxic agent, mitigates the effects of a toxic agent on an inner ear cell, or reverses the effects of a toxic agent on an inner ear cell.

In some aspects of the invention, a method is provided for screening a candidate agent for the ability to promote otoregeneration, the method comprising: contacting inner ear cells generated in vitro by methods of the invention with a toxic agent; contacting the inner ear cells with a candidate agent; and comparing the regenerative response of the inner ear cells contacted with candidate agent to the regenerative response of inner ear cells that were contacted with toxic agent and were not contacted with the candidate agent; wherein an enhancement in the regenerative response indicates that the candidate agent promotes otoregeneration.

BRIEF DESCRIPTION OF THE DRAWINGS

The invention is best understood from the following detailed description when read in conjunction with the accompanying drawings. The patent or application file contains at least one drawing executed in color. Copies of this patent or patent application publication with color drawing(s) will be provided by the Office upon request and payment of the necessary fee. It is emphasized that, according to common practice, the various features of the drawings are not to-scale. On the contrary, the dimensions of the various features are arbitrarily expanded or reduced for clarity. Included in the drawings are the following figures.

FIG. 6H-J. Otic Induction Is Most Efficient in D/S/I-Treated ESCs and iPSCs (continued). (H and I) Coexpression of otic markers Pax2 and Dlx5 (H) and of Pax2 and Pax8 (I) in the majority of ESC-derived cultures after D/S/I and bFGF treatment. (J) Cultures of D/S/I-treated ESC-derived embryoid body cells in absence and presence of bFGF as well as after treatment with SU5402, which virtually diminished Pax2 expression. Nuclear DAPI staining is shown.

FIG. 8A-D. Differentiation into Hair Cell-like Cells. (A) ESCs or iPSCs were cultured in non-adherent condition in presence of Dkk1, SIS3, and IGF-1 (D/S/I) and the resulting embryoid bodies were grown adherently in presence of bFGF. On day 8 (d8), the cells were replated and kept for 12 days without adding additional growth factors (no GF), or maintained on mitotically inactivated chicken utricle stromal cells. (B) When cells were cultured without added growth factors, we observed differentiation into nGFPAtoh1-positive cells that were immunopositive for myosin VIIa but did not display expression of espin or other hair bundle markers. (C and D) When the ESC-(C) and iPSC-(D) derived progenitors were cultured on chicken utricle stromal cells, we found nGFPAtoh1 and myosinVIIa double-positive cells that coexpressed the hair bundle marker espin.

DETAILED DESCRIPTION OF THE INVENTION

Figure 1:
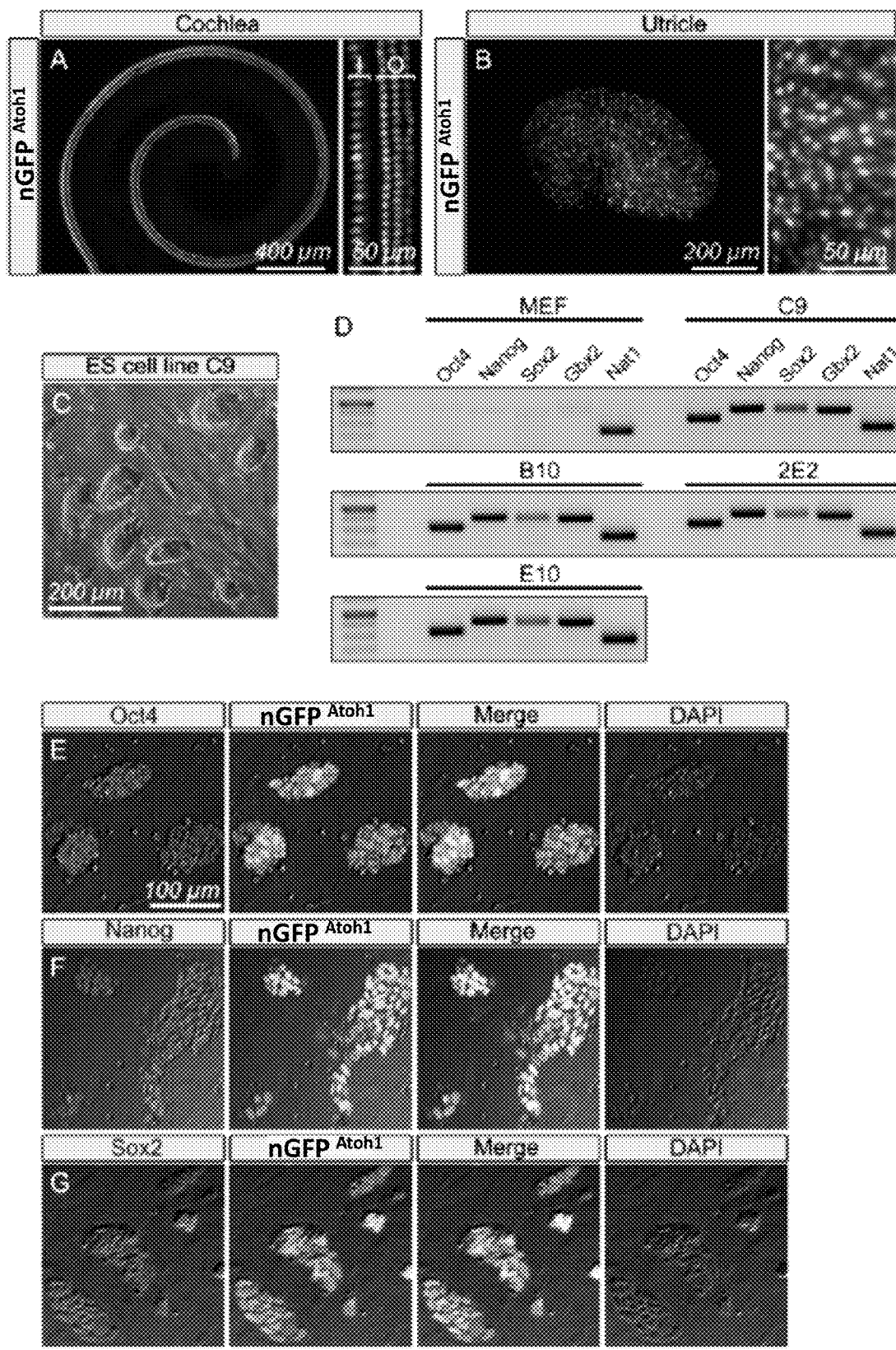
FIG. 1. Derivation of ES Cell Lines from Math1/nGFP Mice, Related to FIGS. 1 (A and B) nGFPAtoh1 expression in the cochlea (A) and utricle (B) of 5-day-old Math1/nGFP mice. Nuclei of inner and outer hair cells (I and O) and of vestibular hair cells are strongly fluorescent. (C) Transmitted light image showing the morphology of one of the derived ES cell lines (C9). (D) RT-PCR-based analysis of expression of ES cell marker genes in MEF feeders and in 4 derived Math1/nGFP ES cell lines (C9, B10, 2E2, and E10) cultured on MEF feeders. Nat1=N-acetyltransferase 1, an ubiquitously expressed control transcript. (E-G) Immunostainings of C9 Math1/nGFP ES cells with antibodies to Oct4, Nanog, and Sox2. nGFPAtoh1 expression is detectable in ES cells, which were maintained on MEF feeder cells. Nuclear DAPI staining is shown.

Before the present methods and compositions are described, it is to be understood that this invention is not limited to particular method or composition described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supercedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g. polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DEFINITIONS

Methods, compositions and kits are provided for generating inner ear cells in vitro.

By "inner ear sensory hair cells" or simply "hair cells" it is meant the mechanosensory hair cells of the cochlea (the auditory system) and of the saccule, utricle, crista ampularis, and semicircular canals (the vestibular system), which contribute to detecting and amplifying sound and to maintaining balance, respectively. Hair cells resemble columnar cells, each with a hair bundle of stereocilia at the apical surface. The deflection of the stereocilia opens mechanically gated ion channels that allow small, positively charged ions (primarily potassium and calcium) to enter the hair cell. Unlike many other electrically active cells, the hair cell itself does not fire an action potential. Rather, the influx of positive ions depolarizes the cell, resulting in a receptor potential. As such, hair cells typically show a graded electrical response rather than action potential spikes typical of other neurons. Hair cells may express detectable levels of one or more of the following markers: atonal homolog 1 (Atoh1/MATH1/HATH1), myosin VI (MYO6), myosin VIIA (MYO7A), Espin (ESPN), myosin heavy chain 3 (MYH2), cadherin23 (CDH23), protocadherin15 (PCDH15), otoferlin (OTOF), prestin (SLC26A5)

By "inner ear supporting cells", or simply "supporting cells" it is meant the cells that contribute to the complex structural and functional properties of the cochlea, e.g., Deiters' (phalangeal) cells, Hensen's cells, Claudius cells, Boettcher cells, pillar cells, marginal cells, and the like, and of the saccule, utricle, crista ampularis, and semicircular canals. Supporting cells are identifiable by short microvilli at their apical cell surface. In addition, they are found in close proximity to hair cells, i.e. they are found directly adjacent to hair cells, as clusters with hair cells. Supporting cells may express detectable levels of one or more of the following markers: cyclin-dependent kinase inhibitor 1B (CDKN1B, p27 (KIP1)), prospero homeobox 1 (PROX1), otoancorin (OTOA), musashi homolog 1 (MSI1), SRY-box 2 (SOX2), gap junction protein beta 2, 26 kDa (Connexin 26), gap junction protein beta 6, kDa (Connexin30), gap junction protein alpha 1, 43 kDa (Connexin43), hairy/enhancer-of-split related with YRPW motif 2 (HEY2). By "pluripotent stem cell" or "pluripotent cell" it is meant a cell that has the ability to differentiate into all types of cells in an organism. Pluripotent cells are capable of forming teratomas and of contributing to ectoderm, mesoderm, or endoderm tissues in a living organism. Examples of pluripotent stem cells are embryonic stem (ES) cells, embryonic germ stem (EG) cells, and induced pluripotent stem (iPS) cells. By "embryonic stem cell" or "ES cell" it is meant a cell that a) can self-renew, b) can differentiate to produce all types of cells in an organism, and c) is derived from the inner cell mass of the blastula of a developing organism. ES cells can be cultured over a long period of time while maintaining the ability to differentiate into all types of cells in an organism. In culture, ES cells typically grow as flat colonies with large nucleo-cytoplasmic ratios, defined borders and prominent nuclei. In addition, ES cells express SSEA-3, SSEA-4, TRA-1-60, TRA-1-81, and Alkaline Phosphatase, but not SSEA-1. Examples of methods of generating and characterizing ES cells may be found in, for example, U.S. Pat. No. 7,029,913, U.S. Pat. No. 5,843,780, and U.S. Pat. No. 6,200,806, the disclosures of which are incorporated herein by reference.

By "embryonic germ stem cell", embryonic germ cell" or "EG cell" it is meant a cell that a) can self-renew, b) can differentiate to produce all types of cells in an organism, and c) is derived from germ cells and germ cell progenitors, e.g. primordial germ cells, i.e. those that would become sperm and eggs. Embryonic germ cells (EG cells) are thought to have properties similar to embryonic stem cells as described above. Examples of methods of generating and characterizing EG cells may be found in, for example, U.S. Pat. No. 7,153, 684; Matsui, Y., et al., (1992) Cell 70:841; Shamblott, M., et al. (2001) Proc. Natl. Acad. Sci. USA 98: 113; Shamblott, M., et al. (1998) Proc. Natl. Acad. Sci. USA, 95:13726; and Koshimizu, U., et al. (1996) Development, 122:1235, the disclosures of which are incorporated herein by reference.

By "induced pluripotent stem cell" or "iPS cell" it is meant a cell that a) can self-renew, b) can differentiate to produce all types of cells in an organism, and c) is derived from a somatic cell. iPS cells have an ES cell-like morphology, growing as flat colonies with large nucleo-cytoplasmic ratios, defined borders and prominent nuclei. In addition, iPS cells express one or more key pluripotency markers known by one of ordinary skill in the art, including but not limited to Alkaline Phosphatase, SSEA3, SSEA4, Sox2, Oct3/4, Nanog, TRA160, TRA181, TDGF 1, Dnmt3b, FoxD3, GDF3, Cyp26a1, TERT, and zfp42. iPS cells may be generated by providing the cell with "reprogramming factors", i.e. one or more, i.e. a cocktail, of biologically active factors that act on a cell to alter transcription, thereby reprogramming a cell to pluripotency. These reprogramming factors may be provided to the cells individually or as a single composition, that is, as a premixed composition, of reprogramming factors. The factors may be provided at the same molar ratio or at different molar ratios. The factors may be provided once or multiple times in the course of culturing the cells of the subject invention. Examples of methods of generating and characterizing iPS cells may be found in, for example, Application Nos. US20090047263, US20090068742, US20090191159, US20090227032, US20090246875, and US20090304646, the disclosures of which are incorporated herein by reference.

By "somatic cell" it is meant any cell in an organism that, in the absence of experimental manipulation, does not ordinarily give rise to all types of cells in an organism. In other words, somatic cells are cells that have differentiated sufficiently that they will not naturally generate cells of all three germ layers of the body, i.e. ectoderm, mesoderm and endoderm. For example, somatic cells would include both neurons and neural progenitors, the latter of which may be able to self-renew and naturally give rise to all or some cell types of the central nervous system but cannot give rise to cells of the mesoderm or endoderm lineages.

By "endoderm" it is meant the germ layer formed during animal embryogenesis that gives rise to the gastrointestinal tract, respiratory tract, endocrine glands and organs, certain structures of the auditory system, and certain structures of the urinary system.

By "mesoderm" it is meant the germ layer formed during animal embryogenesis that gives rise to muscles, cartilage, bones, dermis, the reproductive system, adipose tissue, connective tissues of the gut, peritoneum, certain structures of the urinary system, mesothelium, notochord, and spleen.

By "ectoderm" it is meant the germ layer formed during animal embryogenesis that gives rise to the nervous system, tooth enamel, epidermis, hair, nails, and linings of mucosal tissues.

By "anterior ectoderm" it is meant the region of the ectodermal germ layer at the anterior, or "rostral", end of the embryo, i.e. towards the head region. Anterior ectoderm comprises preplacodal ectoderm and adjacent tissues such as presumptive early ectoderm, presumptive neural crest, and neural tissue. Ectoderm may be induced to become anterior ectoderm by contact with rostralizing factors such as IGF1 or insulin.

By "preplacodal ectoderm" it is meant the narrow band of cells in the anterior ectoderm that surrounds the anterior neural plate at the end of gastrulation and that gives rise to cranial placodes, which in turn give rise to the paired sensory structures of the head. Preplacodal ectoderm cells may express detectable levels of one or more of markers including but not limited to fibroblast growth factor receptor 1 (FGFR1), fibroblast growth factor receptor 2 (FGFR2), fibroblast growth factor receptor 3 (FGFR3), SIX homeobox 1 (SIX1), SIX homeobox 4 (SIX4), eyes absent homolog 1 (EYA1), and eyes absent homolog 2 (EYA2). Preplacodal ectodermal cells are competent to respond to otic induction, that is, the induction of otic progenitor cells by culturing in the presence of FGFs, resulting in the upregulation of Pax2 and Sox10 expression.

By "otic progenitor cells" it is meant a somatic cell that a) can self-renew, and b) can differentiate to give rise to inner ear sensory hair cells and supporting cells. Otic progenitor cells grow as spheres of cells when cultured in culture conditions, or as colonies of cells when cultured in adherent conditions. Furthermore, otic progenitor cells may express detectable levels of one or more of the following markers: paired box 2 (PAX2), paired box 8 (PAX8), distal-less homeobox 5 (DLX5), orthodenticle homeobox 2 (OTX2), eyes absent homolog 1 (EYA1), SIX homeobox 1 (SIX1), jagged 1 (JAG1), fibroblast growth factor receptor 1 (FGFR1). Other markers include forkhead box 13 (FOXI3), SRY-box 2 (SOX2), SRY-box 10 (SOX10), NOTCH1, delta-like 1 (DELTA1), bone morphogenetic protein 7 (BMP7), T-box 1 (TBX1), GATA binding protein 3 (GATA3), myosin VIIA (MYO7A), forkhead box D3 (FOXD3), hairy/enhancer-of-split related with YRPW motif 1 (HEY1), hairy/enhancer-of-split related with YRPW motif 2 (HEY2), hairy and enhancer of split 1 (HES1), hairy and enhancer of split 6 (HES6), Activin receptor (ACTIVIN-R), H6 family homeobox 3 (NKX5.1), Claudin 8 (CLDN8), Claudin 14 (CLDN14).

By "stromal cells" it is meant connective tissue cells of any organ, e.g. fibroblasts, pericytes, endothelial cells, etc.

By "bone morphogenic proteins" or "BMPs" it is meant the family of growth factors that is a subfamily of the transforming growth factor b (TGFb) superfamily. BMPs (e.g. BMP1, BMP2, BMP3, BMP4, BMP5, BMP6, BMP7, BMP8a, BMP8b, BMP9/GDF, BMP10, BMP11/GDF11, BMP12/GDF7, BMP13/GDF6, BMP14/GDF5, BMP15/GDF9B) were first discovered by their ability to induce the formation of bone and cartilage. They are now considered to constitute a group of pivotal morphogenetic signals; additionally, their dysregulation has been linked to a number of pathological processes, including the progression of colon cancer, Barrett's esophagus, and adenocarcinoma in the proximal portion of the gastrointestinal tract. BMPs interact with specific receptors on the cell surface, referred to as bone morphogenetic protein receptors (BMPRs). Signal transduction through BMPRs results in mobilization of members of the SMAD family of proteins, which in turn modulate transcription of target genes. Of particular interest in the present invention are modulators, i.e. activators and inhibitors, of BMP signaling, which can readily be identified by one of ordinary skill in the art by any of a number of methods, for example competitive binding assays for binding to BMP or BMP receptors, functional assays, e.g. measuring enhancement/suppression of activity of downstream signaling proteins such as relocalization of SMADs to the nucleus and transcriptional activation of downstream gene targets as known in the art, and/or changes to cellular activity or lack thereof such as changes to proliferation potential and the ability to differentiate in the presence of the activator or inhibitor, respectively etc., as well known in the art.

By "transforming growth factor betas", "TGF-βs", and "TGFBs" it is meant the TGFB secreted proteins belonging to the subfamily of the transforming growth factor β (TGFβ) superfamily. TGFBs (TGFB1, TGFB2, TGFB3) are multifunctional peptides that regulate proliferation, differentiation, adhesion, and migration and in many cell types. The mature peptides may be found as homodimers or as heterodimers with other TGFB family members. TGFBs interact with transforming growth factor beta receptors (TGF-βRs, or TGFBRs) on the cell surface, which binding activates MAP kinase-, Akt-, Rho- and Rac/cdc42-directed signal transduction pathways, the reorganization of the cellular architecture and nuclear localization of SMAD proteins, and the modulation of target gene transcription. Of particular interest in the present invention are modulators, i.e. activators and inhibitors, of TGFB signaling, which can be readily be identified by one of ordinary skill in the art by any of a number of methods, for example competitive binding assays for binding to TGFB or TGFB receptors, or functional assays, e.g. measuring enhancement/suppression of activity of downstream signaling proteins such as MAPK, Akt, Rho, Rac, and SMADs and/or cellular activation or lack thereof such as changes in proliferation potential, adhesive properties, and migration states in the presence of the activator or inhibitor, respectively, etc., as well known in the art.

By "Wnts" it is meant the family of highly conserved secreted signaling molecules which play key roles in both embryogenesis and mature tissues. The human Wnt gene family has at least 19 members (Wnt-1, Wnt-2, Wnt-2B/Wnt-13, Wnt-3, Wnt3a, Wnt-4, Wnt-5A, Wnt-5B, Wnt-6, Wnt-7A, Wnt-7B, Wnt-8A, Wnt-8B, Wnt-9A/Wnt-14, Wnt-9B/Wnt-15, Wnt-10A, Wnt-10B, Wnt-11, Wnt-16). Wnt proteins modulate cell activity by binding to Wnt receptor complexes that include a polypeptide from the Frizzled (Fz) family of proteins and a polypeptide of the low-density lipoprotein receptor (LDLR)-related protein (LRP) family of proteins. Once activated by Wnt binding, the Wnt receptor complex will activate one or more intracellular signaling cascades. These include the canonical Wnt signaling pathway; the Wnt/planar cell polarity (Wnt/PCP) pathway; and the Wnt-calcium (Wnt/Ca$^{2+}$) pathway (Giles, R H et al. (2003) Biochim Biophys Acta 1653, 1-24; Peifer, M. et al. (1994) Development 120: 369-380; Papkoff, J. et al (1996) Mol. Cell. Biol. 16: 2128-2134; Veeman, M. T. et al. (2003) Dev. Cell 5: 367-377). For example, activation of the canonical Wnt signaling pathway results in the inhibition of phosphorylation of the intracellular protein β-catenin by GSK-3b, leading to an accumulation of β-catenin in the cytosol and its subsequent translocation to the nucleus where it interacts with transcription factors, e.g. TCF/LEF, to activate target genes. Of particular interest in the present invention are modulators, i.e. activators and inhibitors of Wnt signaling, which can readily be identified by one of ordinary skill in the art by any of a number of methods, for example, competitive binding assays for binding to Wnt or Wnt receptors, or functional assays, e.g. measuring enhancement/suppression of activity of downstream signaling proteins such as β-catenin and TCF/LEF and/or cellular activation or lack thereof in the presence of the activator or inhibitor, respectively etc., as described above and as well known in the art.

By "ectoderm rostralizing factors" it is meant growth factors that promote the rostralization of ectoderm, i.e. the formation of rostral ectoderm from ectoderm. Rostralizing factors include IGF1 and insulin.

By culturing under "non-adherent conditions" it is meant culturing under conditions that suppress the adhesion of cells to the vessel in which they are cultured, e.g. the bottom of a tissue culture plate or flask. In some instances, the cells are naturally non-adherent, i.e. they will not adhere to a surface unless the surface is coated with a matrix composition, e.g. fibronectin, laminin, poly-ornithin, poly-lysine, collagen IV, MATRIGEL™, and polycarbonate membranes. In some instances, cells may be maintained in a non-adherent state by agitating the culture.

By culturing under "adherent conditions" it is meant culturing under conditions that promote the adhesion of cells to the vessel in which they are cultured, e.g. the bottom of a tissue culture plate or flask. In some instances, cells may be induced to adhere to the vessel simply by keeping the culture stationary. In some instances, the wall of the vessel to which it is desirable to promote adhesion may be coated with a composition to which the cells may adhere, e.g. fibronectin, laminin, poly-ornithin, poly-lysine, collagen IV, MATRIGEL™, and polycarbonate membranes.

By "efficiency of differentiation" or "differentiation efficiency" it is meant the efficiency with which a cell or culture of cells is induced to differentiate. Cells which demonstrate an enhanced efficiency of differentiation in, e.g. the presence of an agent, and/or under certain culture conditions, will demonstrate an enhanced ability to give rise to a particular cell or population of cells when contacted with that agent or grown under those culture conditions relative to cells that were not contacted with that agent or grown under those culture conditions. By enhanced, it is meant that the cell cultures have the ability to give rise to that particular cell or population of cells that is at least about 50%, about 100%, about 200%, about 300%, about 400%, about 600%, about 1000%, about 2000%, at least about 5000% of the ability of the cell culture that was not contacted with the agent. In other words, the cell culture produces about 1.5-fold, about 2-fold, about 3-fold, about 4-fold, about 6-fold, about 10-fold, about 20-fold, about 30-fold, about 50-fold, about 100-fold, about 200-fold more cells that are that particular cell or population of cells than that are produced by a population of cells that are not contacted with the agent.

The terms "treatment", "treating" and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease in a mammal, and includes: (a) preventing the disease from occurring in a subject which may be predisposed to the disease but has not yet been diagnosed as having it; (b) inhibiting the disease, i.e., arresting its development; or (c) relieving the disease, i.e., causing regression of the disease. The therapeutic agent may be administered before, during or after the onset of disease or injury. The treatment of ongoing disease, where the treatment stabilizes or reduces the undesirable clinical symptoms of the patient, is of particular interest. Such treatment is desirably performed prior to complete loss of function in the affected tissues. The subject therapy will desirably be administered during the symptomatic stage of the disease, and in some cases after the symptomatic stage of the disease.

The terms "individual," "subject," "host," and "patient," are used interchangeably herein and refer to any mammalian subject for whom diagnosis, treatment, or therapy is desired, particularly humans.

General methods in molecular and cellular biochemistry can be found in such standard textbooks as Molecular Cloning: A Laboratory Manual, 3rd Ed. (Sambrook et al., HaRBor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference. Reagents, cloning vectors, and kits for genetic manipulation referred to in this disclosure are available from commercial vendors such as BioRad, Stratagene, Invitrogen, Sigma-Aldrich, and ClonTech. Diagrams and descriptions of the cochlea and of the organs of the vestibular system are found in Grey's Anatomy of the Human Body.

Methods of Generating Inner Ear Cells In Vitro

Methods and compositions for generating cells of the inner ear in vitro are provided. By "inner ear", it is meant the innermost part of the vertebrate ear, more particularly the tissues associated with the auditory and vestibular systems. Examples of cells of the inner ear include sensory hair cells and supporting cells. Sensory hair cells are mechanosensory cells resemble columnar cells, each with a hair bundle of steriocilia at the apical surface. They are electrically active cells, and show a graded electrical response when depolarized. Supporting cells are the cells that contribute to the complex structural and functional properties of the cochlea and vestibular tissues.

Sensory hair cells and supporting cells may be identified by their structural and/or functional characteristics. For example, hair cells express detectable levels of one or more of the genes atonal homolog 1 (HATH1), myosin VI (MYO6), myosin VIIA (MYO7A), Espin (ESPN), sacsin (SACS), myosin heavy chain 3 (MYH2), cadherin23 (CDH23), protocadherin15 (PCDH15), otoferlin (OTOF), and prestin (SLC26A5). In other words, the sensory hair cells are "positive" for one or more of these biochemical markers. Supporting cells express detectable levels of one or more of biochemical markers cyclin-dependent kinase inhibitor 1B (CDKN1B, p27 (KIP1)), prospero homeobox 1 (PROX1), otoancorin (OTOA), musashi homolog 1 (MSI1), SRY-box 2 (SOX2), gap junction protein beta 2, 26 kDa (Connexin 26), gap junction protein beta 6, 30 kDa (Connexin30), gap junction protein alpha 1, 43 kDa (Connexin43), and hairy/enhancer-of-split related with YRPW motif 2 (HEY2). In other words, the supporting cells are "positive" for one or more of these biochemical markers. It will be understood by those of skill in the art that the stated expression levels reflect detectable amounts of the marker protein or the RNA encoding that protein. A cell that is negative for staining, i.e. a cell in which the level of binding of a marker specific reagent is not detectably different from an isotype matched control, may still express minor amounts of the marker. And while it is commonplace in the art to refer to cells as "positive" or "negative" for a particular marker, actual expression levels are a quantitative trait. The number of molecules expressed by the cell can vary by several logs, yet still be characterized as "positive". The staining intensity of cells can be monitored by measuring protein levels, e.g., by immunohistochemistry, flow cytometry, etc., or by measuring RNA levels, e.g., by RT-PCR, Northern blot, in situ hybridization, etc. Although the absolute level of staining may differ with a particular fluorochrome and reagent preparation, the data can be normalized to a control.

In methods of the invention, inner ear cells are generated from a population of cells that are enriched for otic progenitor cells. Otic progenitor cells are proliferating cells that can differentiate to give rise to inner ear sensory hair cells and supporting cells. By an "enriched" population of otic progenitors, it is meant that 5% or more of the cells in the population are otic progenitor cells, i.e. 5% or more, 10% or more, 15% or more, 20% or more, or 25% or more of the cells of the population are of a given cell type, i.e. otic progenitor cells; in some instances, 30% or more, 35% or more, 40%, or more or 45% or more of the cells are of the given cell type; sometimes about 50% or more, 55% or more, or 60% or more of the cells may be of the given cell type. In some embodiments, the enriched cell population will be a substantially pure population, where by "substantially pure" it is meant having about 70% or more, 75% or more, or 80% or more of the population be otic progenitor cells, more usually about 85% or more or 90% or more of the population, and sometimes at least 95% or more of the population, e.g. 95%, 98%, and up to 100% of the population.

A population comprising otic progenitor cells may be enriched for otic progenitor cells by culturing methods. In such cases, a population of cells, e.g. pluripotent stem cells or preplacodal ectodermal cells, is growth under culture conditions such as those described below that promote the formation of otic progenitor cells. Additionally or alternatively, otic progenitor cells may be enriched mechanically. In such cases, the otic progenitor cells are selected from a heterogenous population of cells, e.g. a heterogenous population of cells derived from a tissue biopsy, or a heterogeneous population of cells derived by culturing pluripotent stem cells, to form an enriched population of otic progenitor cells. Methods of enriching for otic progenitor cells will be discussed first, after which will follow a discussion of methods of generating inner ear cells in vitro from enriched populations of otic progenitor cells, kits for use in these methods, and uses for inner ear cells generated by these methods.

Enrichment of Otic Progenitor Cells by Culturing

In some embodiments, an enriched population of otic progenitor cells is arrived at by culturing methods. For example, otic progenitor cells may be cultured from preplacodal ectoderm cells or from pluripotent stem cells under conditions that promote the formation of otic progenitor cells. A demonstrated in the examples section below, preplacodal cells can be induced to form otic progenitor cells by culturing as adherent cultures in the presence of one or more growth factors of the fibroblast growth factor (FGF) family, e.g. FGF1, FGF2, FGF3, FGF4, FGF5, FGF6, FGF7, FGF8, FGF9, FGF10, preferably FGF2 (bFGF) or combinations of FGF3, FGF8, and FGF10. Culturing preplacodal ectodermal cells under these conditions for about 6 days, e.g. 4 or 5 days, more usually 6 days, sometimes as much as 7, 8, or 9 days at 37 C will generate otic progenitor cells.

In some instances, an inhibitor of BMP signaling is provided during the first days of incubation with FGFs, i.e. the "induction" phase of otic progenitor cell differentiation. Inhibitors of BMP, also referred to herein as "BMP inhibitors", antagonize signaling by bone morphogenic proteins (BMPs), usually by binding to BMPs or BMP receptors (BMPRs) and blocking BMP-BMPR interaction. Inhibitors of BMP signaling can readily be identified by one of ordinary skill in the art, as discussed in greater detail above. Naturally occurring inhibitors of BMP signaling include, without limitation, noggin, chordin, follistatin, sclerostin, CTGF, and gremlin. Other inhibitors of BMP signaling include small molecule inhibitors, e.g. dorsomorphin, LDN-193189, etc., and antagonistic antibodies, i.e. antibodies that prevent binding of BMPs to BMPRs.

Additionally or alternatively, activators of Wnt may be provided during the induction phase of otic progenitor cell differentiation. Activators of Wnt signaling, also referred to herein as "Wnt activators" promote the activity of signaling pathways that are activated by Wnt proteins. Activators of Wnt signaling may promote the activity of these pathways by binding to and activating Wnt receptors. For example, any of the Wnt proteins or soluble activating domaina thereof may serve as Wnt activators, as can Roof plate-specific Spondin 1 (RSpondin1, or RSPO1), a natural enhancer of the canonical Wnt pathway that binds to LRP6. Alternatively, activators of Wnt signaling may promote the activity of these pathways by modulating the activity of signal transduction proteins that modulate Wnt signaling, e.g. GSK3-$\beta$, $\beta$-catenin, etc., e.g. the small molecule inhibitors 603281-31-8, SB-216763, and SB-415286. Activators of Wnt signaling can readily be identified by one of ordinary skill in the art by methods described above and known in the art.

In some instances, fibroblast growth factor 19 (FGF19), a high affinity, heparin-dependent ligand for fibroblast growth factor receptor 4 (FGFR4), is provided in addition to the other FGFs.

If an inhibitor of BMP signaling, an activator of Wnt signaling and/or FGF19 are provided, the preplacodal cells are usually contacted with these factors during the first about 3 days, e.g. days 1, 2, and 3, and sometimes day 4, and even day 5 of culturing with FGFs. The factor(s) are usually provided as polypeptides at physiological concentrations as described in the art and in the examples below, in any suitable media for culturing embryoid body-derived cells, e.g. DMEM or DMEM/F12 supplemented with N2, B27, and/or other synthetic supplement and ampicillin.

In some embodiments, an activator of BMP is provided later during the incubation period with FGFs, i.e. during the "stabilization" phase of otic progenitor cell differentiation. By "later in the incubation period" it is meant in the final about 3 days of incubation with FGFs, e.g. during the last day, during the penultimate day, and in some instances during the $3^{rd}$ or $4^{th}$ to-final day of incubation with FGFs. Activators of BMP signaling promote the activity of signaling pathways that are activated by BMPs. For example, any BMP may be employed as an activator of BMP signaling. Activators of BMP signaling are typically not provided simultaneously with inhibitors of BMP signaling or activators of Wnt signaling; if BMP inhibitors and/or Wnt activators are used, their use is halted when the activators of BMP signaling is added.

Preplacodal ectodermal cells that may be used in this culturing step may be from any available source. For example, they may be from embryonic tissue, e.g. anterior ectoderm tissue from a 4-5 somite-staged embryo that has been dissociated by enzymatic or manual treatment, etc. Alternatively, preplacodal ectodermal cells may be derived in vitro, for example by culturing pluripotent stem cells under conditions that promote the formation of embryoid bodies (EBs) comprising preplacodal ectodermal cells. If derived in vitro, any method in the art that promotes the formation of EBs in vitro comprising preplacodal ectodermal cells that are responsive to cues to become otic progenitors may be used. For example, pluripotent stem cells may be cultured for 10 days in the presence of EGF and IGF-1 (Li et al. (2003) PNAS 100(23): 13495-13500). As another example and as demonstrated below, preplacodal ectodermal cells may be cultured from pluripotent stem cells by culturing pluripotent stem cells in the presence of one or more factors that suppresses the formation of endoderm and mesoderm, and one or more ectoderm rostralizing factors.

Factors that suppress the formation of endoderm and mesoderm include, without limitation, inhibitors of Wnt signaling and inhibitors of TGFB signaling. Inhibitors of Wnt signaling, also referred to herein as "Wnt inhibitors" are agents that antagonize signaling by Wnts, either by binding to Wnts or Wnt receptors and blocking Wnt-Wnt receptor interaction or by modulating intracellular signaling activity downstream of Wnt binding, e.g. by stabilizing β-catenin. Naturally occurring factors that inhibit Wnt signaling include, without limitation, the Dickkopf proteins (DKK-1 to -4), secreted Frizzled-related proteins (sFRP-1 to -5), Wnt Inhibitory Factor1 (WIF1), adenomatosis polyposis down-regulated 1 (APCDD1), and Soggy/DKKL1. Other inhibitors of Wnt signaling include Frizzled-Fc fusion proteins, e.g. Frizzled 8-Fc (Fz8-Fc), antibodies specific for Wnts or Wnt receptors, small molecule compounds such as pyrvinium, IWP2, and those that are readily identifiable by methods described above. Inhibitors of TGFB signaling, also referred to herein as "TGFB inhibitors" antagonize signaling by TGFBs, either by binding to TGFBs or TGFB receptors (TGFBRs) and blocking TGFB/TGFBR interaction or by inhibiting the activation of one or more of the intracellular signaling molecules that are activated by TGFB/TGFBR interaction. Examples include antibodies specific for TGFBs or TGFBRs, small molecule inhibitors such as SIS3, a specific inhibitor of TGFB1/ALK5 phosphorylation of SMAD3, and those that are readily identifiable by methods described above.

In presently disclosed methods, pluripotent stem cells are cultured in the presence of at least one factor that suppresses the formation of endoderm and mesoderm. Any factor that suppresses the formation of endoderm and mesoderm as known in the art may be used. In some embodiments, that factor is selected from an inhibitor of Wnt signaling and an inhibitor of TGFB signaling. In some embodiments stem cells are cultured in the presence of at least two factors that suppress the formation of endodermal and mesodermal cells. In some such embodiments, the at least two factors include at least inhibitor of Wnt signaling and at least one inhibitor of TGFB signaling.

Ectoderm rostralizing factors are growth factors that promote the formation of rostral ectoderm from ectoderm. Examples of rostralizing factors include factors that activate Insulin-like growth factor (IGF) signaling. Examples of such factors include IGF1 and insulin.

Stem cells cultured for about 5-20 days, e.g. about 8-18 days, sometimes 10-15 days, e.g. 15 days, in the presence of at least one factor that suppresses the formation of endoderm and mesoderm and at least one ectoderm rostralizing factor will form an enriched population of preplacodal ectodermal cells. Any other culture conditions known in the art to generate preplacodal ectodermal cells from pluripotent stem cells may also be employed. In some embodiments, the pluripotent stem cells are cultured under non-adherent conditions. In other embodiments, the pluripotent stem cells are cultured under adherent conditions. In some embodiments, the factors are provided in a media of constant knockout serum replacement (KSR) concentration, e.g. 5% KSR, 10% KSR, 15% KSR, or 20% KSR. In other embodiments, the factors are provided in several medias provided sequentially over time, e.g. a first media, a second media, a third media, and so on, wherein the first media comprising a high concentration of KSR (e.g. 18-25%, e.g. 20% KSR), the second media comprises an intermediate concentration of KSR (e.g. 13-17% KSR, e.g. 15%), the third media comprises a lower concentration of KSR (e.g. 5-12% KSR, e.g. 10%), etc.

In some embodiments, the preplacodal ectodermal cells are mechanically enriched prior to culturing. In other words, the preplacodal ectodermal cells are selected from an initial complex mixture or heterogenous population of cells to form a population that is enriched for preplacodal ectodermal cells, which is then cultured under conditions that will promote the formation of otic progenitor cells. The initial population of cells may be a mixture of cells derived from tissue, for example from tissue comprising anterior ectoderm from a 4-5 somite-staged embryo that has been dissociated and dispersed by enzymatic treatment, trituration, etc. into an appropriate buffer, or it may be a mixture of cells that is already enriched for preplacodal ectodermal cells, e.g. by culture methods that direct the formation of preplacodal ectodermal cells from pluripotent stem cells as, e.g., described above, and suspended in that buffer. Such solution will generally be a balanced salt solution, e.g. normal saline, PBS, Hank's balanced salt solution, etc., conveniently supplemented with fetal calf serum or other naturally occurring factors, in conjunction with an acceptable buffer at low concentration, generally from 5-25 mM. Convenient buffers include HEPES, phosphate buffers, lactate buffers, etc. Preplacodal ectodermal cells are selected from such preparations by general selection methods known in the art and described in greater detail below, using affinity reagent that specifically recognizes and selectively binds a cells surface marker associated with preplacodal ectodermal cells, e.g. fibroblast growth factor receptor 1 (FGFR1), fibroblast growth factor receptor 2 (FGFR2), fibroblast growth factor receptor 3 (FGFR3), SIX homeobox 1 (SIX1), SIX homeobox 4 (SIX4), eyes absent homolog 1 (EYA1), eyes absent homolog 2 (EYA2), etc., as known in the art.

The population of enriched preplacodal ectodermal cells is then cultured by the methods described above to arrive an enriched population of otic progenitor cells.

Enrichment of Otic Progenitor Cells by Mechanical Selection

In embodiments in which the otic progenitor cells are enriched mechanically, the otic progenitor cells are selected from a complex mixture or heterogenous population of cells to form a population that is enriched for otic progenitor cells, which is then cultured under conditions that will promote the formation of inner ear cells. The initial population of cells may be a mixture of cells derived from tissue, for example epithelial tissue from cochlear sensory epithelium and/or vestibular tissues that has been dissociated and dispersed by enzymatic treatment, trituration, etc. into an appropriate buffer solution (see, e.g. Diensthuber et al. (2009) JARO 10:173-190), or a mixture of cells that is already enriched for otic progenitor cells, e.g. by culture methods that direct the formation of otic progenitor cells from preplacodal ectodermal cells or from pluripotent stem cells as, e.g., described above, and suspended in buffer. Such solution will generally be a balanced salt solution, e.g. normal saline, PBS, Hank's balanced salt solution, etc., conveniently supplemented with fetal calf serum or other naturally occurring factors, in conjunction with an acceptable buffer at low concentration, generally from 5-25 mM. Convenient buffers include HEPES, phosphate buffers, lactate buffers, etc.

Otic progenitor cells may be separated from the initial population immediately following dispersion or suspension of the cells. Alternatively, the initial population of cells is frozen and stored frozen, usually at about −80° C. to about liquid nitrogen temperature (−190° C.), until a time at which the separation of the otic progenitor cells from the subject initial population may be performed. In such cases, the cells are usually stored in 10% DMSO, 50% serum, 40% buffered medium, or some other such solution as is commonly used in the art to preserve cells at such temperatures, and will be thawed and recultured by methods commonly known in the art and as described further below.

Separation of the otic progenitor cells from the initial population of cells may be by any convenient separation technique. For example, the otic progenitor cells may be separated from the initial population by affinity separation techniques. Techniques for affinity separation may include magnetic separation using magnetic beads coated with an affinity reagent (magnetic-activated cell sorting, or MACS), affinity chromatography, "panning" with an affinity reagent attached to a solid matrix, e.g. plate, cytotoxic agents joined to an affinity reagent or used in conjunction with an affinity reagent, e.g. complement and cytotoxins, or other convenient technique. Techniques providing accurate separation include fluorescence activated cell sorters (FACS), which can have varying degrees of sophistication, such as multiple color channels, low angle and obtuse light scattering detecting channels, impedance channels, etc. The cells may be selected against dead cells by employing dyes associated with dead cells (e.g. propidium iodide). Any technique may be employed which is not unduly detrimental to the viability of the otic progenitor cells.

To separate the otic progenitor cells from the initial population by affinity separation techniques, the initial population of cells is contacted with affinity reagent that specifically recognizes and selectively binds a cells surface marker associated with otic progenitor cells, e.g. fibroblast growth factor receptor 1 (FGFR1), jagged 1 (JAG1), Delta1, Notch 1, etc. as known in the art. By "selectively bind" is meant that the molecule binds preferentially to the target of interest or binds with greater affinity to the target than to other molecules. For example, an antibody will bind to a molecule comprising an epitope for which it is specific and not to unrelated epitopes. In some embodiments, the affinity reagent may be an antibody, i.e. an antibody that is specific for a preplacodal ectodermal cell marker. In some embodiments, the affinity reagent may be a specific receptor or ligand for a preplacodal ectodermal cell marker, e.g. a peptide ligand and receptor; effector and receptor molecules, a T-cell receptor specific for a preplacodal ectodermal cell marker, and the like. In some embodiments, multiple affinity reagents specific for an otic progenitor cell marker may be used. In some embodiments, multiple affinity reagents, each specific for a different preplacodal ectodermal cell marker, may be used.

Antibodies and T cell receptors that find use as affinity reagents may be monoclonal or polyclonal, and may be produced by transgenic animals, immunized animals, immortalized human or animal B-cells, cells transfected with DNA vectors encoding the antibody or T cell receptor, etc. The details of the preparation of antibodies and their suitability for use as specific binding members are well-known to those skilled in the art. Of particular interest is the use of labeled antibodies as affinity reagents. Conveniently, these antibodies are conjugated with a label for use in separation. Labels include magnetic beads, which allow for direct separation; biotin, which can be removed with avidin or streptavidin bound to a support; fluorochromes, which can be used with a fluorescence activated cell sorter; or the like, to allow for ease of separation of the particular cell type. Fluorochromes that find use include phycobiliproteins, e.g. phycoerythrin and allophycocyanins, fluorescein and Texas red. Frequently each antibody is labeled with a different fluorochrome, to permit independent sorting for each marker.

The initial population of cells are contacted with the affinity reagent(s) and incubated for a period of time sufficient to bind the available cell surface antigens. The incubation will usually be at least about 5 minutes and usually less than about 60 minutes. It is desirable to have a sufficient concentration of antibodies in the reaction mixture, such that the efficiency of the separation is not limited by lack of antibody. The appropriate concentration is determined by titration, but will typically be a dilution of antibody into the volume of the cell suspension that is about 1:50 (i.e., 1 part antibody to 50 parts reaction volume), about 1:100, about 1:150, about 1:200, about 1:250, about 1:500, about 1:1000, about 1:2000, or about 1:5000. The medium in which the cells are suspended will be any medium that maintains the viability of the cells. A preferred medium is phosphate buffered saline containing from 0.1 to 0.5% BSA or 1-4% goat serum. Various media are commercially available and may be used according to the nature of the cells, including Dulbecco's Modified Eagle Medium (dMEM), Hank's Basic Salt Solution (HBSS), Dulbecco's phosphate buffered saline (dPBS), RPMI, Iscove's medium, PBS with 5 mM EDTA, etc., frequently supplemented with fetal calf serum, BSA, HSA, goat serum etc.

The cells in the contacted population that become labeled by the affinity reagent, i.e. the preplacodal ectodermal cells, are selected for by any convenient affinity separation technique, e.g. as described above or as known in the art. Following separation, the separated cells may be collected in any appropriate medium that maintains the viability of the cells, usually having a cushion of serum at the bottom of the collection tube. Various media are commercially available and may be used according to the nature of the cells, including dMEM, HBSS, dPBS, RPMI, Iscove's medium, etc., frequently supplemented with serum or artificial supplements.

In some embodiments, depletion steps may also be performed, in which affinity reagents that are specific for non-otic progenitor cells are used to select away, or "negatively select" cells that are not of interest.

Compositions that are substantially pure compositions of otic progenitor cells are usually achieved in this manner. In other words, the otic progenitor cells will be about 70%, about 75%, or about 80% of the cell composition, usually about 85% or about 90% or more of the cell composition, and may be as much as 95% or more of the cell composition, i.e. 95%, 97%, 99%, or even 100% of the cell composition.

The enriched population of otic progenitor cells may be used immediately to produce inner ear cells. Alternatively, the enriched population of otic progenitor cells may be frozen at liquid nitrogen temperatures and stored for long periods of time, being thawed and capable of being reused. In such cases, the cells will usually be frozen in 10% DMSO, 50% serum, 40% buffered medium, or some other such solution as is commonly used in the art to preserve cells at such freezing temperatures, and thawed in a manner as commonly known in the art for thawing frozen cultured cells.

Generation of Inner Ear Cells from Otic Progenitor Cells

To generate inner ear cells from an enriched population of otic progenitor cells, the otic progenitor cells are cultured under conditions that promote the differentiation of the otic progenitor cells into inner ear cells. The otic progenitor cells may be conveniently suspended in an appropriate nutrient medium, such as DMEM/F12, DMEM, or RPMI-1640, which may be supplemented with one or more of N2, B27, L-glutamine, antibiotics, e.g. penicillin and streptomycin, etc. In some embodiments, the medium does not include the use of growth factors, i.e., the otic progenitor cells are cultured in the absence of growth factors added to the culture. In some embodiments, the medium includes factors that promote the differentiation of inner ear cells. Typically, the conditions are adherent conditions, i.e. they promote the adherence of the otic progenitor cells to a matrix. In such cases, a matrix composition is provided to which the cells may adhere. Examples of matrix compositions to which cells may adhere include, without limitation, fibronectin, laminin, poly-ornithin, poly-lysine, collagen IV, MATRIGEL™, and polycarbonate membranes. In some embodiments, the matrix composition comprises MATRIGEL™. In certain embodiments, the matrix comprises MATRIGEL™ and a polycarbonate membrane.

In some embodiments, the culture conditions include co-culturing in the presence of feeder cells, e.g. stromal cells of the inner ear, e.g. utricle stromal cells. In other embodiments, the culture conditions do not include co-culturing with feeder cells, i.e. the otic progenitor cells are cultured in the absence of feeder cells. Mouse inner ear cells are typically cultured from otic progenitor cells in the presence of feeder cells. Human inner ear cells may be cultured from otic progenitor cells in the absence of feeder cells.

Otic progenitor cells are cultured under the above conditions for about 4 days, 5 days, or 6 days; more usually at least about 7 days, 8 days, or 9 days, sometimes for more than 10 days, e.g. 11 days 12 days, 14 days, 17 days, 21 days, or longer, to allow for the formation of inner ear cells. Inner ear cells generated in this way will form clusters comprising cells that express proteins expressed by hair cells and cells that express proteins expressed by supporting cells, which may be detected by any convenient method known in the art, e.g. immunohistochemistry, RT-PCR, and the like. Additionally, the cells in these clusters may begin to assume the morphology of hair cells or supporting cells, which may be visualized by commonly known microscopic techniques, e.g. epifluorescence microscopy, scanning electron microscopy, etc. Additionally, the cells in these clusters may begin to function like hair cells or supporting cells, e.g. showing a graded electrical response to stimulation, which may be assessed by measuring fluorescently conjugated gentamicin (GTTR) uptake or performing electrophysiological experiments.

In some instances, it may be desirable to increase the progenitor pool prior to inducing the differentiation of inner ear cells, e.g. to induce the production of more inner ear cells. In some such cases, the otic progenitor cell population may be expanded by culturing the cells in defined media comprising moderate levels of KSR, e.g. 8-13%, e.g. 10% KSR, under adherent conditions, and/or by contacting the otic progenitor cells with sonic hedgehog (SHH) or at least one FGF in nutrient medium. Expansion of the population may be for as long as desired by the artisan, for example, for about 2 days, for about 3 days, for about 4 days, for about 7 days, for about 14 days, for about 21 days, for about 1 month, for about 3 months or more.

Following the methods outline above, inner ear cells for any vertebrate may be generated. Usually, the inner ear cells are mammalian inner ear cells, e.g. human, primate, equine, bovine, porcine, canine, feline, rodent, etc. In some embodiments, the inner ear cells that are generated are mouse inner ear cells. In other embodiments, the inner ear cells that are generated are human inner ear cells. As discussed above, the generation of mouse inner ear cells from of otic progenitor cells typically requires co-culturing of the enriched population of otic progenitor cells with a population of stromal cells, whereas the generation of human inner ear cells does not.

Screening Methods

The methods described above provide a useful system for screening candidate agents for a desired activity, for example, to identify agents that are toxic to inner ear cells, to identify agents that will prevent against, mitigate, or reverse the toxicity of such agents, fto identify agents that will promote otoregeneration, etc., and to develope a better understanding the molecular basis of inner ear cell development and function. To that end, it has been shown that the methods of the invention provide for cultures comprising cells that resemble inner ear cells morphologically, biochemically and functionally. Accordingly, screening candidate agents for those that adversely impact the viability or function of these inner ear cells in vitro will identify agents that are toxic to inner ear cells in vivo and hence, that adversely affect hearing and/or balance. Similarly, screening candidate agents for those that prevent, mitigate or reverse the effects of those toxic agents on these inner ear cells in vitro or promote otoregeneration will identify agents that prevent, mitigate or reverse the effects of those toxic agent in vivo and promote the regeneration of inner ear cells. Likewise, screening agents that target known pathways for their effects on inner ear cell development, viability and function will provide a better understanding of the molecular basis of inner ear cell development and function.

In screening assays for biologically active agents, inner ear cells cultured by methods of the invention are contacted with a candidate agent of interest and the effect of the candidate agent is assessed by monitoring one or more output parameters. These output parameters may be reflective of an apoptotic state of the cells, such as amount of DNA fragmentation, the amount of cell blebbing, the amount of phosphatidylserine on the cell surface as visualized by Annexin V staining, and the like by methods that are well known in the art. Alternatively or additionally, the output parameters may be reflective of the viability of the culture, e.g. the number of cells in the culture, the rate of proliferation of the culture. Alternatively or additionally, the output parameters may be reflective of the function of the cells in the culture, e.g. electrophysiological properties of the cells. Alternatively or additionally, the output parameters may be reflective of the state of inner ear cell regeneration, e.g. the rate and extent of proliferation, the recurrence of hair cell phenotypes in the culture, etc.

Parameters are quantifiable components of cells, particularly components that can be accurately measured, desirably in a high throughput system. A parameter can be any cell component or cell product including cell surface determinant, receptor, protein or conformational or posttranslational modification thereof, lipid, carbohydrate, organic or inorganic molecule, nucleic acid, e.g. mRNA, DNA, etc. or a portion derived from such a cell component or combinations thereof. While most parameters will provide a quantitative readout, in some instances a semi-quantitative or qualitative result will be acceptable. Readouts may include a single determined value, or may include mean, median value or the variance, etc. Characteristically a range of parameter readout values will be obtained for each parameter from a multiplicity of the same assays. Variability is expected and a range of values for each of the set of test parameters will be obtained using standard statistical methods with a common statistical method used to provide single values.

Candidate agents of interest for screening include known and unknown compounds that encompass numerous chemical classes, primarily organic molecules, which may include organometallic molecules, inorganic molecules, genetic sequences, etc. An important aspect of the invention is to evaluate candidate drugs, including toxicity testing; and the like.

Candidate agents include organic molecules comprising functional groups necessary for structural interactions, particularly hydrogen bonding, and typically include at least an amine, carbonyl, hydroxyl or carboxyl group, frequently at least two of the functional chemical groups. The candidate agents often comprise cyclical carbon or heterocyclic structures and/or aromatic or polyaromatic structures substituted with one or more of the above functional groups. Candidate agents are also found among biomolecules, including peptides, polynucleotides, saccharides, fatty acids, steroids, purines, pyrimidines, derivatives, structural analogs or combinations thereof. Included are pharmacologically active drugs, genetically active molecules, etc. Compounds of interest include chemotherapeutic agents, hormones or hormone antagonists, etc. Exemplary of pharmaceutical agents suitable for this invention are those described in, "The Pharmacological Basis of Therapeutics," Goodman and Gilman, McGraw-Hill, New York, N.Y., (1996), Ninth edition. Also included are toxins, and biological and chemical warfare agents, for example see Somani, S. M. (Ed.), "Chemical Warfare Agents," Academic Press, New York, 1992).

Candidate agents of interest for screening also include nucleic acids, for example, nucleic acids that encode siRNA, shRNA, antisense molecules, or miRNA, or nucleic acids that encode polypeptides. Many vectors useful for transferring nucleic acids into target cells are available. The vectors may be maintained episomally, e.g. as plasmids, minicircle DNAs, virus-derived vectors such cytomegalovirus, adenovirus, etc., or they may be integrated into the target cell genome, through homologous recombination or random integration, e.g. retrovirus derived vectors such as MMLV, HIV-1, ALV, etc. Vectors may be provided directly to the subject cells. In other words, the pluripotent cells are contacted with vectors comprising the nucleic acid of interest such that the vectors are taken up by the cells.

Methods for contacting cells with nucleic acid vectors, such as electroporation, calcium chloride transfection, and lipofection, are well known in the art. Alternatively, the nucleic acid of interest may be provided to the subject cells via a virus. In other words, the pluripotent cells are contacted with viral particles comprising the nucleic acid of interest. Retroviruses, for example, lentiviruses, are particularly suitable to the method of the invention. Commonly used retroviral vectors are "defective", i.e. unable to produce viral proteins required for productive infection. Rather, replication of the vector requires growth in a packaging cell line. To generate viral particles comprising nucleic acids of interest, the retroviral nucleic acids comprising the nucleic acid are packaged into viral capsids by a packaging cell line. Different packaging cell lines provide a different envelope protein to be incorporated into the capsid, this envelope protein determining the specificity of the viral particle for the cells. Envelope proteins are of at least three types, ecotropic, amphotropic and xenotropic. Retroviruses packaged with ecotropic envelope protein, e.g. MMLV, are capable of infecting most murine and rat cell types, and are generated by using ecotropic packaging cell lines such as BOSC23 (Pear et al. (1993) P.N.A.S. 90:8392-8396). Retroviruses bearing amphotropic envelope protein, e.g. 4070A (Danos et al, supra.), are capable of infecting most mammalian cell types, including human, dog and mouse, and are generated by using amphotropic packaging cell lines such as PA12 (Miller et al. (1985) Mol. Cell. Biol. 5:431-437); PA317 (Miller et al. (1986) Mol. Cell. Biol. 6:2895-2902); GRIP (Danos et al. (1988) PNAS 85:6460-6464). Retroviruses packaged with xenotropic envelope protein, e.g. AKR env, are capable of infecting most mammalian cell types, except murine cells. The appropriate packaging cell line may be used to ensure that the subject CD33+ differentiated somatic cells are targeted by the packaged viral particles. Methods of introducing the retroviral vectors comprising the nucleic acid encoding the reprogramming factors into packaging cell lines and of collecting the viral particles that are generated by the packaging lines are well known in the art.

Vectors used for providing nucleic acid of interest to the subject cells will typically comprise suitable promoters for driving the expression, that is, transcriptional activation, of the nucleic acid of interest. This may include ubiquitously acting promoters, for example, the CMV-b-actin promoter, or inducible promoters, such as promoters that are active in particular cell populations or that respond to the presence of drugs such as tetracycline. By transcriptional activation, it is intended that transcription will be increased above basal levels in the target cell by at least about 10 fold, by at least about 100 fold, more usually by at least about 1000 fold. In addition, vectors used for providing reprogramming factors to the subject cells may include genes that must later be removed, e.g. using a recombinase system such as Cre/Lox, or the cells that express them destroyed, e.g. by including genes that allow selective toxicity such as herpesvirus TK, bcl-xs, etc Candidate agents of interest for screening also include polypeptides. Such polypeptides may optionally be fused to a polypeptide domain that increases solubility of the product. The domain may be linked to the polypeptide through a defined protease cleavage site, e.g. a TEV sequence, which is cleaved by TEV protease. The linker may also include one or more flexible sequences, e.g. from 1 to 10 glycine residues. In some embodiments, the cleavage of the fusion protein is performed in a buffer that maintains solubility of the product, e.g. in the presence of from 0.5 to 2 M urea, in the presence of polypeptides and/or polynucleotides that increase solubility, and the like. Domains of interest include endosomolytic domains, e.g. influenza HA domain; and other polypeptides that aid in production, e.g. IF2 domain, GST domain, GRPE domain, and the like. Additionally or alternatively, such polypeptides may be formulated for improved stability. For example, the peptides may be PEGylated, where the polyethyleneoxy group provides for enhanced lifetime in the blood stream. The polypeptide may be fused to another polypeptide to provide for added functionality, e.g. to increase the in vivo stability. Generally such fusion partners are a stable plasma protein, which may, for example, extend the in vivo plasma half-life of the polypeptide when present as a fusion, in particular wherein such a stable plasma protein is an immunoglobulin constant domain. In most cases where the stable plasma protein is normally found in a multimeric form, e.g., immunoglobulins or lipoproteins, in which the same or different polypeptide chains are normally disulfide and/or non-covalently bound to form an assembled multichain polypeptide, the fusions herein containing the polypeptide also will be produced and employed as a multimer having substantially the same structure as the stable plasma protein precursor. These multimers will be homogeneous with respect to the polypeptide agent they comprise, or they may contain more than one polypeptide agent.

The candidate polypeptide agent may be produced from eukaryotic cells, or may be produced by prokaryotic cells. It may be further processed by unfolding, e.g. heat denaturation, DTT reduction, etc. and may be further refolded, using methods known in the art. Modifications of interest that do not alter primary sequence include chemical derivatization of polypeptides, e.g., acylation, acetylation, carboxylation, amidation, etc. Also included are modifications of glycosylation, e.g. those made by modifying the glycosylation patterns of a polypeptide during its synthesis and processing or in further processing steps; e.g. by exposing the polypeptide to enzymes which affect glycosylation, such as mammalian glycosylating or deglycosylating enzymes. Also embraced are sequences that have phosphorylated amino acid residues, e.g. phosphotyrosine, phosphoserine, or phosphothreonine. The polypeptides may have been modified using ordinary molecular biological techniques and synthetic chemistry so as to improve their resistance to proteolytic degradation or to optimize solubility properties or to render them more suitable as a therapeutic agent. Analogs of such polypeptides include those containing residues other than naturally occurring L-amino acids, e.g. D-amino acids or non-naturally occurring synthetic amino acids. D-amino acids may be substituted for some or all of the amino acid residues.

The candidate polypeptide agent may be prepared by in vitro synthesis, using conventional methods as known in the art. Various commercial synthetic apparatuses are available, for example, automated synthesizers by Applied Biosystems, Inc., Beckman, etc. By using synthesizers, naturally occurring amino acids may be substituted with unnatural amino acids. The particular sequence and the manner of preparation will be determined by convenience, economics, purity required, and the like. Alternatively, the candidate polypeptide agent may be isolated and purified in accordance with conventional methods of recombinant synthesis. A lysate may be prepared of the expression host and the lysate purified using HPLC, exclusion chromatography, gel electrophoresis, affinity chromatography, or other purification technique. For the most part, the compositions which are used will comprise at least 20% by weight of the desired product, more usually at least about 75% by weight, preferably at least about 95% by weight, and for therapeutic purposes, usually at least about 99.5% by weight, in relation to contaminants related to the method of preparation of the product and its purification. Usually, the percentages will be based upon total protein.

In some cases, the candidate polypeptide agents to be screened are antibodies. The term "antibody" or "antibody moiety" is intended to include any polypeptide chain-containing molecular structure with a specific shape that fits to and recognizes an epitope, where one or more non-covalent binding interactions stabilize the complex between the molecular structure and the epitope. The specific or selective fit of a given structure and its specific epitope is sometimes referred to as a "lock and key" fit. The archetypal antibody molecule is the immunoglobulin, and all types of immunoglobulins, IgG, IgM, IgA, IgE, IgD, etc., from all sources, e.g. human, rodent, rabbit, cow, sheep, pig, dog, other mammal, chicken, other avians, etc., are considered to be "antibodies." Antibodies utilized in the present invention may be either polyclonal antibodies or monoclonal antibodies. Antibodies are typically provided in the media in which the cells are cultured.

Candidate agents may be obtained from a wide variety of sources including libraries of synthetic or natural compounds. For example, numerous means are available for random and directed synthesis of a wide variety of organic compounds, including biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Candidate agents are screened for biological activity by adding the agent to at least one and usually a plurality of cell samples, sometimes in conjunction with cells lacking the agent. The change in parameters in response to the agent is measured, and the result evaluated by comparison to reference cultures, e.g. in the presence and absence of the agent, obtained with other agents, etc.

In instances in which a screen is being performed to identify candidate agents that will prevent, mitigate or reverse the effects of a toxic agent or to identify candidate agents with the ability to promote the regeneration of inner ear cells, the screen is typically performed in the presence of the toxic agent. In cases in which the protective/preventative ability of the candidate agent is tested, the candidate agent may be added before the toxic agent, simultaneously with the candidate agent, or subsequent to treatment with the candidate agent. In cases in which the regenerative ability of the candidate agent is tested, the toxic agent is added either before treatment with the candidate agent or simultaneously with the candidate agent. The toxic agent may be an agent known in the art to be toxic to inner ear cells, e.g. an anticancer drug such as cisplatin or an aminoglycoside, e.g. gentamicin; or it may be a toxic agent identified using the methods described herein. A control sample of cells lacking the toxic agent may also be included.

The agents are conveniently added in solution, or readily soluble form, to the medium of cells in culture. The agents may be added in a flow-through system, as a stream, intermittent or continuous, or alternatively, adding a bolus of the compound, singly or incrementally, to an otherwise static solution. In a flow-through system, two fluids are used, where one is a physiologically neutral solution, and the other is the same solution with the test compound added. The first fluid is passed over the cells, followed by the second. In a single solution method, a bolus of the test compound is added to the volume of medium surrounding the cells. The overall concentrations of the components of the culture medium should not change significantly with the addition of the bolus, or between the two solutions in a flow through method.

A plurality of assays may be run in parallel with different agent concentrations to obtain a differential response to the various concentrations. As known in the art, determining the effective concentration of an agent typically uses a range of concentrations resulting from 1:10, or other log scale, dilutions. The concentrations may be further refined with a second series of dilutions, if necessary. Typically, one of these concentrations serves as a negative control, i.e. at zero concentration or below the level of detection of the agent or at or below the concentration of agent that does not give a detectable change in the phenotype.

An analysis of the response of cells to the candidate agent may be performed at any time following treatment with the agent. For example, the cells may be analyzed 1, 2, or 3 days, sometimes 4, 5, or 6 days, sometimes 8, 9, or 10 days, sometimes 14 days, sometimes 21 days, sometimes 28 days, sometimes 1 month or more after contact with the candidate agent, e.g. 2 months, 4 months, 6 months or more In some embodiments, the analysis comprises analysis at multiple time points. The selection of the time point(s) for analysis will be based upon the type of analysis to be performed, as will be readily understood by the ordinarily skilled artisan.

The analysis may comprise measuring any of the parameters described herein or known in the art for measuring cell viability, cell proliferation, cell identity, cell morphology, and cell function, particularly as they may pertain to inner ear cells. For example, terminal deoxynucleotidyl transferase dUTP nick end labeling (TUNEL) may be employed to measure DNA fragmentation, or immunohistochemistry may be employed to detect Annexin V binding to phosphatidylserine on the cell surface. Electron microscopy and immunohistochemistry for proteins labeling cytoskeletal structures, e.g. Cadherin 23, F-actin, or Tubulin, may be employed to assess the morphology of the cells. Whole cell patch clamping may be employed to assay the electrophysiological properties of the cells. EdU or BrdU incorporation may be used to assay cell proliferation. Histochemistry, e.g. immunohistochemistry, for markers for inner ear hair cells and supporting as described above may be used to determine the extent of regrowth of inner ear cells. Such methods are well known to one of ordinary skill in the art.

Reagents, Devices and Kits

Also provided are reagents, devices and kits thereof for practicing one or more of the above-described methods. The subject reagents, devices and kits thereof may vary greatly.

In some embodiments, the reagents or kits will comprise one or more agents for use in the methods described. For example, the kit may comprise one or more of an inhibitor of Wnt signaling, e.g. DKK1; an inhibitor of TGFB signaling, e.g. SIS3; an ectoderm rostralizing factor, e.g. IGF-1; one or more FGFs, e.g. bFGF, or FGF3 and FGF10; an inhibitor of BMP signaling, e.g. noggin; an activator of Wnt signaling, e.g. R-Spondin1; an activator of BMP signaling, e.g. BMP4; FGF19; and/or SHH. In some embodiments, pluripotent stem cells may be provided, e.g. a vial of embryonic stem cells. In some embodiments, reprogramming factors may be provided for the reprogramming of somatic cells into induced pluripotent stem cells, as described in, for example, Application Nos. US20090047263, US20090068742, US20090191159, US20090227032, US20090246875, and US20090304646. Other reagents include reagents for the identification of pre-placodal ectodermal cells, otic progenitor cells, or inner ear cells, e.g. one or more antibodies that are specific for markers expressed by these cells as described above. Other reagents may include culture media, culture supplements, matrix compositions, and the like.

In addition to the above components, the subject kits will further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Materials and Methods

Cells and Culture.

ESCs were isolated from blastocysts, and iPSCs were generated from fibroblasts of Math1/nGFP mice (Lumpkin et al., 2003).

ES Cell Derivation.

Blastocysts were collected from superovulated homozygote Math1/nGFP females mated with homozygote Math1/nGFP males. Removal of the zona pellucidae of the blastocysts was aided by brief exposure to acidic Tyrode's solution, and the denuded blastocysts were individually transferred onto mitotically inactivated MEF feeder cells in 96-well plates in ES cell medium consisting of Knockout D-MEM (Invitrogen) supplemented with 15% ES cell-qualified fetal bovine serum (FBS) (Omega Scientific, Inc), 0.1 mM MEM non-essential amino acids (Invitrogen), 55 mM 2-mercaptoethanol (Invitrogen), 2 mM L-glutamine (Invitrogen), 50 mg/ml ampicillin and 1000 U LIF/ml (Rat ESGRO, Chemicon). MEFs were inactivated for three hours with 10 mg/ml mitomycin C (Sigma). After 7 days, the inner cell masses were dissociated with trypsin and plated on fresh MEF feeder cells. The resulting ES cell colonies were expanded and characterized by visual inspection for colony morphology, by RT-PCR analysis for expression on Nanog, Sox2, Oct4, and Gbx2, and by immunocytochemistry.

iPS Cell Generation.

MEFs were isolated from 12.5 day-old Math1/nGFP embryos and maintained in DMEM (Invitrogen) supplemented with 10% FBS. To generate ecotropic virus, Phoenix Eco cells (Orbigen) were transfected with pMX-Oct4, pMX-Sox2, pMX-Klf4, or pMX-cMyc (Addgene). Virus-containing media was collected at 2 days post transfection and filtrated using 0.45 mm cellulose acetate filters. $1 \times 10^6$ MEFs were infected with 20 ml of virus-containing media (5 ml of each virus) in presence of 8 mg/ml polybrene (Sigma). On the following day, the MEFs were washed 3× with PBS, trypsinized, and transferred onto mitotically inactivated MEF feeder cells and cultured in ES cell medium. Medium was refreshed every day for 3 weeks until primary iPS colonies were collected. Colonies with heterogeneous morphology were subcloned to obtain homogeneous colonies. The resulting iPS lines were characterized as described for ES lines.

Teratoma Assay.

$10^6$ ES or iPS cells were suspended in 100 ml of 40% DMEM, 10% FBS, and 50% MATRIGEL™ (BD Biosciences) and subcutaneously injected into the back of severe combined immunodeficient mice (SCID-beige, 8-week-old males, Charles River Laboratories), and kept under pathogen-free conditions. 4 weeks later, tumors were dissected, fixed over night with 4% paraformaldehyde in PBS, dehydrated in 30% sucrose solution, and embedded in OCT compound. Teratomas were then cryosectioned at a thickness of 12 mm, and stained with hematoxylin and eosin for histological examinations.

Embryoid Body Formation.

ES cell line C9 and iPS cell line #25-5 were used for all guidance experiments. MEF feeder cells were removed either by weaning the cells off for several passages or by pre-culturing the cells for 40 min allowing MEFs to attach. For embryoid body formation, the cells were dissociated with 0.25% trypsin-EDTA (Invitrogen) and cultured in poly(2-hydroxyethyl methacrylate)-coated 6-well cell suspension plates (Greiner). Coating was done by covering the plates with 1 ml of 2% poly(2 hydroxyethyl methacrylate) (Sigma) solution in 1:1 ethanol/acetone. After 2 min, the solution was completely aspirated and the plates were dried with open lid for 20 min in a cell culture cabinet. After three washes with PBS, the ES and iPS cells were added at a density of 50 cells/ml and cultured for 5 days in DMEM (Invitrogen) with 15% FBS, 0.1 mM MEM non-essential amino acids, 55 mM 2-mercaptoethanol, 2 mM L-glutamine and 50 mg/ml ampicillin. For otic induction experiments, the following growth factors or reagents were added to the medium: recombinant mouse Dickkopf related protein 1 (Dkk-1) at 100 ng/ml (R&D Systems), SIS3 at 3 mM (Sigma), and IGF1 at 10 ng/ml (Sigma). The following concentration ranges were tested to determine the optimal concentration of reagents: Dkk1 at 10-200 ng/ml, SIS3 at 1-10 mM and IGF1 at 1-100 ng/ml. Cells were incubated at 37 C in water saturated atmosphere with 5% $CO_2$. Half of the medium was replaced on the third day of incubation.

Otic Induction and Cell Differentiation.

Embryoid bodies were transferred into fibronectin-coated 4-well dishes (Greiner) at 30 embryoid bodies per well and cultured for three days in DMEM/F12 (Invitrogen, mixed 1:1) supplemented with N2 and B27 (Invitrogen), bFGF (R&D Systems, 25 ng/ml), heparin sulfate (Sigma, 50 ng/ml), and ampicillin (50 mg/ml). FGF3 (recombinant human FGF-3, R&D Systems) and FGF10 (recombinant human FGF-10, R&D Systems) were used at 25 ng/ml in parallel experiments. The FGF receptor antagonist SU5402 (a gift from Pfizer R&D) was used at 10 mM. After FGF-treatment, the cells were detached using 0.05% trypsin/EDTA (Sigma) in PBS, mildly triturated, and passed 1:10 into individual wells of 4-well dishes coated with either fibronectin, gelatin, MEFs, or mitotically inactivated embryonic (E18) chicken utricle stromal cells. Utricle stromal cells were prepared from 20 utricles whose sensory epithelia were removed after 40 min treatment with 0.5 mg/ml thermolysin (Sigma) in DMEM/F12 at 37 C. After addition of 5% serum, the sensory epithelia were removed and used in unrelated experiments. The 20 remaining pieces of stromal tissue were washed in PBS and transferred into a 150 ml drop of 0.125% trypsin/EDTA in PBS and incubated for 5 min at 37 C. After adding DMEM/F12 media supplemented with 10% FBS and 50 mg/ml ampicillin, the cells were gently triturated and cultured until 80%-90% confluency in a T75 flask. At the first passage, the cells were filtered through a 70 mm strainer (BD Falcon) to remove debris. Cells were further expanded twice before generating frozen stock at $1 \times 10^6$ cells per ml in DMEM/F12 with 20% FBS and 10% DMSO. After thawing and recovery of frozen stromal cells, they were plated into gelatin-coated 4-well dishes at 30,000 cells per ml and grown until 90% confluency. The cells were then mitotically inactivated with 2 mg/ml mitomycin C in DMEM/F12 with 5% FBS for 3 hr, washed 3x in media and then used for otic cell differentiation.

Marker Gene Expression Analysis.

Cells were cultured in 4-well tissue culture plates (Greiner 35/10), harvested by lysis in the dish for RNA isolation and RT-PCR, or fixed and subjected to immunocytochemical analysis.

For RT-PCR, total RNA was isolated using Absolutely RNA Miniprep kits (Stratagene). Reverse transcription was performed with Superscript III (Invitrogen). The resulting cDNAs were used as templates in polymerase chain reactions using the primer pairs listed in Table 1 (gene name, forward (F), (cDNA product length); gene name, reverse (R)).

TABLE 1

Primers used for RT-PCR.

| GENE NAME | SEQUENCE (5'-3') | SEQ ID NO. |
|---|---|---|
| Nanog F (398 bp) | CCTCCAGCAGATGCAAGAACT | 1 |
| Nanog R | AGTCCTCCCCGAAGTTATGGA | 2 |
| Sox2 F (384 bp) | ATGATGGAGACGGAGCTGAAG | 3 |
| Sox2 R | TCCGGGAAGCGTGTACTTATC | 4 |
| Oct3/4 F (313 bp) | GTTTCTGAAGTGCCCGAAGC | 5 |
| Oct3/4 R | CAGAGCAGTGACGGGAACAG | 6 |
| Gbx2 F (373 bp) | TGCCTGGTCAGACTGCTCATA | 7 |
| Gbx2 R | CGAATAGCGAACCTGCTAACG | 8 |
| Brachyury F (835 bp) | ATGCCAAAGAAAGAAACGAC | 9 |
| Brachyury R | AGAGGCTGTAGAACATGATT | 10 |
| GATA-6 F (334 bp) | ACCTTATGGCGTAGAAATGCTGAGGGTG | 11 |
| GATA-6 R | CTGAATACTTGAGGTCACTGTTCTCGGG | 12 |
| MAP2 F (262 bp) | CATCGCCAGCCTCGGAACAAACAG | 13 |
| MAP2 R | TGCGCAAATGGAACTGGAGGCAAC | 14 |
| Pax2 F (819 bp) | CAGCCTTTCCACCCAACG | 15 |
| Pax2 R | GTGGCGGTCATAGGCAGC | 16 |
| Pax8 F (313 bp) | CCACCCCTTCCTCTTTATCTAGC | 17 |
| Pax8 R | CAGGCCTCACTGTAGGAGGAATA | 18 |
| Dlx5 F (330 bp) | AACCCCTACCAGTACCAGTACCA | 19 |
| Dlx5 R | CTGTGTTTGCGTCAGTCCTAGAG | 20 |
| Six1 F (339 bp) | TAAGAACCGGAGGCAAAGAGAC | 21 |
| Six1 R | TAGGAACCCAAGTCCACCAAAC | 22 |
| Eya1 F (383 bp) | AAGTCACGTGGCCGAGGCAGAA | 23 |
| Eya1 R | TCCACACCACCTCGGACACCAGTT | 24 |
| Nat1 F (223 bp) | ATTCTTCGTTGTCAAGCCGCCAAAGTGGA | 25 |
| Nat1 R | AGTTGTTTGCTGCGGAGTTGTCATCTCGT | 26 |
| Gapdh F (442 bp) | AACGGGAAGCCCATCACC | 27 |
| Gapdh R | CAGCCTTGGCAGCACCAG | 28 |

All RT-PCR results presented were principally confirmed with at least two independent control experiments.

For immunocytochemistry, the cells were fixed with 4% paraformaldehyde in PBS for 15 min at room temperature. Nonspecific binding sites were blocked for 1 hr in 0.1% TRITON™ X-100, 1% bovine serum albumin, and 5% heat inactivated goat serum in PBS. The fixed cells were incubated overnight at 4° C. with diluted antibodies: 1:100 for monoclonal mouse antibody IgG2b to Oct-3/4 (Santa Cruz), 1:200 for polyclonal rabbit antibody to Nanog (Abcam), 1:200 for monoclonal mouse antibody IgG2b to Sox2 (Chemicon), 1:40 for polyclonal rabbit antibody to Brachyury (Santa Cruz), 1:40 for polyclonal rabbit antibody to GATA6 (Santa Cruz), 1:5000 for polyclonal chicken antibody IgY to MAP2 (Chemicon), 1:200 for polyclonal rabbit antibody to Pax2 (Covance), 1:50 for polyclonal goat antibody to Pax8 (Santa Cruz), 1:50 for polyclonal goat antibody to Dlx5 (Santa Cruz), 1:2000 for monoclonal mouse antibody IgG1 to Engrailed 1 (Hybridoma Bank), 1:1000 for polyclonal guinea pig antibody to myosinVIIa (Oshima et al., 2007), 1:1000 for polyclonal rabbit antibody to espin (courtesy of Dr. A. J. Hudspeth, The Rockefeller University), 1:100 for polyclonal rabbit antibody to p27Kip1 (NeoMarkers), 1:200 for polyclonal rabbit antibody to cadherin 23 (courtesy of Dr. Ulrich Mueller, Scripps), and 1:100 for monoclonal mouse antibody to hair cell antigen (courtesy of Dr. Guy Richardson, Sussex). FITC-, TRITC-, and Cy5-conjugated species and subtype-specific secondary antibodies (Jackson ImmunoResearch) were used to detect primary antibodies. Nuclei were visualized with 40,6-diamidino-2-phenylindole (DAPI). Proper labeling of Dlx5, Pax2, and Pax8 antibodies was confirmed on sections of mouse otic placodes and otocysts; specificity was confirmed by pre-incubating Dlx5 and Pax8 antibodies with blocking peptides (Santa Cruz) for 2 hr at room temperature (data not shown). Specific Dlx5 immunoreactivity in the mouse otocyst was observed in the cytoplasm, which may indicate a transient translocation of the protein at this specific developmental stage. Images were acquired with a Zeiss Axioimager/LSM 5 Exciter fluorescence and confocal microscope.

Statistical Analysis.

Data are presented as mean values±standard deviation (SD) with the number of independent experiments (n) indicated. Statistical differences were determined with paired two-tailed t tests using Aabel 3 (Gigawiz) on a Macintosh computer (Apple) running OS X.

Scanning Electron Microscopy.

The cells were fixed for 2 hr with 2.5% glutaraldehyde/4% paraformaldehyde with 50 mM CaCl2 and 20 mM MgCl2 in 0.1 M HEPES buffer (pH=7.4) and treated with 1% OsO4 in the same buffer, 1% tannic acid in water, and 1% OsO4 in water, followed by 1% tannic acid in water for 1 hr each. The specimens were washed three times between each treatment step and then dehydrated in a graded ethanol series, and finally dried by critical point drying. Specimens were viewed with a Hitachi S-3400N variable pressure SEM operated under high vacuum at 5-10 kV at a working distance of 7-10 mm. All chemicals were supplied by Electron Microscopy Sciences (Hatfield, Pa.).

Hair Cell Mechanical Stimulation and Electrophysiology.

nGFP-expressing hair cell-like cells were identified by fluorescence microscopy, and nearby hair bundle-like protrusions were imaged with a 1003 objective with brightfield optics. Recordings were conducted with an Axoclamp 200a (Axon Instruments) amplifier, interfaced with a DIGIDATA® 1332 board (Axon), and jClamp Software (Scisoft). Mechanical stimulation was done with a stiff glass probe attached to a piezo stack.

More specifically, cultured cells were placed onto the stage of an OLYMPUS® BX 51 fixed stage upright microscope and imaged using a 100× dipping objective using brightfield optics. Images were collected using a C2400 NARISHIGE® analog camera coupled via a framegrabber to a PC computer using Image J software. Soda glass electrodes, coated with ski wax (MR. ZOG'S SEX WAX®) to limit stray capacitance, of resistances 3-5MΩ, were used to record from both ES and iPS cells. The culture medium was replaced during electrophysiological recordings with a solution containing (in mM) 140 NaCl, 5 KCl, 1 $MgCl_2$, 2.5 CaCl, 10 HEPES, 6 glucose, 2 pyruvate, 2 ascorbate, 2 creatine. The bath was continually perfused with a peristaltic pump (Gilson, Madison Wis.) at a rate of 4 ml/hr. The internal solution contained (in mM) either 145 KCl or CsCl, 3.5 $MgCl_2$, 5 ATP, 5 creatine phosphate, 1 EGTA, 10 HEPES, 2 ascorbate. Recordings were made using an Axoclamp 200a (Axon Instruments) amplifier coupled to a Digidata 1332 board (Axon Instruments) used for computer interfacing. jClamp Software (Scisoft) was used for all data collection. Data was analyzed with ORIGIN® software (Microcal). Borosilicate pipettes with tip diameters of 2-3 mm, filled with external solution, were used to create a path for the recording electrode by physically separating the green fluorescent cells from the surrounding cells. Junction potentials and leak subtraction (where needed) was applied offline during analysis. Mechanical stimulation was accomplished using a glass probe attached to a piezo stack (Physik Instrumente) whose motion was also controlled with the jClamp software. The voltage signal to the piezo stack was filtered at 10 kHz (Frequency Devices) and amplified. Apical perfusion for drug application was performed using a picospritzer (General Valve) controlled with digital pulses generated with jClamp software. A borosilicate pipette of 3-5 mm tip diameter was placed about 20 mm from the bundle of interest. The picospritzer was initially used for mechanical stimulation, in which case the pressure was increased and the pipette positioned closer to the hair bundle being investigated. Fluorescence was observed with a conventional mercury lamp exciting at 488 nm and measuring emissions at 510 nm. Data are presented as mean±SD with n (number of measurements) in brackets.

Results

ESCs and iPSCs from Math1/nGFP Mice.

The transgenic mouse strain Math1/nGFP expresses a nuclear variant of enhanced green fluorescent protein (nGFP) that is driven by an Atoh1 enhancer (Lumpkin et al., 2003). All sensory hair cells of the Math1/nGFP inner ear express nGFP from the time when they differentiate into nascent hair cells until adulthood (FIGS. 1A and 1B), which makes stem cells isolated from this mouse line useful for guidance studies because stem cell-derived hair cell-like cells can be identified by nGFP expression (Diensthuber et al., 2009; Oshima et al., 2007). From Math1/nGFP blastocysts, we isolated four lines of ESCs that expressed typical ESC markers and displayed ESC colony morphology when grown on mouse embryonic fibroblast (MEF) feeders in the presence of leukemia inhibitory factor (LIF) (FIGS. 1C-1G). Interestingly, all four Math1/nGFP ESC lines expressed the nGFP reporter, which was not unexpected because Math1 expression has been previously reported in ESCs (Azuara et al., 2006).

Figure 2:
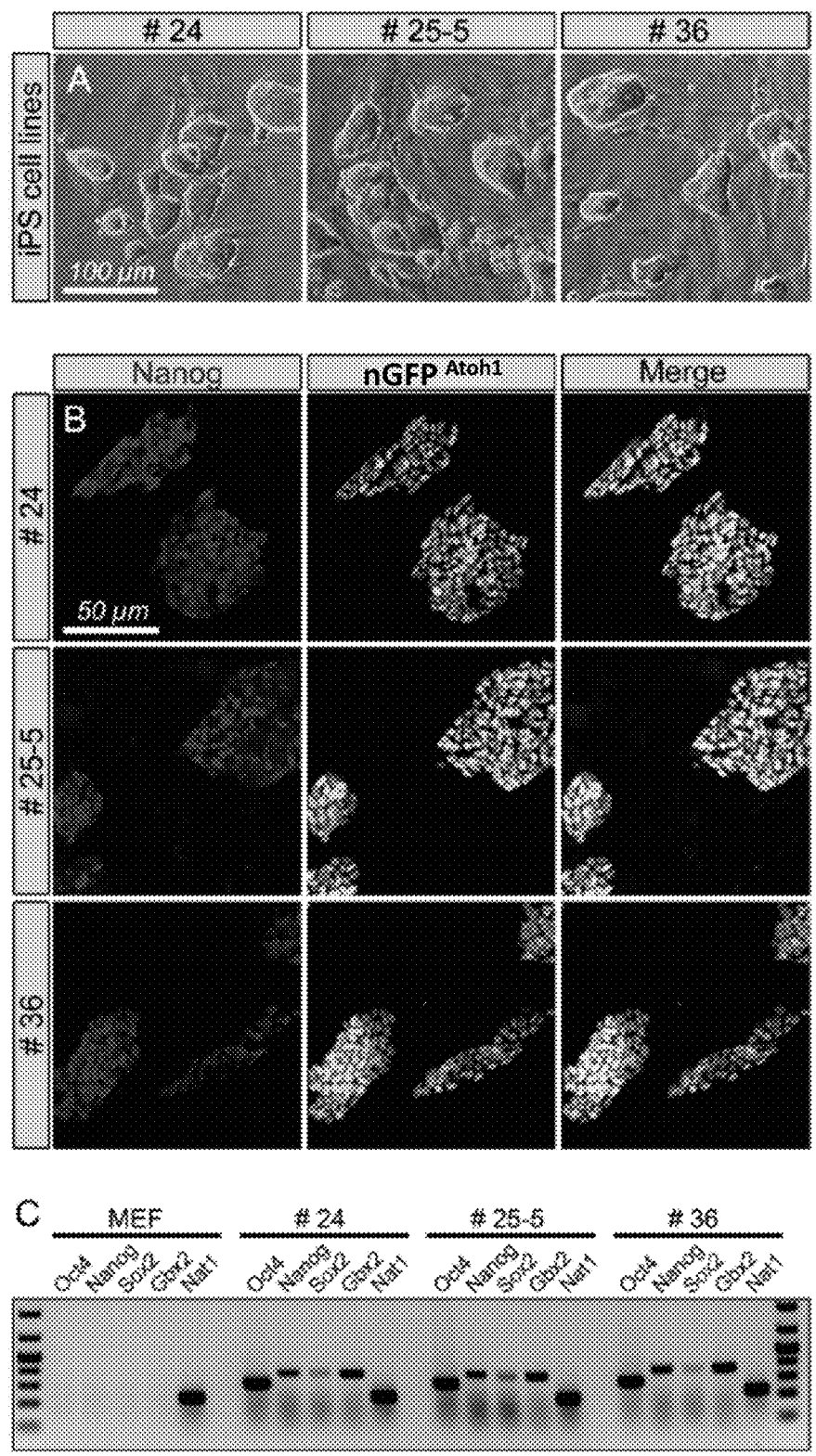
FIG. 2. Generation of iPS Cell Lines from Math1/nGFP Fibroblasts, Related to FIG. 1. (A) Transmitted light images of colonies of three derived iPS cell lines (#24, #25-5, and #36), maintained on MEF feeder cells. (B) Immunostainings of the three iPS cell lines shown in (A) with antibodies to Nanog as well as visualization of nGFPAtoh1 expression. (C) RT-PCR-based analysis of ES cell marker expression in iPS cell lines #24, #25-5 and #36.
Figure 3:
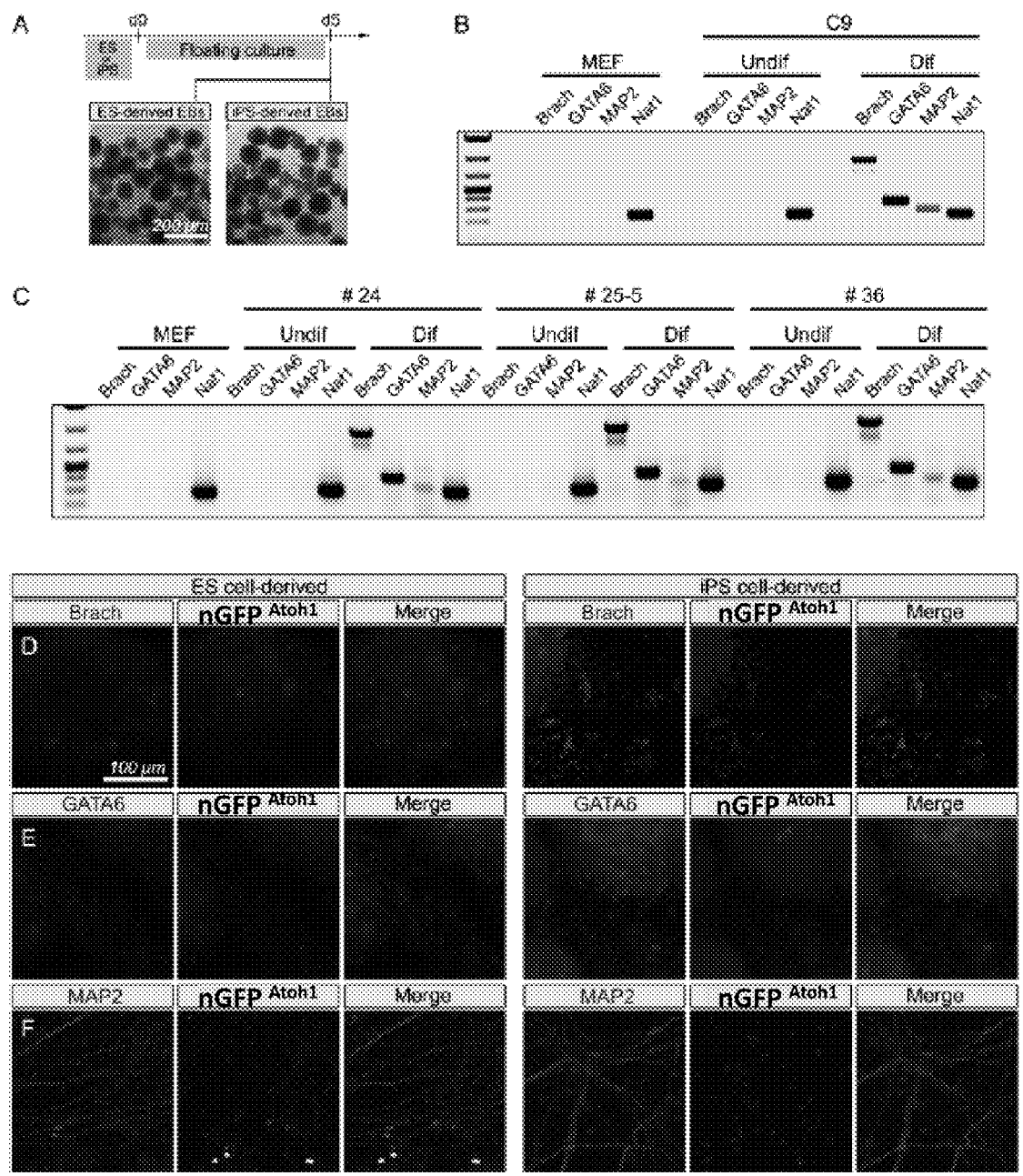
FIG. 3. Expression of Markers for All Three Germ Layers upon Differentiation of Math1/nGFP ES and iPS Cells. (A) ES cells and iPS cells were dissociated into single cells and cultured in nonadhesive plates for five days to form embryoid bodies (EBs). (B) RT-PCR analysis of transcripts for Brachyury (Brach), GATA6, and MAP2, which are markers for meso-, endo-, and ectodermal cells, respectively. Shown are results for MEF feeder cells, C9 ES cells (Undif), and EBs derived from C9 ES cells (Dif). (C) Same analysis for iPS cell lines #24, #25-5, and #36. (D-F) Embryoid bodies from C9 ES and #25-5 iPS cells were plated into gelatin-coated culture plates and immunostained one day later with antibodies to Brachyury (Brach) and GATA6. MAP2 immunostaining was done 7 days after plating to allow for maturation of neuronal phenotypes. nGFPAtoh1 expression was downregulated in all cultures of differentiated ES and iPS cell lines. Nuclear DAPI staining is shown.
Figure 4:
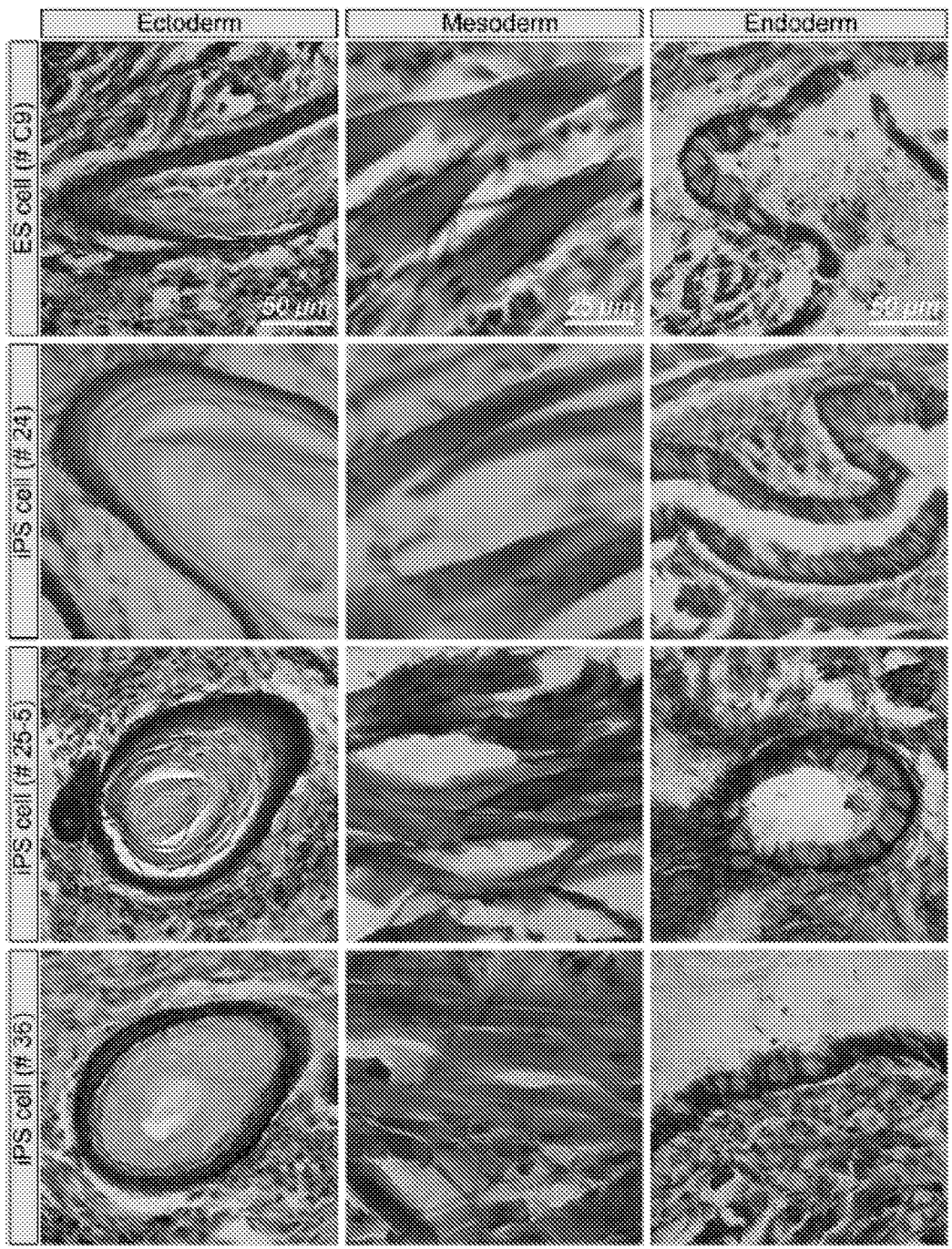
FIG. 4. Histology of Teratomas Formed after Injection of C9 ES Cells and Three iPS Cell Lines (#24, #25-5 and #36) into Immunodeficient SCID Mice. 2-4 mice per cell line were injected and all mice investigated developed teratomas within 4 weeks of injection. The formed teratomas contained derivatives of all three germ layers. Ectoderm: squamous cell epithelium with keratin pearl formation. Mesoderm: rhabdomyocytes with cross striations. Endoderm: respiratory epithelium consisting of ciliated cells and mucus-producing cells. All images were obtained from paraformaldehyde-fixed cryosections stained with hematoxylin and eosin.

To generate iPSC lines, we infected Math1/nGFP embryonic fibroblasts with retroviruses expressing Oct4, Sox2, Klf4, and cMyc (Takahashi and Yamanaka, 2006). Primary colonies were picked, subcloned, and expanded on MEF feeder cells (FIG. 2A). The iPSC lines expressed typical ESC marker genes as well as the Math1/nGFP reporter (FIGS. 2B and 2C). We randomly differentiated ESC and iPSC lines by generation of embryoid bodies, removal of LIF, and culturing the embryoid body cells before analyzing expression of endo-, meso-, and ectodermal markers. We found upregulation of transcripts for GATA6, Brachyury, and microtubule-associated protein 2 (MAP2), which was confirmed by immunocytochemistry (FIGS. 3A-3F). In differentiated cell populations, expression of the nGFP reporter was reduced or absent, and cells that expressed germline-specific markers were consistently nGFP negative. This observation indicates that the Math1/nGFP reporter is active in ESCs and iPSCs and downregulated upon differentiation of the cells. When ESC and iPSC lines were injected subcutaneously into immunodeficient mice, we found formation of typical teratomas. The teratomas consisted of tissues that could be assigned to all three germ layers, indicative of the pluripotency of the ESC and iPSC lines (FIG. 4).

Generation of Presumptive Ectoderm that is Competent to Otic Induction.

It has been hypothesized that inhibition of primitive streak cell identities during embryoid body formation will suppress the induction of endo- and mesoderm from uncommitted epiblast cells. Establishment of primitive streak cells upon differentiation of ESCs depends on the presence of active Wnt and TGF-b/nodal/activin signaling, which recapitulates early events that lead to germ-layer induction in the mammalian embryo (Gadue et al., 2006). We anticipated that interference with Wnt and TGF-b signaling would strongly suppress the formation of primitive streak cells and concomitantly increase presumptive ectoderm. In addition, we presumed that activation of IGF signaling would promote the formation of anterior ectoderm (Pera et al., 2001), which is more competent to otic induction than trunk ectoderm (Groves and Bronner-Fraser, 2000). Similar strategies were used to generate ectoderm that is capable of differentiating into retinal cell types (Ikeda et al., 2005; Lamba et al., 2006; Osakada et al., 2008).

Figures 5A, 5B, 5C:
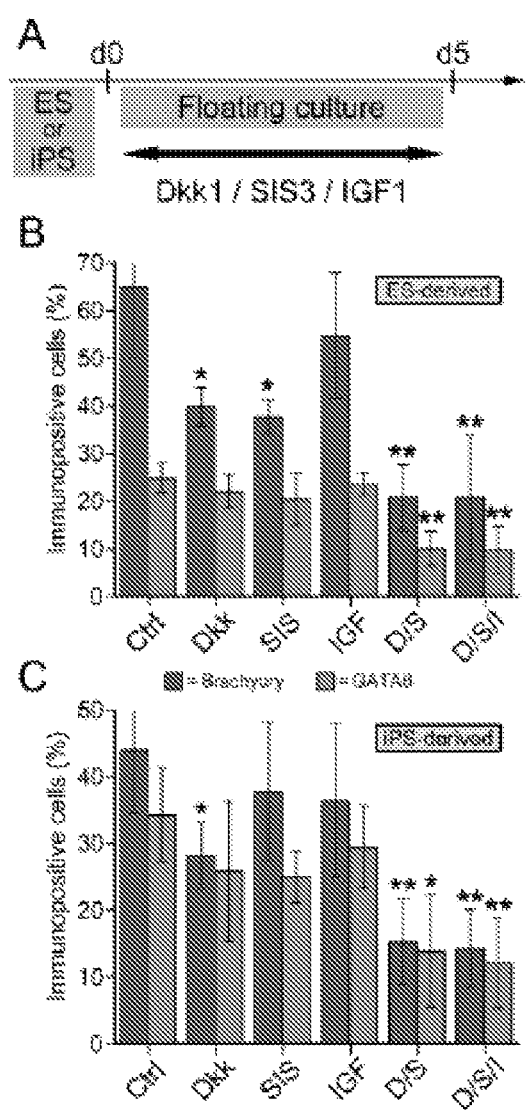
FIG. 5A-C. Suppression of Meso- and Endodermal Cell Differentiation by Interference with Wnt- and TGF-b Signaling. (A) C9 ESCs and No. 25-5 iPSCs were dissociated into single cells and cultured in nonadhesive plates for 5 days to form embryoid bodies in presence of Dkk1, SIS3, and IGF-1, as indicated. (B and C) Embryoid bodies from ESCs (B) and iPSCs (C) were generated in presence of the factors indicated. Ctrl, no factors added; D/S, Dkk1 and SIS3; D/S/I, Dkk1, SIS3, and IGF-1. Error bars represent the SD. n=5. * indicates $p<0.05$ and ** indicates $p<0.01$, determined with paired, two-tailed t tests.
Figures 5D, 5E, 5F, 5G:
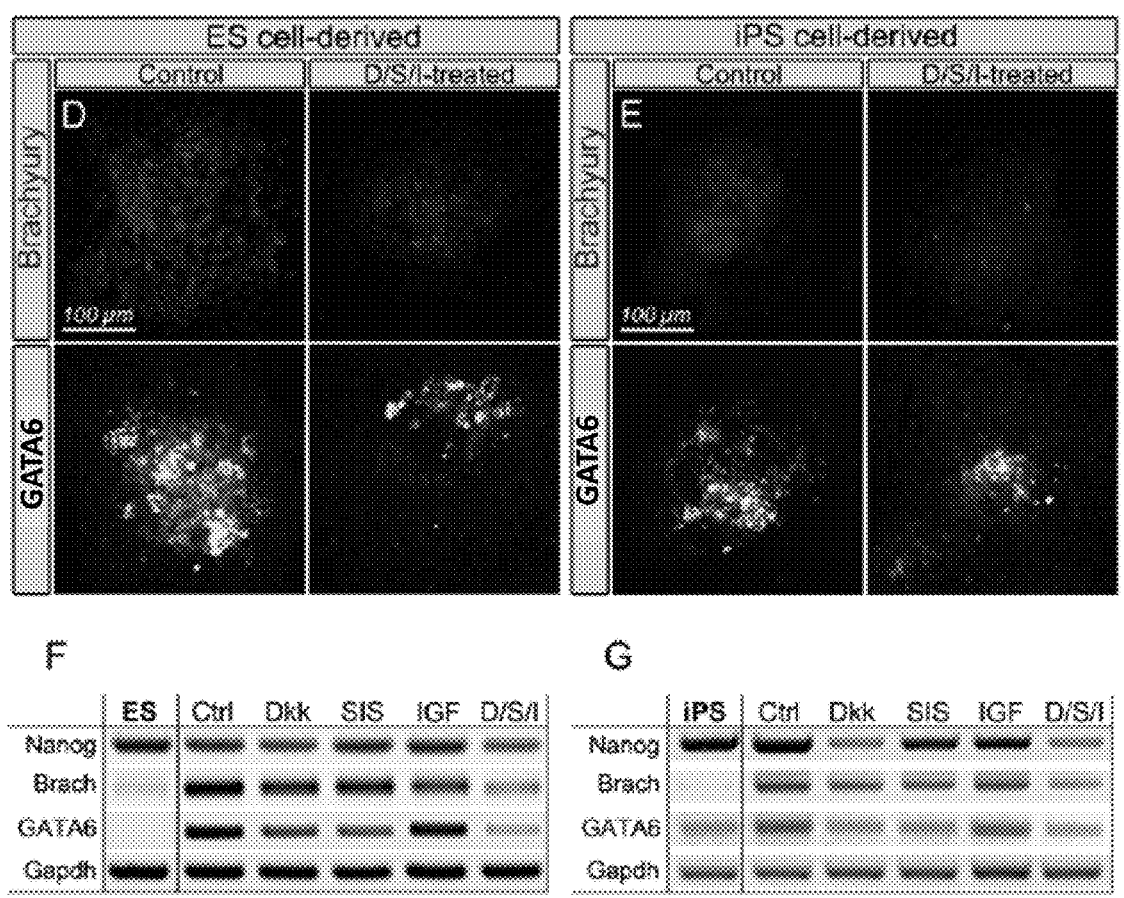
FIG. 5D-G. Suppression of Meso- and Endodermal Cell Differentiation by Interference with Wnt- and TGF-b Signaling, continued. (D and E) Representative immunostainings of plated embryoid bodies from ESCs. (D) and iPSCs (E). Treatment with D/S/I reduced the number of cells immunopositive for Brachyury and GATA6. (F and G) RT-PCR analyses show downregulation of transcripts for Brachyury and GATA6 in D/S/I-treated cultures of ESC-(F) and iPSC-(G) derived populations. Expression of the pluripotent and ESC marker Nanog is also reduced most noticeably after D/S/I treatment. Ctrl, embryoid bodies generated without factors added; ES, ESCs before differentiation; iPS, iPSCs before differentiation. Nuclear DAPI staining is shown. See also FIGS. 1-4.

Embryoid bodies, generated from ESCs and iPSCs, were treated with the Wnt inhibitor Dkk1 (Glinka et al., 1998), the selective inhibitor of Smad3 (SIS3) that interferes with TGF-b signaling (Jinnin et al., 2006), and IGF-1, either alone or in combinations (FIG. 5A). Embryoid body-derived cells were attached to culture dishes and stained with antibodies to Brachyury and GATA6, indicators of differentiation along the meso- and endodermal lineages, respectively. We observed that treatment of ESC-derived embryoid bodies with either Dkk1 or SIS3 alone significantly reduced the number of Brachyury-positive cells (FIG. 5B). For iPSC-derived embryoid bodies, only Dkk1 alone was able to significantly reduce the Brachyury-expressing cell population (FIG. 5C). Combination of Dkk1 and SIS3 significantly reduced the number of Brachyury-positive cells from 65.0%±14.9% to 20.9%±6.9% in ESC-derived populations and from 44.1%±9.6% to 15.3%±6.5% in iPSC-derived populations (FIGS. 5B and 5C). These two factors also led to significant reduction of the GATA6-positive cell population from 24.9%±3.1% to 10.1%±3.7% (ESC derivatives) and from 34.3%±7.1% to 13.9%±8.4% (iPSC derivatives). Combination of Dkk1, SIS3, and IGF-1 (D/S/I) was most effective, leading to a reduction of Brachyury-positive cells to 20.8%±13.1% and of the GATA6-expressing cell population to 9.8%±5.0% in ESC-derived cell populations (FIGS. 5B and 5D). Likewise, iPSC-derivatives displayed reduction to 14.3%±5.8% (Brachyury) and 12.1%±6.8% (GATA6) (FIGS. 5C and 5E). The reduction of Brachyury and GATA6 expression was also detectable at the transcript level, where the mRNA for the ESC marker Nanog was also reduced most in D/S/I-treated cultures (FIGS. 5F and 5G).

Figures 6A, 6B, 6C:
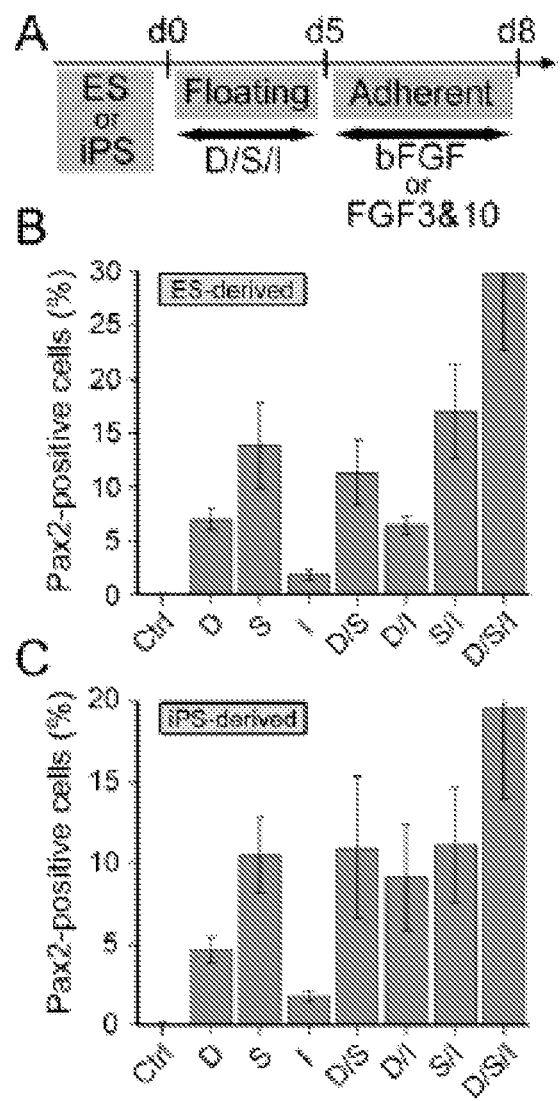
FIG. 6A-C. Otic Induction Is Most Efficient in D/S/I-Treated ESCs and iPSCs. (A) Embryoid bodies were generated for 5 days in presence of Dkk1, SIS3, and IGF-1, as indicated; subsequent adherent culture was done for 3 days in fibronectin-coated plates in presence of otic inducers bFGF or FGF3&10. (B and C) ESC-(B) and iPSC-(C) derived cultures, exposed for 3 days to bFGF, were immunostained with antibodies to Pax2, and the percentage of Pax2-positive cells of the total cell population was determined. D/S/I treatment most efficiently increased the number of cells that responded with upregulation of Pax2 to bFGF-treatment. Ctrl, no added factors during embryoid body formation. Error bars represent the SD. n=3.

To test for competence to otic induction, we plated the D/S/I-treated embryoid bodies into gelatin-coated culture dishes and exposed them to FGFs, which have been shown to be both sufficient and necessary for otic induction (Freter et al., 2008; Ladher et al., 2005; Phillips et al., 2004; Pirvola et al., 2000; Pirvola et al., 2002). We used bFGF as a general otic inducer because it activates several different FGF receptor subtypes and has been previously used to substitute for the proposed natural otic-inducing FGF3 and FGF10 (Groves and Bronner-Fraser, 2000; Pauley et al., 2003; Vendrell et al., 2000; Wright and Mansour, 2003). As a marker for otic induction, we used antibodies to Pax2 (Li et al., 2004), and we quantified the number of Pax2-positive cells after 3 day treatment with bFGF (FIG. 6A). In both ESC- and iPSC-derived populations, we observed the largest increase of Pax2-positive cells in cultures that were previously exposed to D/S/I, reaching 29.8%±7.1% for ESC derivatives and 19.6%±5.6% for iPSC derivatives (FIGS. 6B-6E). Comparable results were obtained when we used FGF3 and FGF10 instead of bFGF, which resulted in 24.6%±4.0% Pax2-positive cells for ESC derivatives and 16.3%±4.0% for iPSC derivatives (n=3). Neither the initial factors alone nor combinations of two factors were as effective as the triple combination; therefore all three factors/compounds are needed to generate a cell population that is most responsive to FGF treatment. Dkk1 and SIS3 are mainly effective in suppressing endo- and mesodermal lineages, whereas the effect of IGF-1 only became obvious after FGF induction, where D/S/I-treatment resulted in an increased number of Pax2-positive cells when compared with D/S treatment (p values [paired t test] for these experiments were 0.04 for ESC-derived cells and 0.1 for iPSC-derived cells indicative of significance in case of ESC-derived cells and a possible trend for iPSC-derived cells) (FIGS. 6B and 6C). Control cultures not treated with any of the three initial factors, but treated with bFGF, displayed only a few Pax2-expressing cells (0.05±0.04% for ESC and 0.1±0.09% for iPSC derivatives).

Figures 6D, 6E, 6F, 6G:
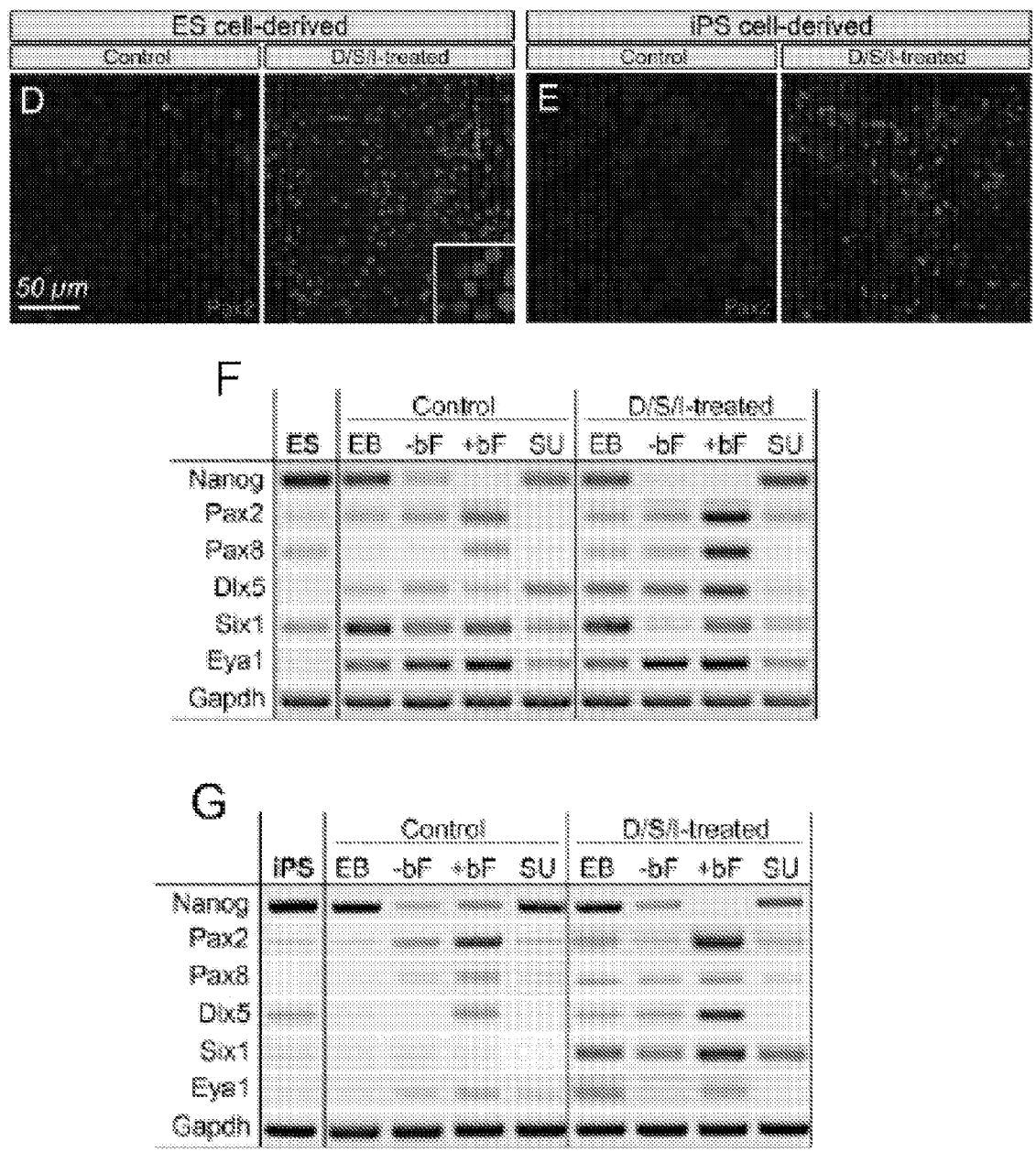
FIG. 6D-G. Otic Induction Is Most Efficient in D/S/I-Treated ESCs and iPSCs (continued). (D and E) Representative immunocytochemical images showing upregulation of Pax2 in ESC-derived (D) and iPSC-derived (E) cultures in response to D/S/I treatment followed by bFGF exposure. Control, bFGF-treated cultures of embryoid bodies generated with no added factors. The inset shows a higher-magnification view of the nuclear staining. (F and G) RT-PCR analyses for expression of Nanog and the early otic markers Pax2, Pax8, Dlx5, Six1, and Eya1 in cultures derived from ESCs (F) and iPSCs (G). ES, ESCs before differentiation; iPS, iPSCs before differentiation; EB, embryoid bodies harvested at day 5 (d5). –bF and +bF indicate absence and presence of bFGF between d5 and d8. SU, SU5402 treatment between d5 and d8.

RT-PCR confirmed the strong upregulation of Pax2 in ESC and iPSC cultures after D/S/I treatment and exposure to bFGF (FIGS. 6F and 6G). Transcripts for other genes that are expressed in the developing inner ear, such as Pax8, Dlx5, Six1, and Eya1 (Brown et al., 2005; Groves and Bronner-Fraser, 2000; Ohyama et al., 2006; Xu et al., 1999; Zou et al., 2004), were also most abundant in D/S/I- and bFGF-treated cultures. Double immunostaining revealed that 56.0%±5.3% of the Pax2-positive cells in ESC-derived cultures coexpressed the otic marker Dlx5 (FIG. 6H). Conversely, 73.2%±10.3% of Dlx5-positive cells coexpressed Pax2. In the native developing inner ear, Pax2 expression precedes Dlx5 expression (Brown et al., 2005), and it is therefore not surprising to find only partial coexpression. Likewise, 64.1%±5.6% of Pax2-expressing cells colabeled with antibody to Pax8 (FIG. 6I); 43.0%±8.3% of Pax8-positive cells coexpressed Pax2. Pax8 is induced prior to Pax2 in the native developing inner ear (Hans et al., 2004; Heller and Bra¯ndli, 1999) and well before Dlx5; therefore, we did not expect to detect complete coexpression of these markers because their temporal expression periods during native otic development do not completely overlap.

Figure 7:
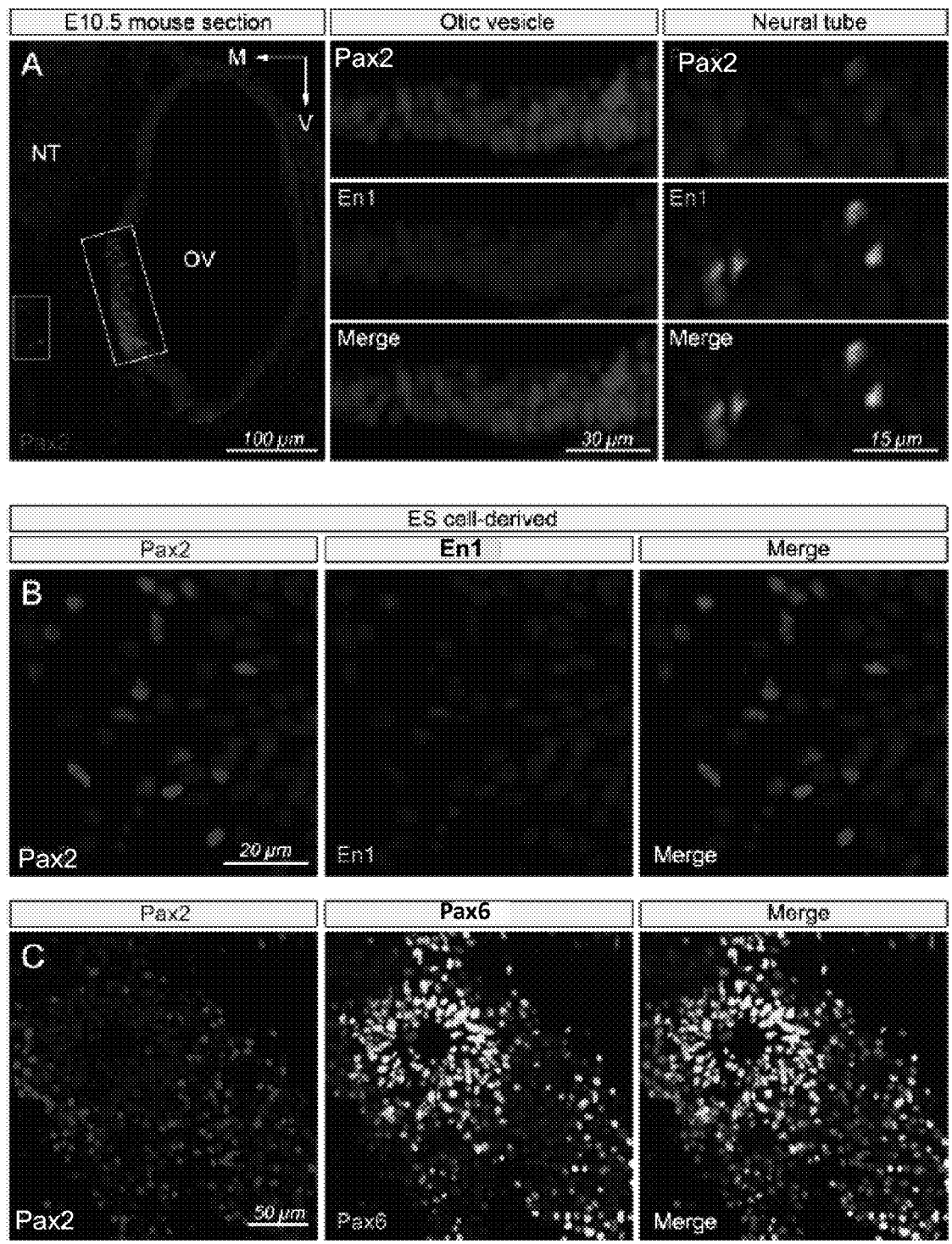
FIG. 7. Further Characterization of D/S/I- and bFGF-Treated Progenitor Cell Populations. (A) (left) Transverse section through the otic vesicle of a 10.5-days-old mouse embryo, immunostained with antibodies to Pax2. The series of panels in the center show a magnification of the inset showing Pax2-positive cells in the medio-ventral pre-prosensory region of the otic vesicle (OV). Engrailed 1 (En1) immunoreactivity is not detectable in Pax2-expressing otic vesicle cells. The series of panels on the right show a magnification of the smaller inset in the neural tube (NT) region where Pax2-positive neural progenitors coexpress engrailed 1. (B) About 1% of the Pax2-expressing cells derived from ES (shown) and iPS (not shown) cells coexpressed engrailed 1. (C) Pax6-immunopositive cells in ES (shown) and iPS (not shown) cell-derived cultures did rarely overlap with the Pax2-positive cell population. Nuclear DAPI staining is shown.

Pax2 is not an inner ear-specific marker. For example, it is also expressed in neural progenitors in close vicinity to the otic vesicle at the midbrain/hindbrain boundary, where it is coexpressed with engrailed 1 (Rowitch and McMahon, 1995) (FIG. 7A). Engrailed 1, however, is not associated with Pax2-expressing otic progenitor cells in the developing otic vesicle (FIGS. 7A and 7B). D/S/I+bFGF treatment only resulted in 1.2%±0.8% of engrailed 1-positive cells, which all expressed Pax2, indicating that the vast majority of Pax2-positive cells were not midbrain/hindbrain boundary neural progenitors.

Our guidance strategy utilizes similar steps as retinal cell guidance protocols (Ikeda et al., 2005; Lamba et al., 2006; Osakada et al., 2008). As a result, we would expect to find retinal progenitors in ESC- and iPSC-derived cultures. Indeed, Pax6-expressing cells were detectable in D/S/I+ bFGF-treated cultures and were clearly distinct from the Pax2-positive cellpopulation (FIG. 7C).

Native otic induction is blocked by inhibition of FGF signaling (Alsina et al., 2004; Martin and Groves, 2006). Blockade of FGF signaling with the FGF receptor inhibitor SU5402 resulted in abolishment of Pax2 induction (FIG. 6J), which shows that also in guidance experiments, FGF signaling is essential for otic induction from presumptive ectodermal cells. Overall, the strong upregulation and coexpression of multiple early inner ear markers suggests that D/S/I followed by bFGF treatment sufficiently mimics, in a culture dish, the events leading to otic induction during normal embryonic development.

Hair Cell Differentiation.

Figures 8E, 8F:
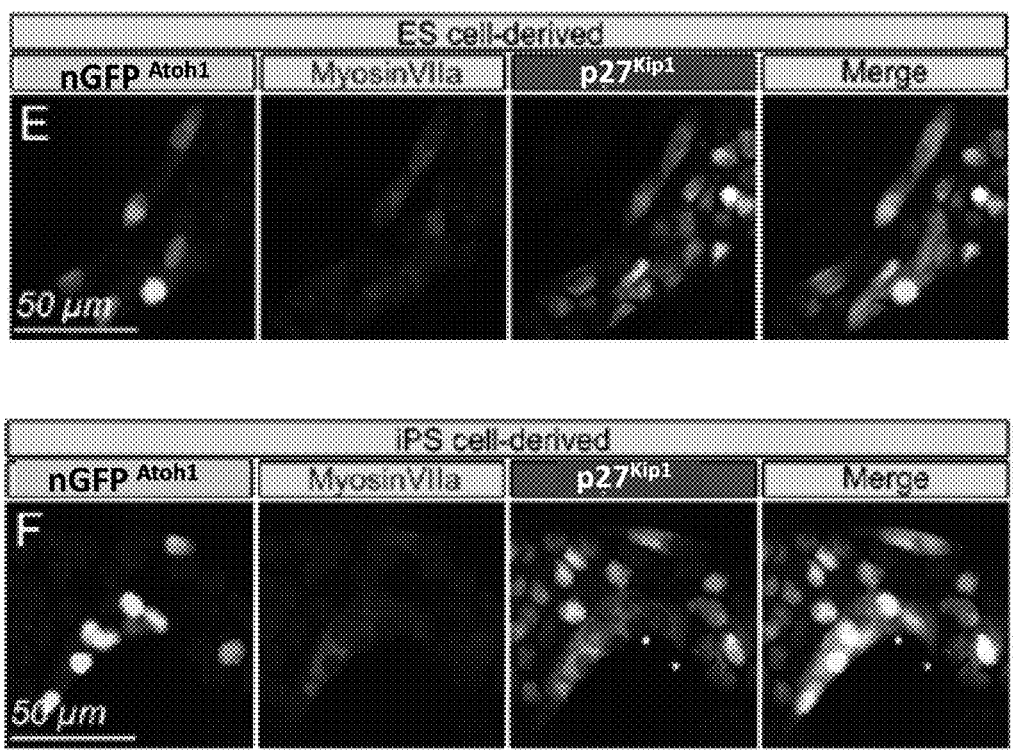
FIG. 8E-F. Differentiation into Hair Cell-like Cells (continued). (E and F) ESC-(E) and iPSC-(F) derived progenitors that expressed nGFPAtoh1 displayed cytosolic immunoreactivity for p27Kip1 and were surrounded by nGFP-negative cells with nuclear p27Kip1 expression. Nuclear DAPI staining is shown.

Withdrawal of growth factors and serum-free culture on gelatin is an effective way to initiate differentiation of ESC-generated otic progenitors (Li et al., 2003). This approach led to upregulation of hair cell markers, but in culture, the generated hair cell-like cells did not adopt typical hair cell morphology. We tested four different substrates for differentiation of ESC- and iPSC-generated otic progenitors, generated by D/S/I+bFGF treatment. When ESC- and iPSC-derived cells were plated onto fibronectin, gelatin, or MEF feeders, we detected nGFP-positive cells (FIGS. 8A and 8B). Per 104 plated cells, 955±153, 857±240, and 520±95 nGFP-positive cells were found in ESC-derived cultures, as well as 670±110, 597±170, and 360±66 nGFPpositive cells in iPSC-derived cultures (on fibronectin, gelatin, and MEFs, respectively; n=3). A subpopulation of the nGFPpositive cells was immunopositive for the hair cell marker myosin VIIa: 37±5, 12±8, and 33±12 (ESC derived) and 24±6, 8±5, 25±6 (iPSC derived). We detected neither cytomorphological specializations nor expression of hair bundle markers, such as espin (Zheng et al., 2000).

When we plated the ESC- and iPSC-derived otic progenitors onto a layer of mitotically inactivated chicken utricle stromal cells, we observed a different behavior. The progenitors formed defined patches of cells that harbored nGFP-positive cells, which coexpressed the hair cell marker myosin VIIa and the actin filament-bundling protein espin (FIGS. 8C and 8D), which is abundantly expressed in the stereocilia of the mechanosensitive hair bundle, where it is necessary for hair cell function (Zheng et al., 2000). Per 104 plated cells, 1186±150 (ESC derived) and 908±209 (iPSC derived) cells were nGFP positive, 139±49 and 113±24 cells were nGFP and myosin VIIa positive, and 36±7 and 24±19 cells expressed both markers plus espin (n=4). When we plated $10^4$ control cells that were not subjected to D/S/I, but were otherwise treated identically, we only found a few (135±84 and 30±18, ESC and iPSC derived) nGFP-positive cells and no myosin VIIa- or espin-expressing cells (n=4). These results show that D/S/I treatment is a specific requirement for hair cell differentiation from ESCs and iPSCs.

Interestingly, the cells surrounding the nascent hair cell-like cells displayed nuclear immunoreactivity for p27Kip1 (FIGS. 8E and 8F), a cell-cycle regulator that is initially expressed in the nuclei of all cells of the prosensory domains of the developing inner ear and later becomes restricted to supporting cells (Chen and Segil, 1999). In nascent hair cells, p27Kip1 translocates from the nucleus to the cytoplasm before the protein is no longer detectable in fully differentiated hair cells. We observed that after 12 days of differentiation culture, the majority of nGFP/myosin-VIIa double-positive cells displayed cytoplasmic p27Kip1 immunoreactivity.

Figure 9:
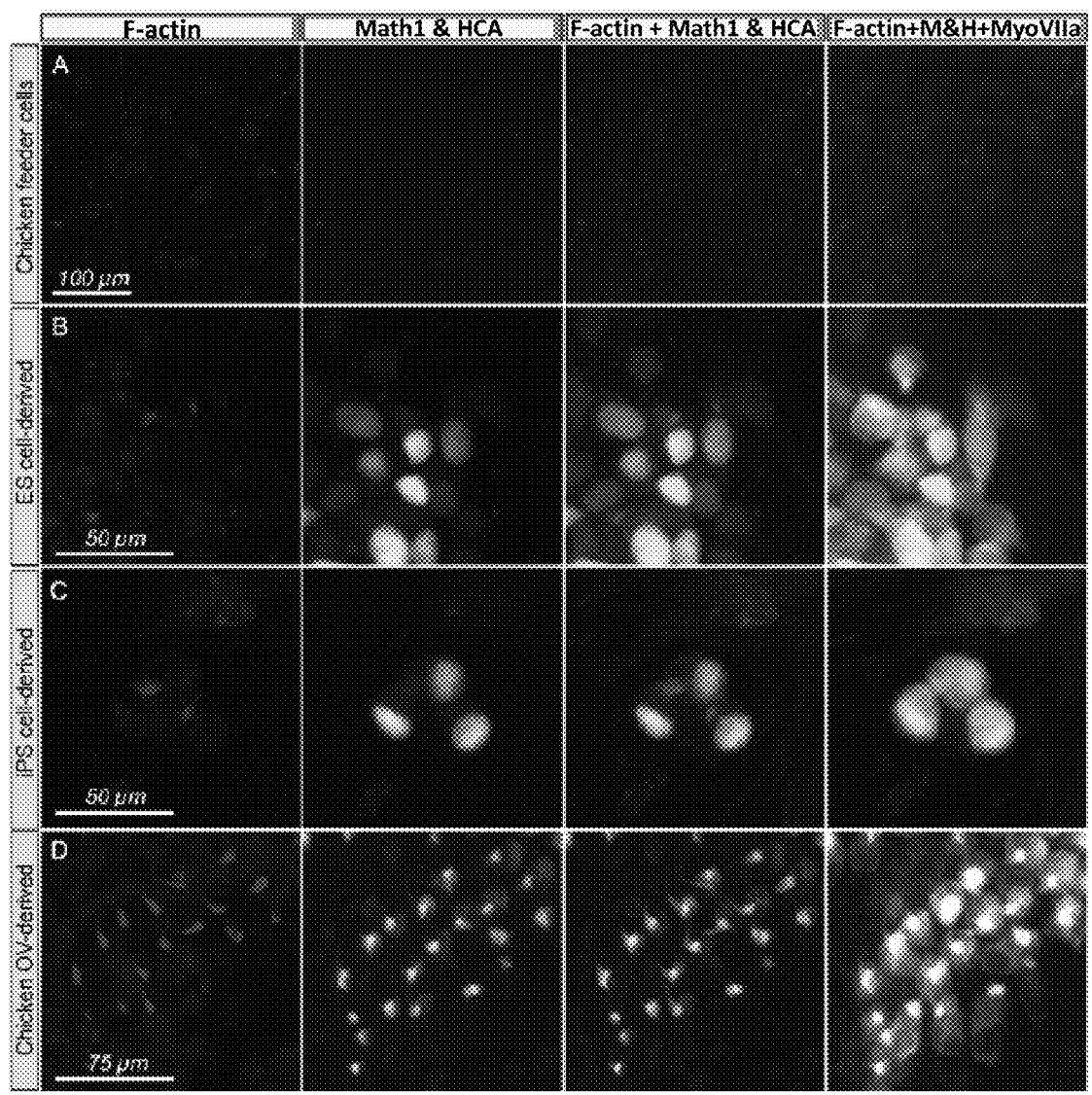
FIG. 9. Mitotically Inactivated Chicken Utricle Stromal Cells Are Not the Source of Hair Cell-like Cells. (A) Mitotically inactivated chicken utricle stromal cells did not generate hair cell-like cells or F-actin-rich protrusions, even after protracted culture periods of two weeks. (B and C) ES (B) and iPS (C) cell-derived hair cell-like cells display F-actin-rich protrusions that are not immunostained with monoclonal antibody to chicken Ptprq (also known as hair cell antigen=HCA, FITC channel), but that display nGFPAtoh1 expression. Note that the fluorescence in the green channel is exclusively located in the nucleus. Myosin VIIa (shown in white) further confirms the hair cell identity of the nGFPAtoh1-positive cells. (D) Chicken otic vesicle cells were seeded onto mitotically inactivated chicken utricle stromal cells and differentiated into hair cells that were immunopositive for hair cell antigen (HCA) that was detectable at the base of the F-actin-positive hair bundles. The chicken hair cells did not display nuclear green fluorescence. Nuclear DAPI staining is shown.

Supporting cells isolated and expanded from embryonic chicken utricle have previously been used to generate hair celllike cells (Hu and Corwin, 2007). We performed a series of control experiments to ensure that hair cell-like cells that differentiated in ESC- and iPSC-derived cultures were neither chicken hair cells nor the product of fusion of a murine cell with a chicken hair cell. First, it is unlikely that chicken hair cells will develop from the nonsensory stromal cell layer. When we cultured inactivated chicken utricle stromal cells for up to 3 weeks, we never observed cells with hair cell morphology or cells that expressed hair cell markers (FIG. 9A). Furthermore, ESC- and iPSC derived myosin VIIa- and nGFP-positive cells did not stain with a monoclonal antibody specific to the chicken isoform of hair bundle protein tyrosine phosphatase receptor Q (Ptprq, also known as hair cell antigen [Goodyear et al., 2003]) (FIGS. 9B and 9C). Conversely, chicken hair cells, derived from dissociated otic vesicle cells that were seeded onto stromal cells, displayed strong Ptprq immunoreactivity but lacked nuclear green fluorescence (FIG. 9D).

ESC- and iPSC-Derived Hair Cell-Like Cells have Stereociliary Hair Bundles.

Figure 10:
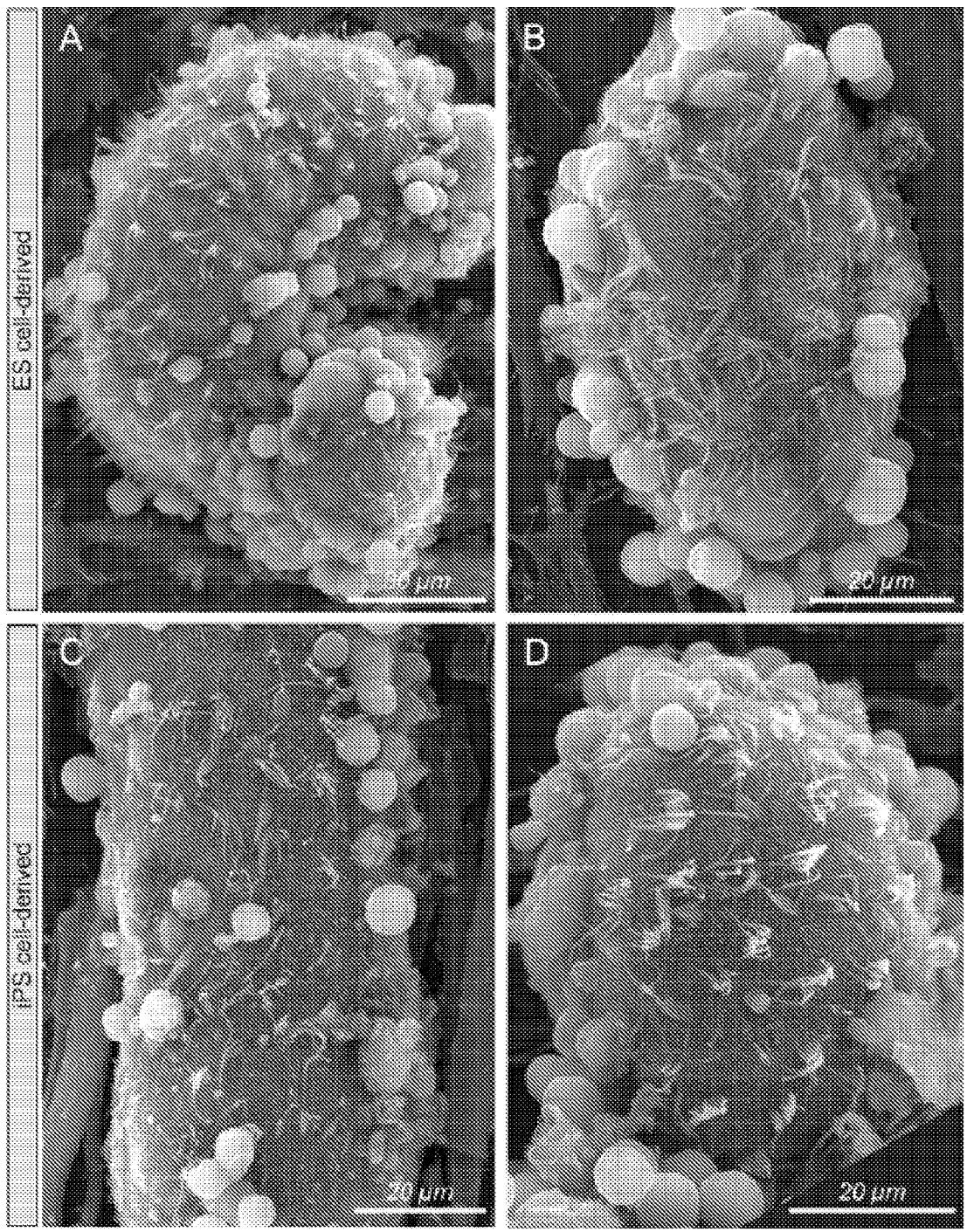
FIG. 10. Scanning Electron Microscopic Images of Clusters with Many nGFPAtoh1 Positive Cells Displayed Hair Bundle-like Protrusions. These clusters formed after D/S/I- and bFGF-treated ES (A, B) and iPS(C, D) cells were cultured for 12 days on mitotically inactivated chicken utricle stromal cells.
Figure 11:
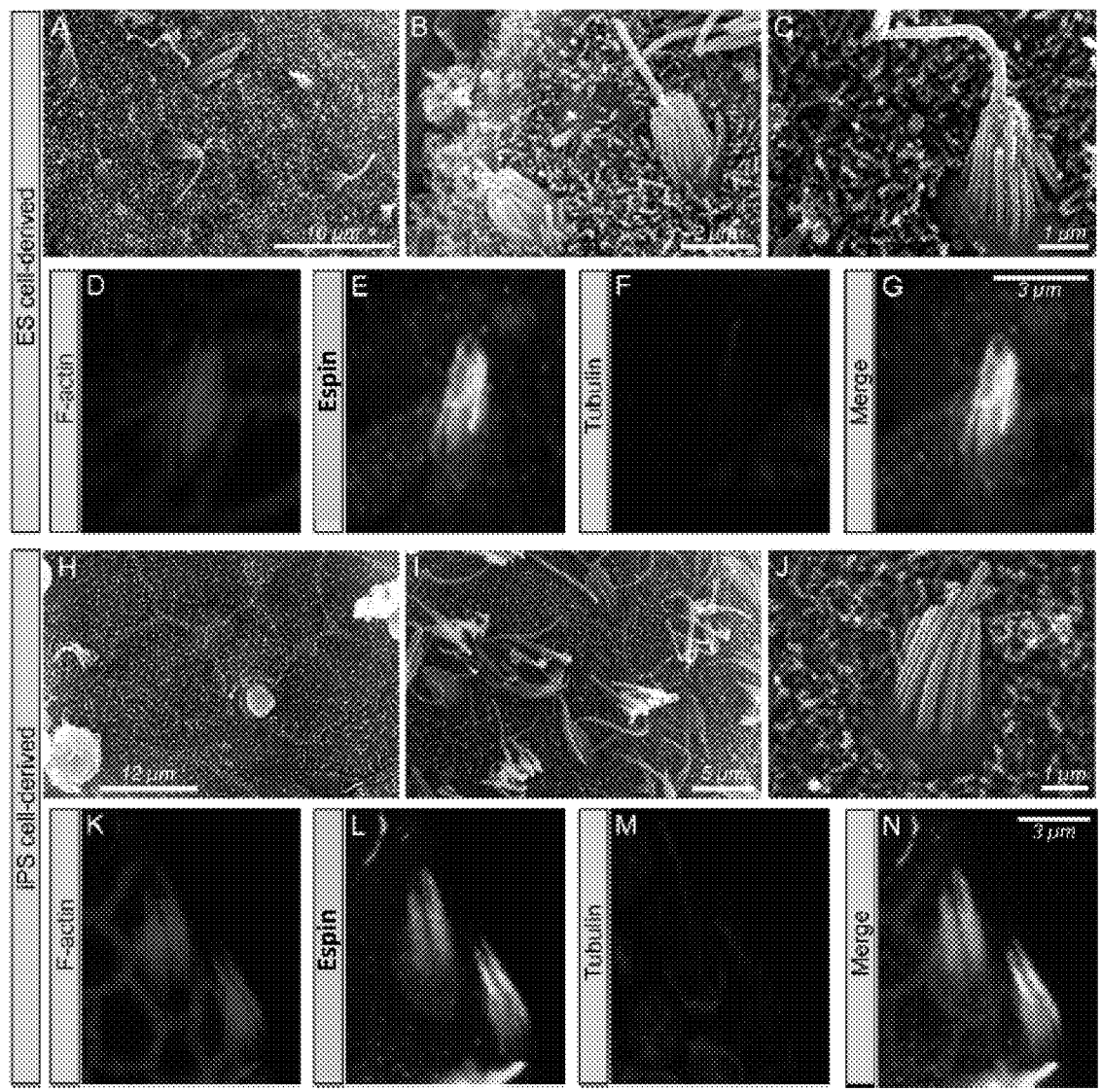
FIG. 11. Hair Bundle-like Protrusions of ESC- and iPSC-Derived Cells. (A-C and H-J) Scanning electron microscopic views of the surface of ESC-(A-C) and iPSC-(H-J) derived cell clusters after 12 days differentiation on mitotically inactivated chicken utricle stromal cells. (D-G and K-N) Projections of confocal stacks of hair bundle-like protrusions of ESC-(D-G) and iPSC-(K-N) derived cells. F-actin-filled membrane protrusions were visualized with TRITC-conjugated phalloidin. The actin-bundling stereociliary protein espin was visualized with FITC-conjugated secondary antibodies (green), and antibodies to beta-tubulin were visualized with Cy5-conjugated secondary antibodies to visualize the kinocilium-like structures.

The occurrence of asymmetrically distributed espin immunoreactivity toward one side of the presumptive hair cells (FIGS. 8C and 8D) raised the question of whether the cells were developing hair bundle-like structures. To answer this question, we analyzed clusters containing nGFP-positive cells by scanning electron microscopy (SEM) (FIG. 10). Protruding from the surface of the clusters, structures that were highly reminiscent of stereociliary hair bundles were visualized at different stages of maturation (FIGS. 11A-11C and 11H-11J) (Tilney et al., 1992). The hair bundle-like structures displayed single acentric protrusions reminiscent of kinocilia, which were consistently located toward the side of the bundle that featured the tallest stereocilia-like protrusions. Cytoskeletal stereocilia cores consist of F-actin, crosslinked by espin, whereas kinocilia are tubulin filled. When we visualized F-actin and espin in bundles protruding from ESC- and iPSC-derived clusters, we found that stereocilia-like extensions were labeled with phalloidin and antibody to espin (FIGS. 11D, 11E, and 11K-11L). The longer kinocilia remained unlabeled with both reagents, but they displayed immunoreactivity for tubulin (FIGS. 11F, 11G, 11M, and 11N).

Figure 12:
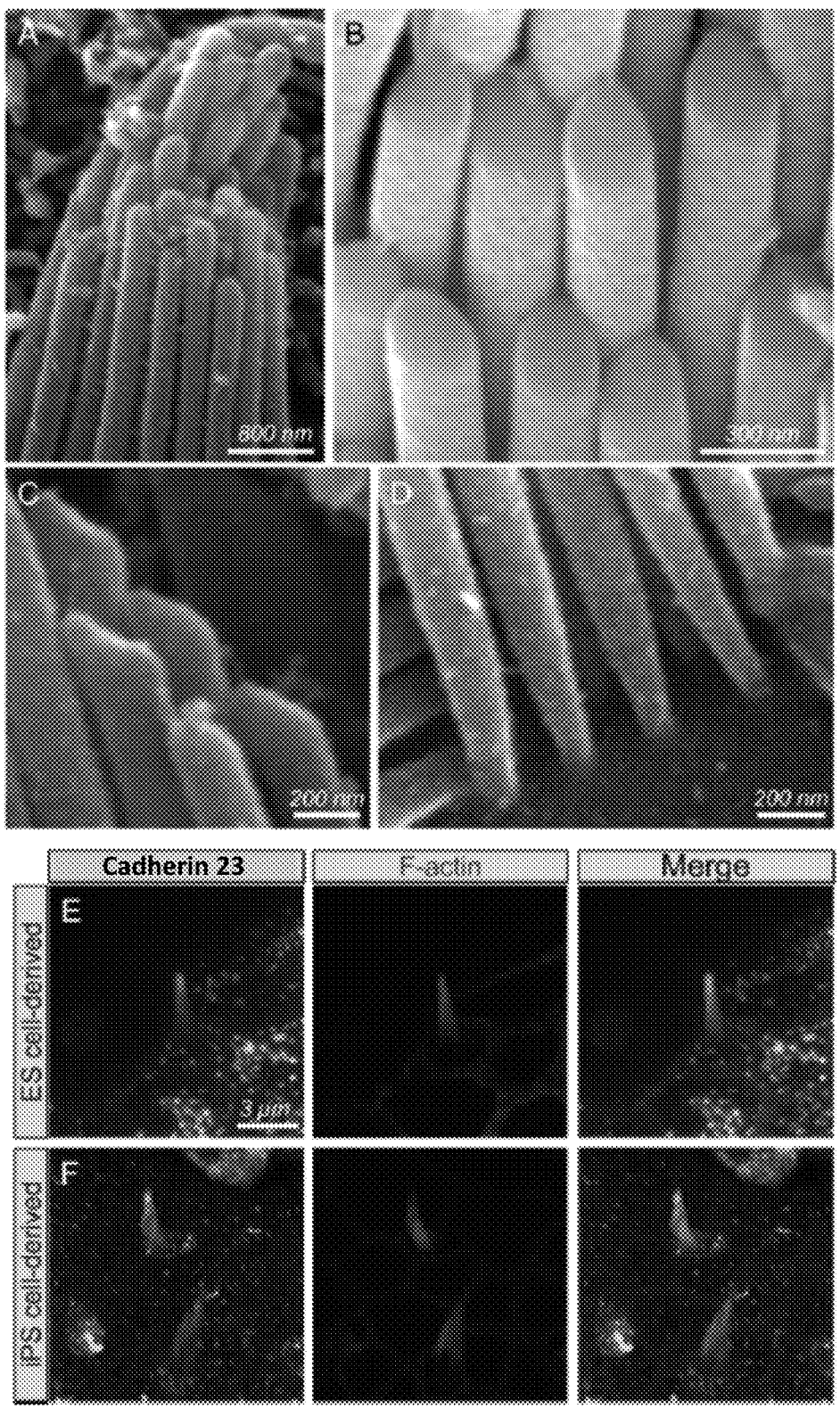
FIG. 12. Hair Bundle-like Protrusions and Interstereociliary Links Revealed with Scanning Electron Microscopy and Expression of Cadherin 23. (A) Many links between stereociliary-like protrusions on a ESC-derived cell. (B) An iPSC-derived cell shows stereociliary-like membrane protrusions that are connected at their tops with their taller neighbors. Also note the asymmetrical shape of the tops. (C) Asymmetrical tops and connections in an ESC-derived cell. (D) Tapered bases of stereociliary-like protrusions in an ESC-derived cell. (E and F) Hair bundle-like protrusions of ESC-(E) and iPSC-(F) derived cells immunostained with antibodies to cadherin 23 (FITC) and colabeled with TRITC-conjugated phalloidin.

We further noticed many interstereociliary links as well as links between the tips of stereocilia and the sides of taller neighboring stereocilia (FIGS. 12A-12O). Multiple links are reminiscent of nascent hair cells, which transiently display many interstereociliary links that can be visualized with antibodies to cadherin 23 (Boeda et al., 2002; Kazmierczak et al., 2007; Michel et al., 2005; Siemens et al., 2004). We found that the protrusions were labeled with antibodies to cadherin 23 (FIGS. 12E and 12F), further indicating that the bundles correspond to immature hair cell stereociliary bundles. The tops of short stereocilia that are connected with tip links to their taller neighbors usually appear to be pointed and asymmetric (Lin et al., 2005), which could be an indication of tension in the link. ESC- and iPSC derived hair cell-like cells displayed asymmetric or pointed stereociliary tips that appeared to be linked by thin filaments to the sides of the next tallest neighbors (FIGS. 12B and 12C). Finally, we observed that stereocilia of stem cell-derived hair cell-like cells were tapered at their bases (FIG. 12D), which is a hallmark of hair cell stereocilia (Tilney et al., 1983).

These results show that mitotically inactivated utricle stromal cells provide one or a combination of signals that induce the formation of hair bundles. Although the activity provided by stromal cells is unknown, we hypothesize that the signal(s) are not entirely secreted because stromal cell conditioned medium was unable to evoke hair bundle differentiation (no espin-positive cells, n=3). Conversely, plating of ESC- and iPSC-derived cells on paraformaldehyde-fixed utricle stromal cells also resulted in abolishment of the hair bundle-inducing activity (n=3). Future identification of these signals could provide important clues about the mechanisms controlling the initiation of hair bundle growth during embryonic development. Our results indicate that hair bundles only grow in cells that express Math1 and myosin VIIa, but that expression of Math1 and myosin VIIa is not sufficient to induce hair bundle formation.

ESC- and iPSC-Derived Hair Cell-Like Cells are Mechanosensitive.

Figures 13A, 13B, 13C, 13D, 13E, 13F, 13G:
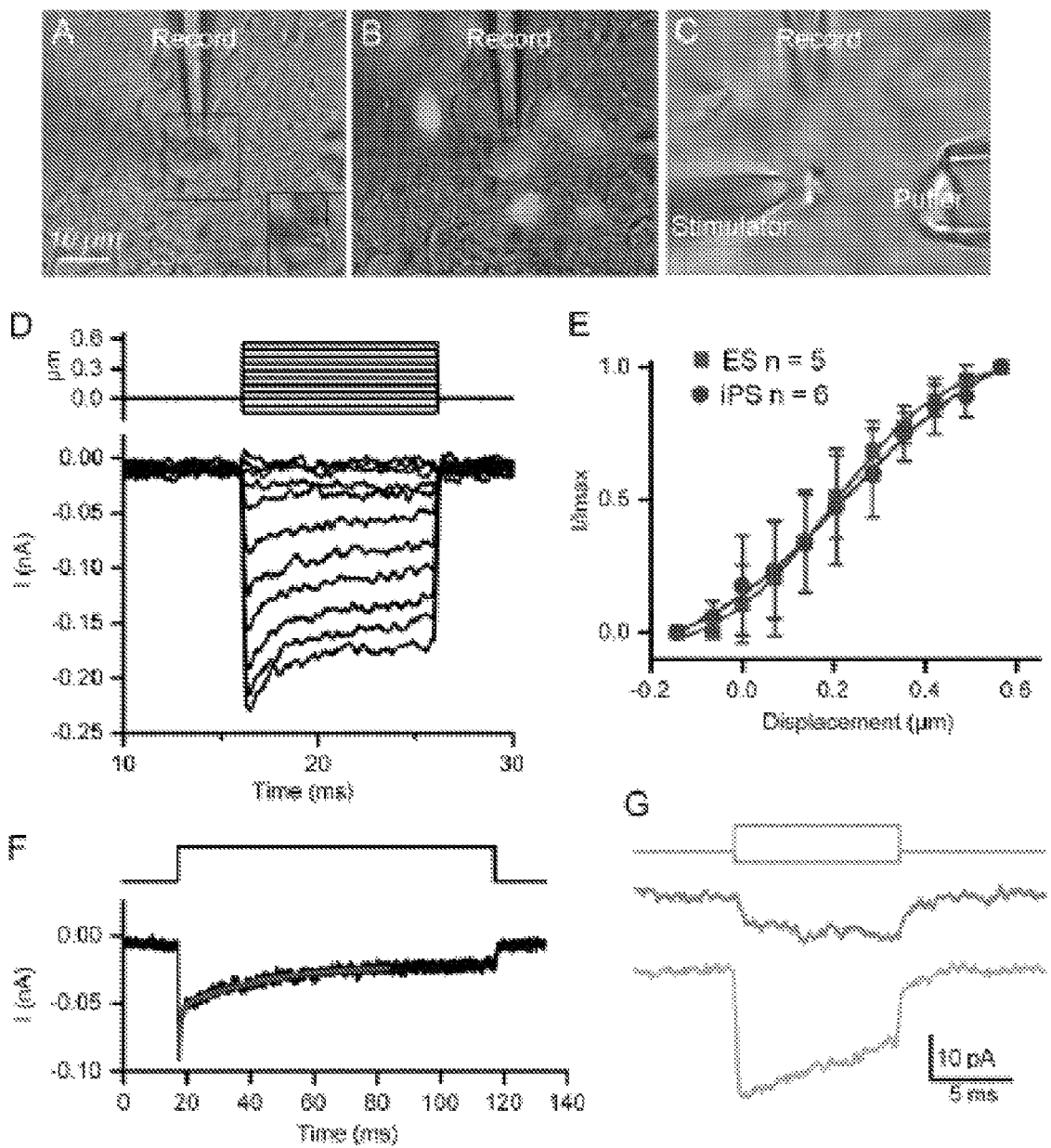
FIG. 13. Mechanical Responses Elicited from ESC- and iPSC-Derived Bundle-Bearing Cells. (A-C) Experimental setup showing transmitted light image (A) with recording electrode on a cell of choice. The inset shows same cell with stimulus probe attached. The arrow points to the bundle. (B) Fluorescent overlay onto (A) showing that recorded cell was nGFPAtoh1 positive. (C) Typical recording arrangement showing placement of patch electrode, stimulating electrode, and apical perfusion puffer. (D) Example of currents elicited from an iPSC-derived cell in response to a series of mechanical deflections (shown above). Currents increased with stimulus intensity. (E) Normalized current displacement plots for ESC- and iPSC-derived cells showing no difference in either half activation or sensitivity (solid lines are fits with Boltzmann functions with r2=0.99 for both; details in the main text); error bars represent the SD. (F) The response to an intermediate displacement for an iPSC-derived cell showing a time course for adaptation best fit by a double exponential. The line is fit with time constants of 0.89 and 16.7 ms (r2=0.99). (G) An example of the lack of directional sensitivity exhibited by many of the cells, here shown for an ESC-derived cell. Mechanical deflections of opposite polarity, shown above, elicited inward currents. (H) ESC-derived and (I) iPSC-derived cells with mechanically evoked currents that were reversibly blocked by 1 mM dihydrostreptomycin (DHSM). Stimulus is shown above currents.
Figures 13H, 13I:
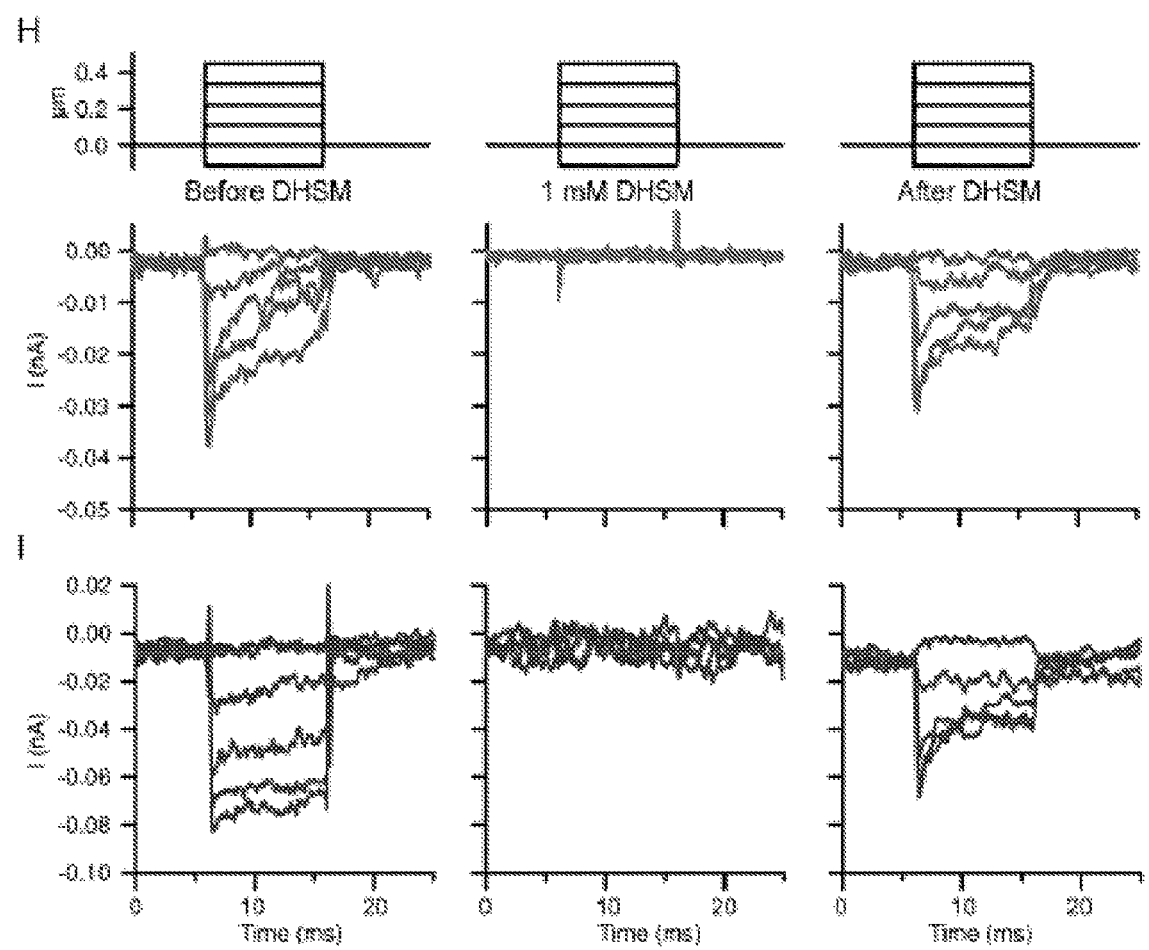

The occurrence of hair bundle-like structures with asymmetric tips and interstereociliary links raised our curiosity of whether the cells were responsive to mechanical stimulation. A total of 52 cells were successfully recorded, with 42 being derived from ESCs and ten being derived from iPSCs. No statistical differences were observed in any measured parameter. Cell capacitance was $3.7\pm1.0$ pF (n=52) and series resistance was $14\pm7$ MU (n=52) prior to compensation of up to 50%. Resting potentials were $45\pm7$ mV (n=7). Mechanosensitivity was probed in 45 of these cells with 24 positive responses. FIG. 13 shows examples of responses from both ESC- and iPSC-derived cells. The mean current amplitude was $74\pm82$ pA with responses ranging from 14 pA to 370 pA. Normalized current-displacement plots are shown in FIG. 13E for ESCs (n=5) and iPSCs (n=6). Single Boltzmann functions of the form $I/I_{max}=1/(1+e^{(x-x0)/dx})$, where x0 is the half activating displacement and dx is the slope, found no differences between populations. Values for x0 of $198\pm9$ and $224\pm18$ nm and dx values of $125\pm11$ and $125\pm18$ nm 1 were obtained for ESC- and iPSC-derived cells, respectively.

Adaptation is a complex process in which hair bundle dynamic range is enhanced and sensitivity maintained over large displacements (Eatock, 2000). It likely involves multiple mechanisms and has several distinct temporal components in mature hair cells (Wu et al., 1999). Adaptation matures in a stepwise manner, so that immature cells show little adaptation while mature cells have robust adaptation (Lelli et al., 2009; Michalski et al., 2009; Waguespack et al., 2007). Our results show a broad range of responses. 18% of the cells showed no adaptation, 45% showed a single time constant for decay of the current, and 37% showed the more mature double exponential decay in currents (FIGS. 13D and 13F). The fast time constant measured was $0.5\pm0.4$ ms (n=5) and the slow was $11\pm5$ ms (n=5). No relationship to current amplitude was observed. Directional sensitivity also matures over time and appears to correlate with the alignment of tip links orienting in one direction along the stereocilia (Waguespack et al., 2007). Immature hair cells do not show directional sensitivity. In a population of cells tested here, directional sensitivity was also ambiguous, as shown in FIG. 13G. This example demonstrates that either pushing or pulling on the hair bundle elicited an increase in current. Hair cell mechanotransduction currents are blocked by aminoglycosides (Kroese et al., 1989; Marcotti et al., 2005; Ricci, 2002). Mechanically induced currents were tested for pharmacologic sensitivity by local application of 1 mM dihydrostreptomycin (DHSM) to hair bundles and then mechanical stimulation. Both ESC- and iPSC-derived hair cell-like cell responses were antagonized reversibly by DHSM (FIGS. 13H and 13I), supporting the argument that the elicited current was comparable to that evoked in native sensory hair cells.

Hair Bundle-Bearing ESC- and iPSC-Derived Cells Display a Variety of Voltage-Dependent Currents.

Figure 14:
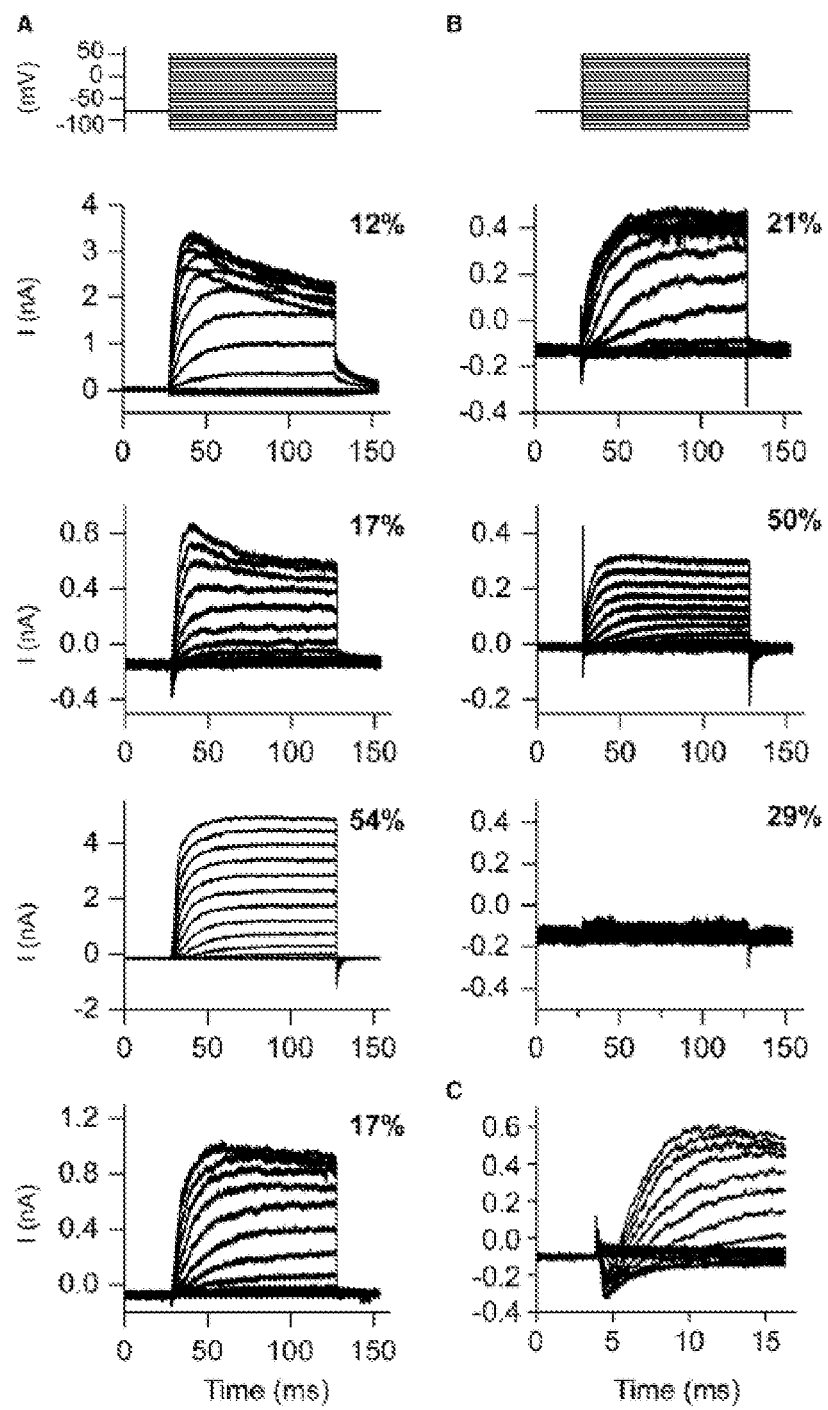
FIG. 14. Voltage-Dependent Currents Elicited from ESC- and iPSC-Derived Bundle-Bearing Cells. (A and B) Green fluorescent cells derived from either ESCs or iPSCs were voltage clamped at −84 mV and stepped between −120 and 50 mV in 10 mV increments. The resultant complex current responses are shown in (A) when K+ was in the internal solution and in (B) when Cs+ was the major monovalent ion. The percentages reflect the proportion of cells with this basic response type. Inward currents were also observed in about 30% of the cells. (C) Expanded view of the basic stimulus paradigm with Cs+ internally is shown to highlight the inward component of the complex current.
Figure 15:
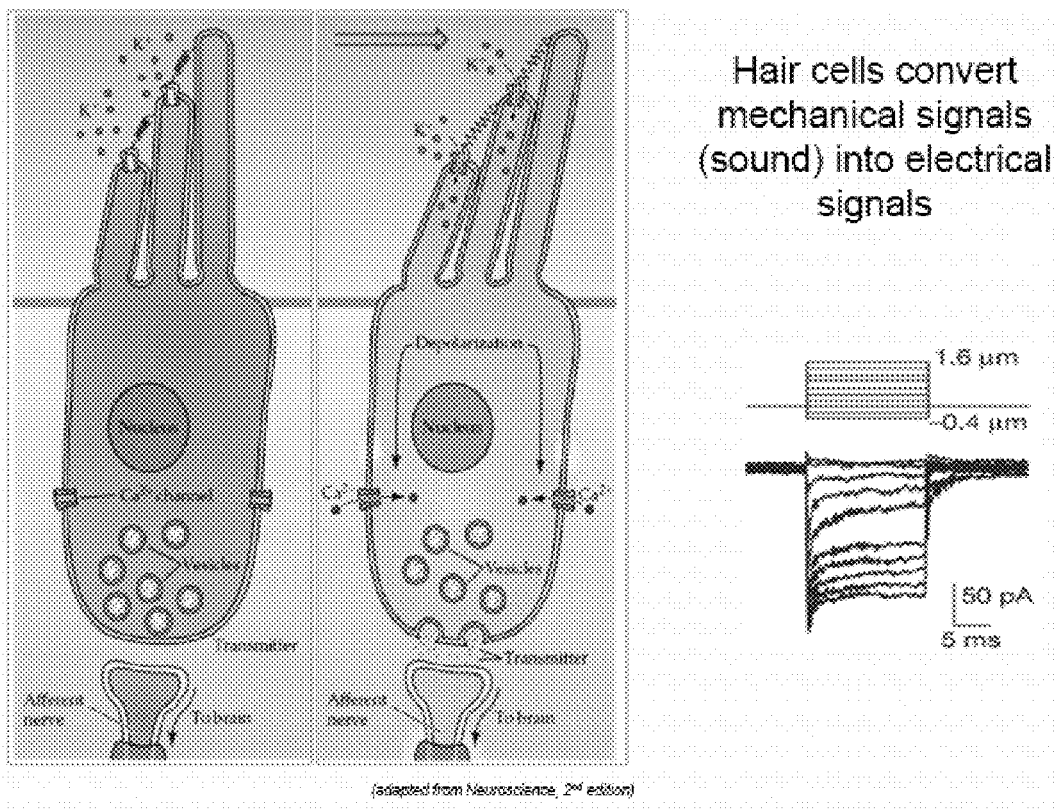
FIG. 15. Hair cells convert mechanical signals (sound) into electrical signals.
Figure 16:
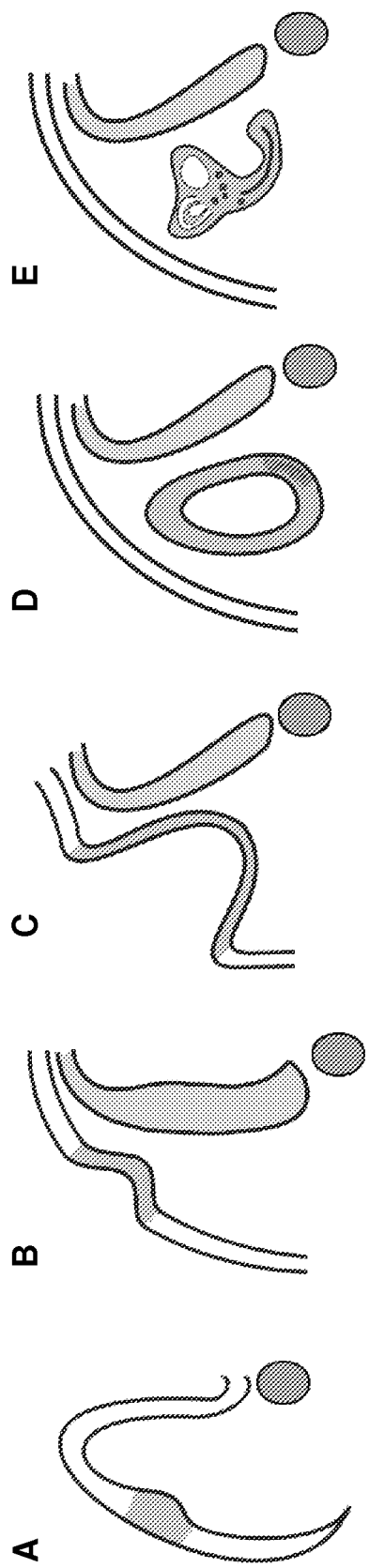
FIG. 16. Development of the inner ear. (A) Thickened Ectoderm; (B) Otic pit; (C) Invagination; (D) Otic Vesicle; (E) Otic Morphogenesis.
Figure 17:
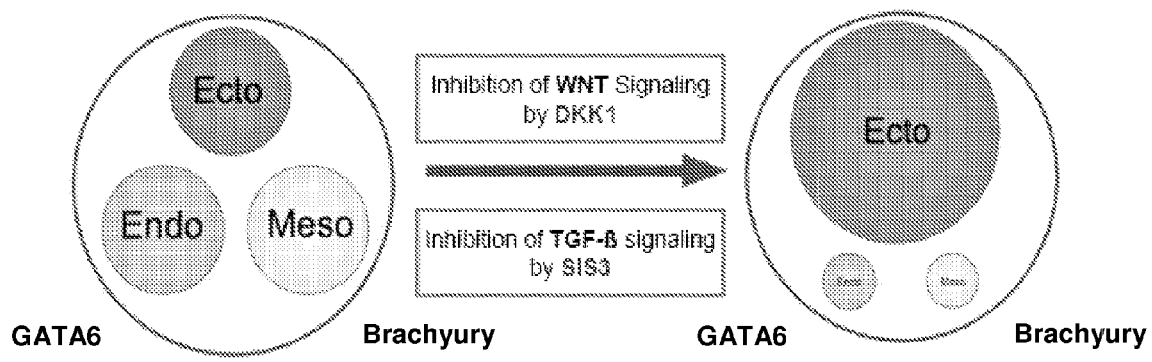
FIG. 17. Ectoderm enrichment in ESC population.
Figure 17:
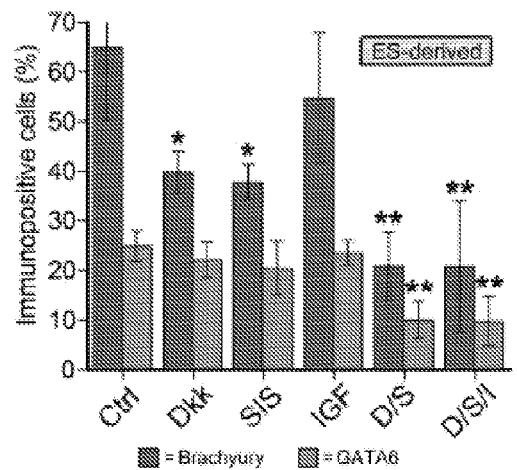
Figure 18:
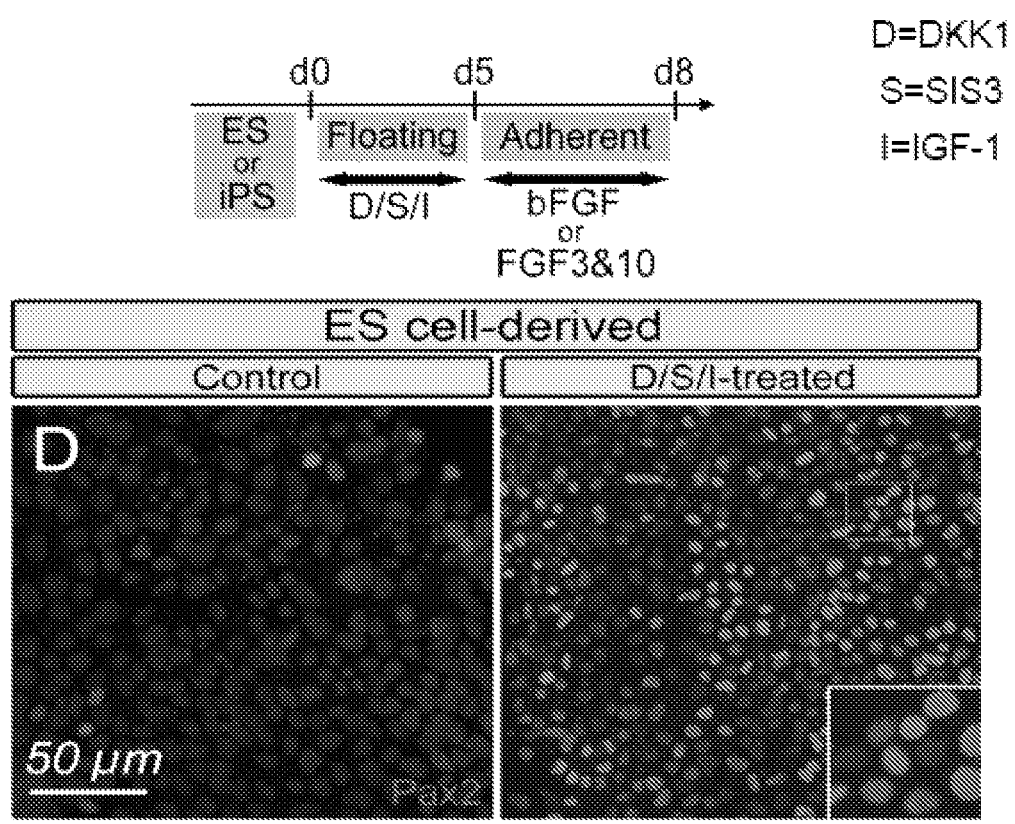
FIG. 18. Summary of otic progenitor cell induction from mESC.
Figure 19:
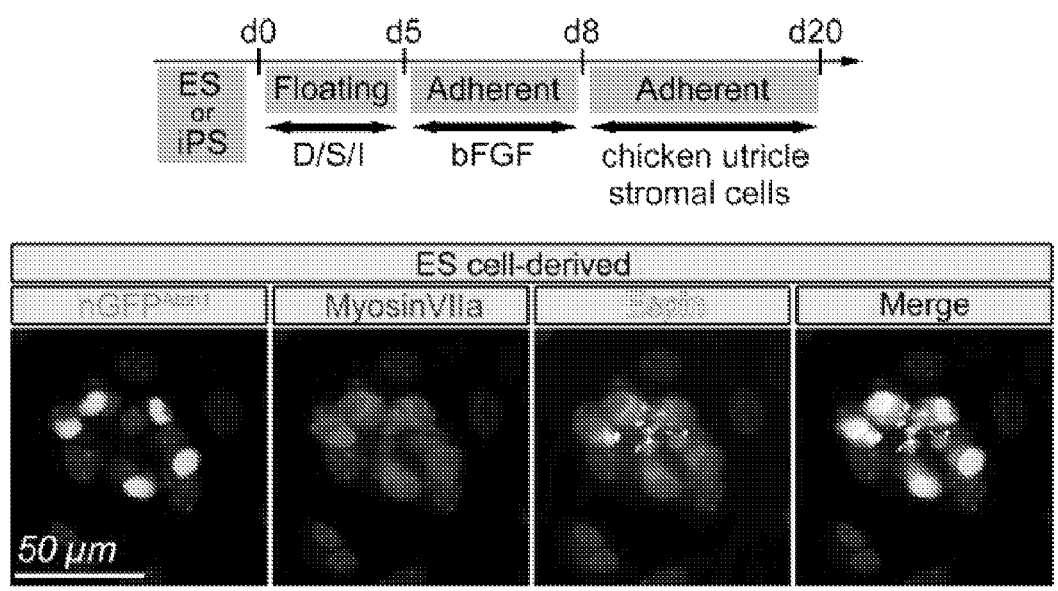
FIG. 19. Inner ear hair cell-like cell induction from mESC (see also FIGS. 10 and 11).
Figure 20:
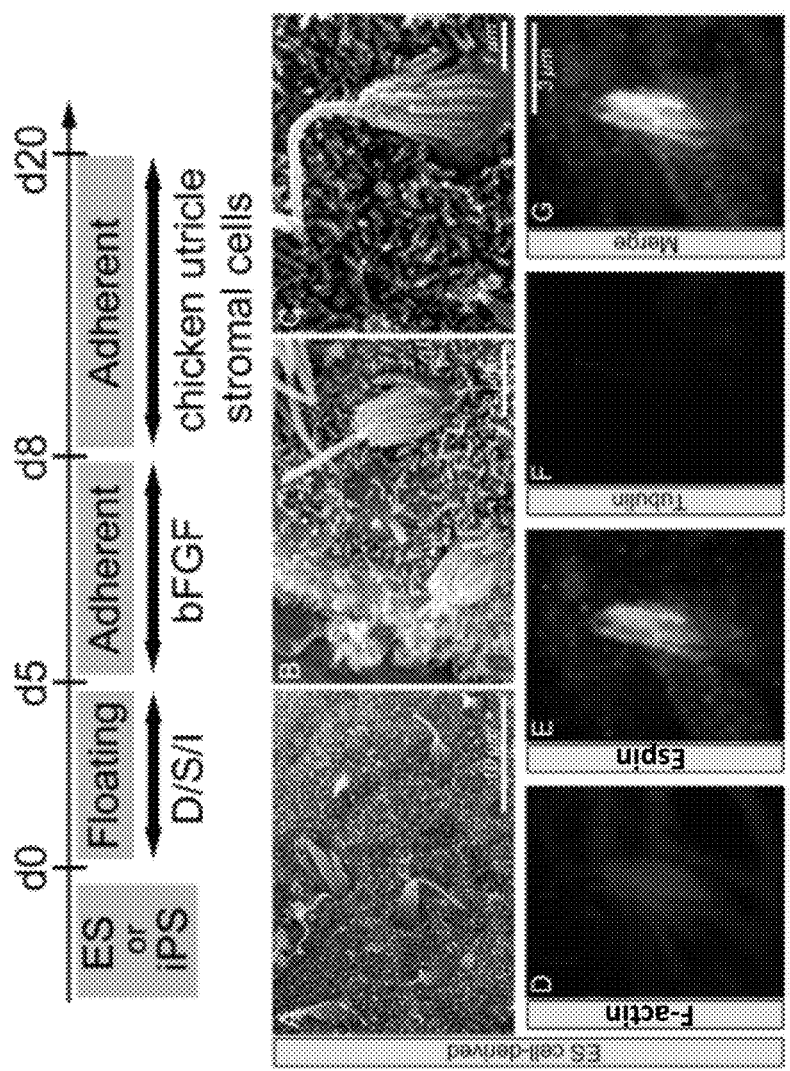
FIG. 20. Inner ear hair cell-like cell induction from mESC (see also FIGS. 10 and 11).
Figure 21:
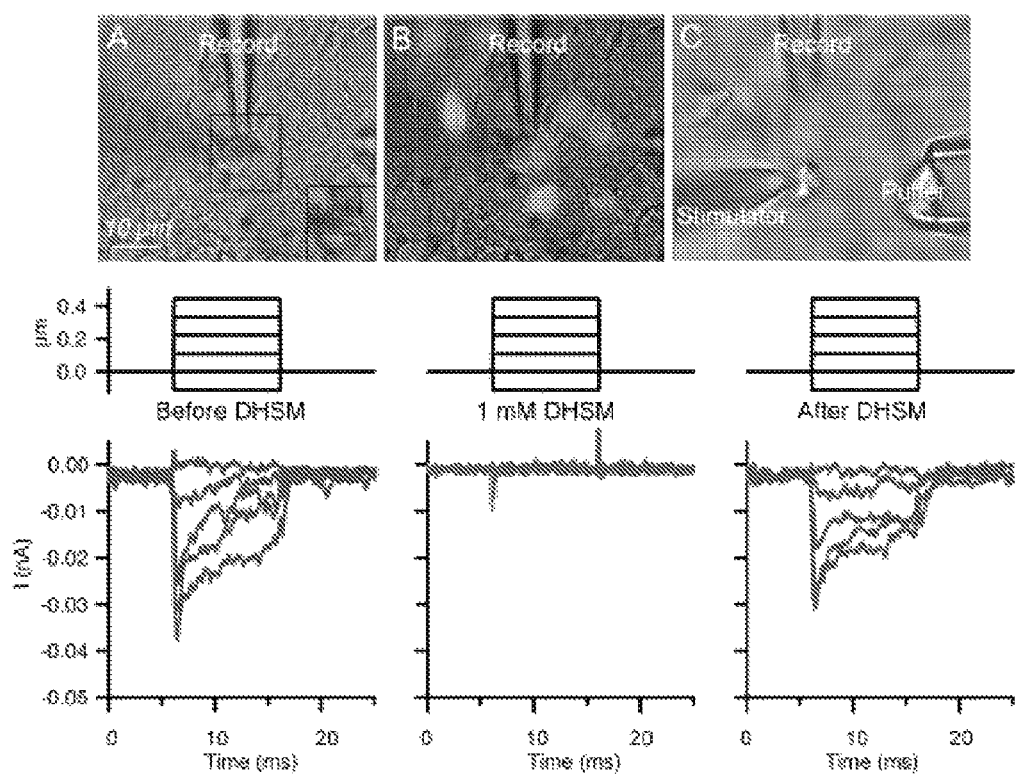
FIG. 21. Mechanotransduction of inner ear hair cell-like cells induced from mESC (see also FIG. 13).
Figure 22:
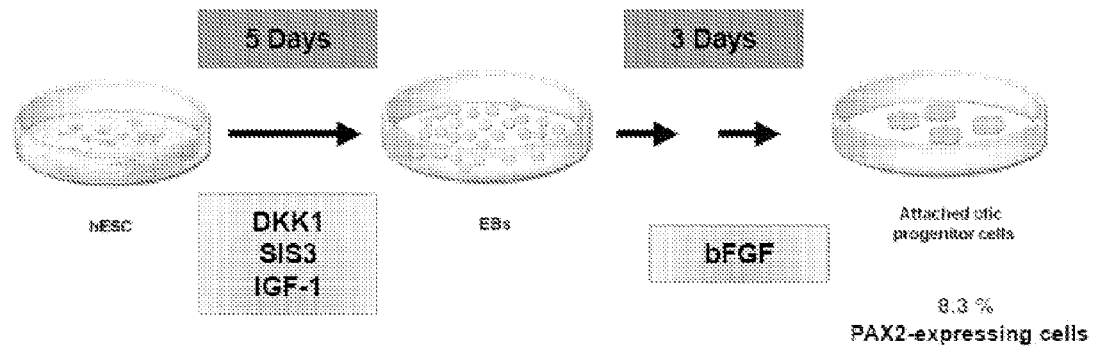
FIG. 22. Optimization of lengths of incubations with factors for culturing cell populations comprising otic progenitor cells from hESCs. (a) and (b). A culture that is enriched 8.3% for PAX2-expressing otic progenitor cells may be generated by the incubation of hESCs with DKK1/SIS3/IFG-1 for 5 days, followed by incubation of the resultant embryoid bodies comprising preplacodal ectodermal cells with bFGF for 3 days. (c) Modification of the duration of these incubation periods demonstrates that the most highly enriched cultures of Pax-2-expressing otic progenitor cells are arrived at by incubation of hESCs with DKK1/SIS3/IFG-1 for 5 days, followed by incubation of the resultant embryoid bodies comprising preplacodal ectodermal cells with bFGF for 6 days.
Figure 23A:
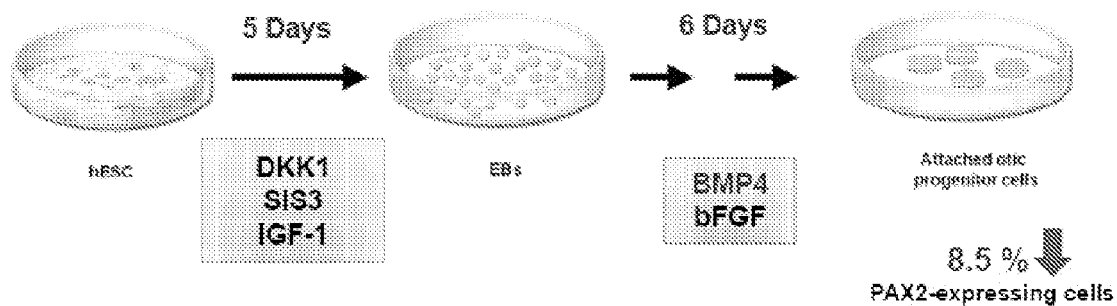
FIG. 23A-C. Culturing in the presence of different factors impacts the proportion of otic progenitor cells produced. (a) Culturing in the presence of BMP4 reduces the proportion of otic progenitor cells produced. (b) Culturing in the presence of Noggin during the induction phase of otic progenitor cell fate acquisition, and restricting the exposure of cells to BMP4 to the stabilization phase of otic progenitor cell fate acquisition increases the proportion of otic progenitor cells produced. (c) Culturing in the presence of R-spondin 1 during the induction phase of otic progenitor cell fate acquisition increases the proportion of otic progenitor cells produced.
Figure 23B:
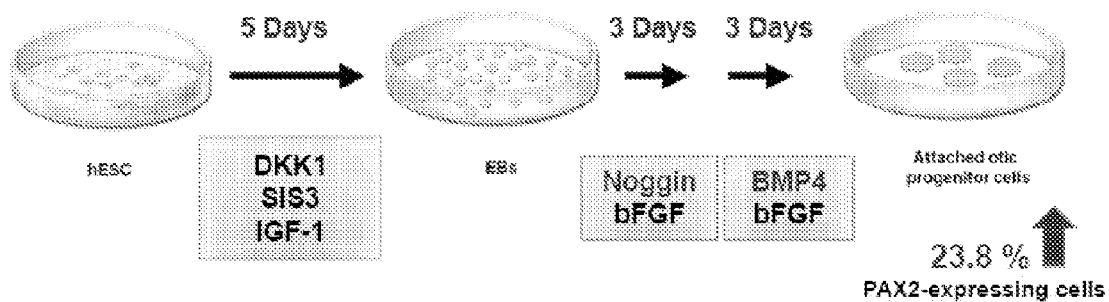
Figure 23C:
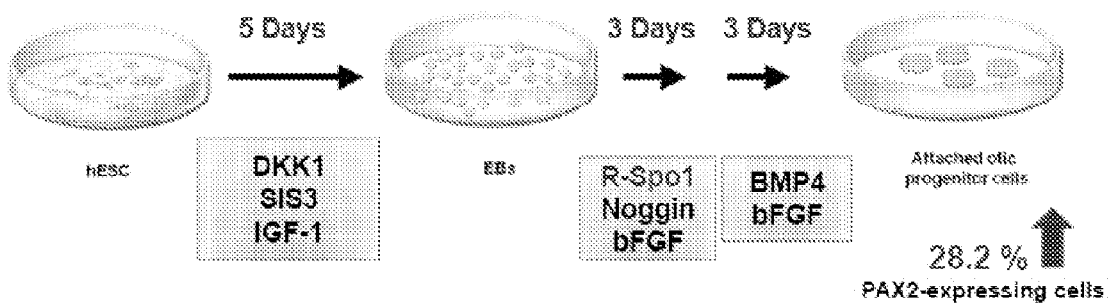
Figure 23D:
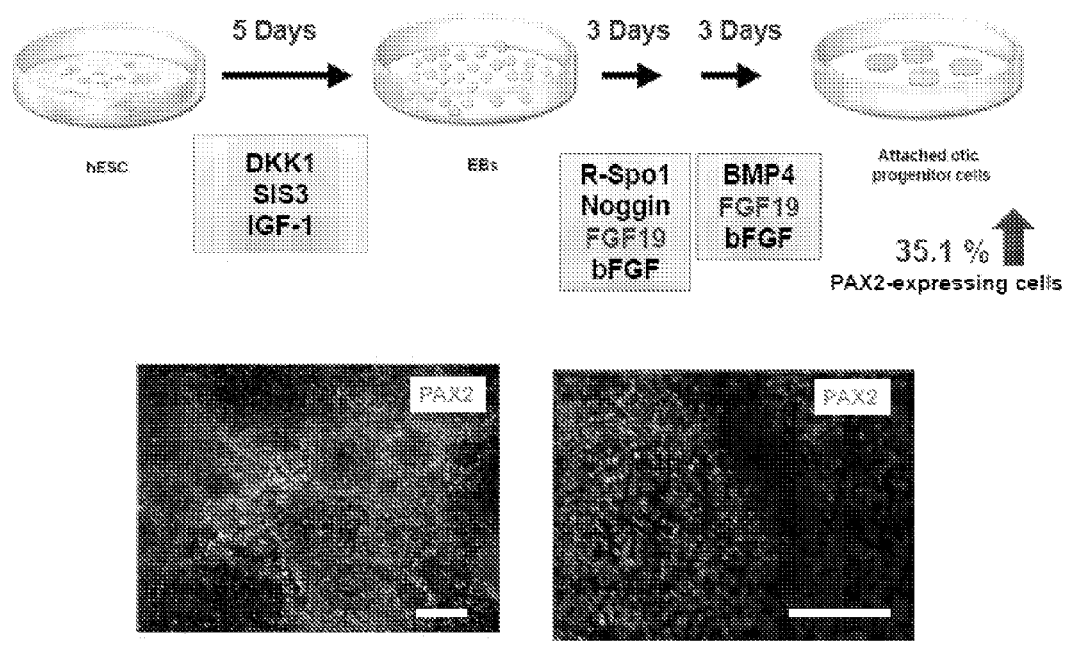
FIG. 23D. Culturing in the presence of FGF19 during both the induction phase and the stabilization phase of otic progenitor cell fate acquisition increases the proportion of otic progenitor cells produced.
Figure 24:
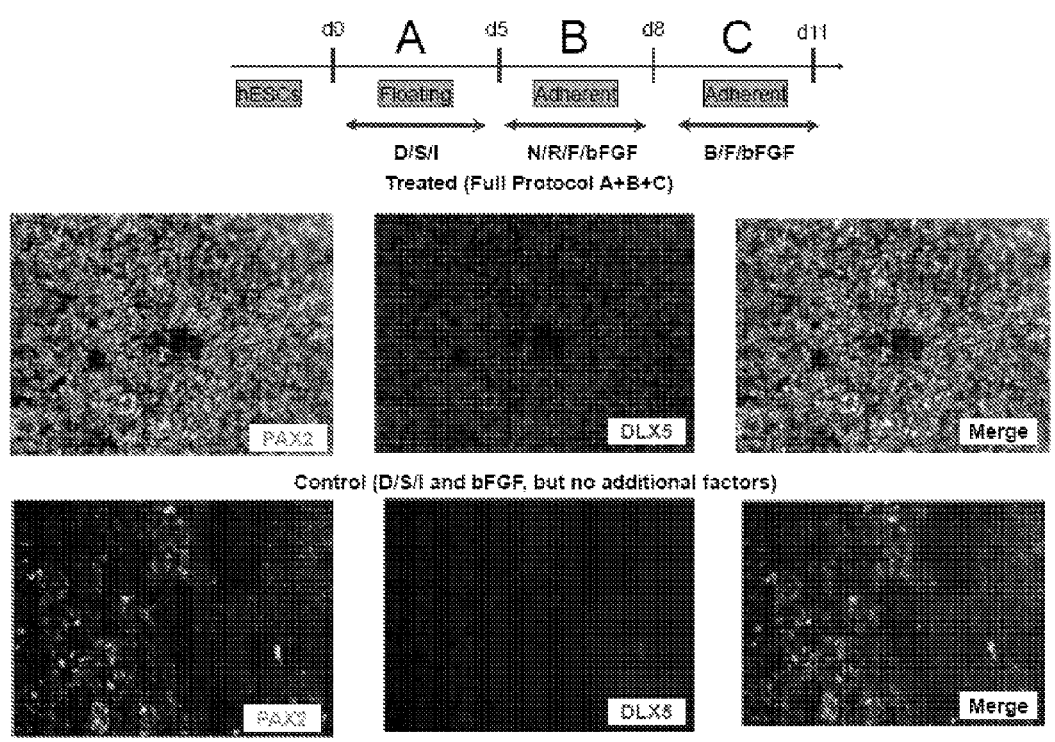
FIG. 24. Otic Induction from hESCs in the presence of bFGF plus additional growth factors (upper row) versus bFGF alone (lower row).
Figure 25:
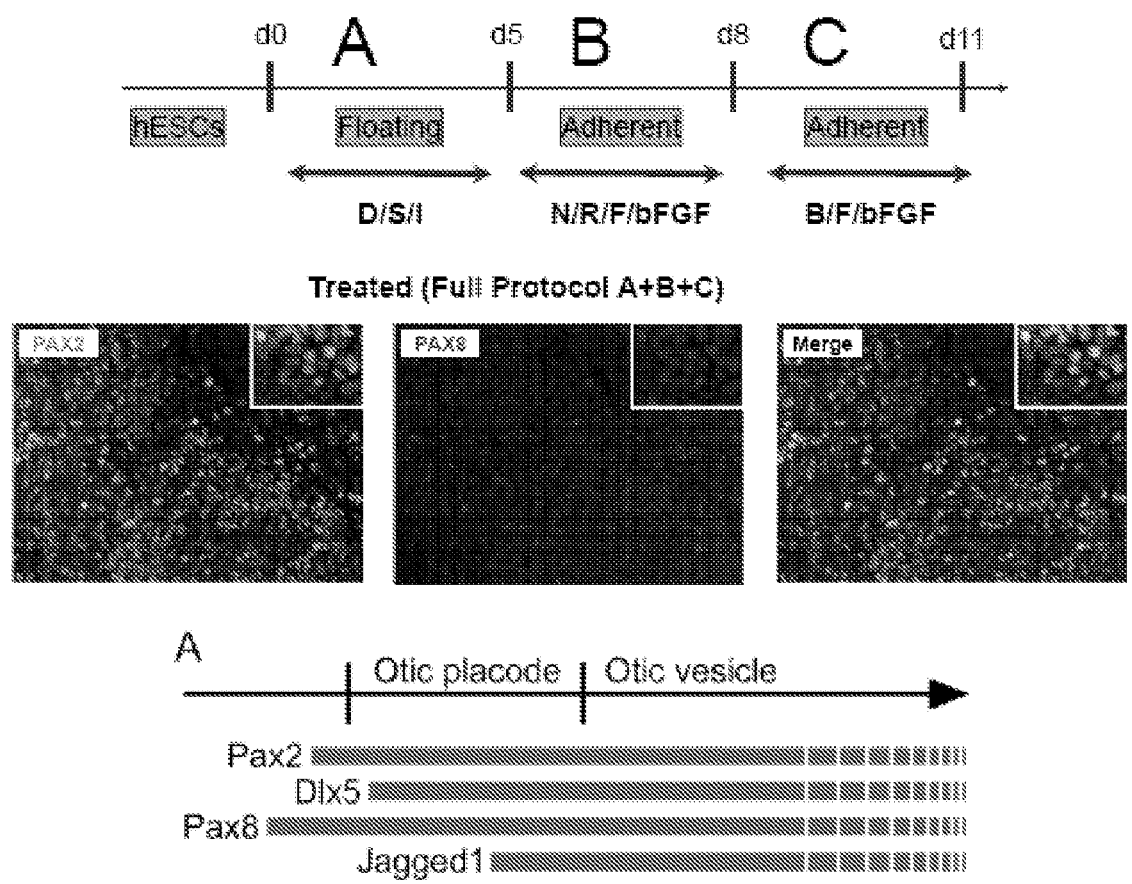
FIG. 25. Otic Induction from hESCs.
Figure 26:
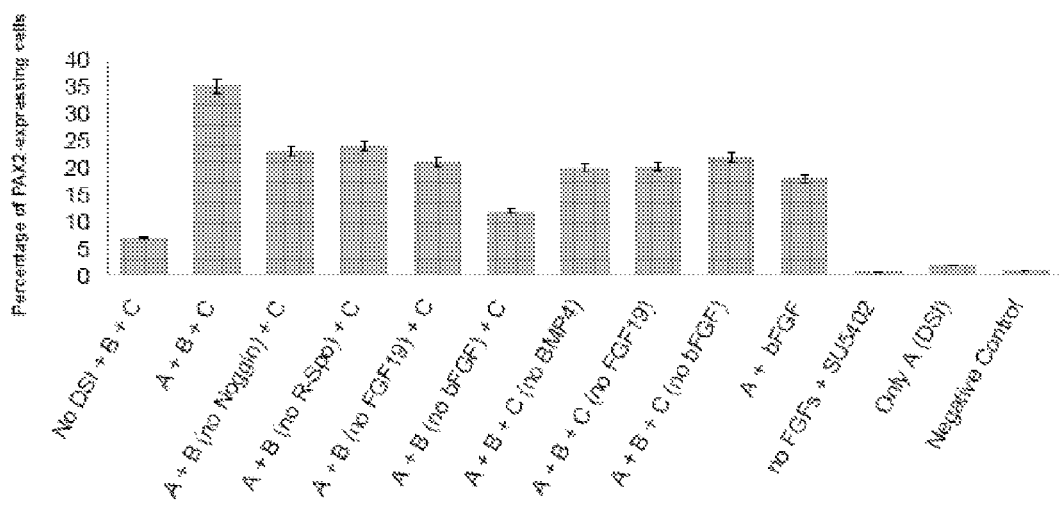
FIG. 26. Percentage of Pax2-expressing otic progenitor cells produced under different culture conditions. "A" represents the incubation of hESCs in the presence of DKK1/SIS3/IFG-1 ("D/S/I") to form preplacodal ectodermal cells. "B" represents the incubation of preplacodal ectodermal cells in the presence of Noggin/R-spondin1/FGF19/bFGF ("N/R/F/bFGF") to induce the formation of otic progenitor cells. "C" represents the incubation of induced otic progenitor cells in the presence of BMP4/FGF19/bFGF ("B/F/bFGF") to stabilize otic progenitor cell fate.
Figure 27:
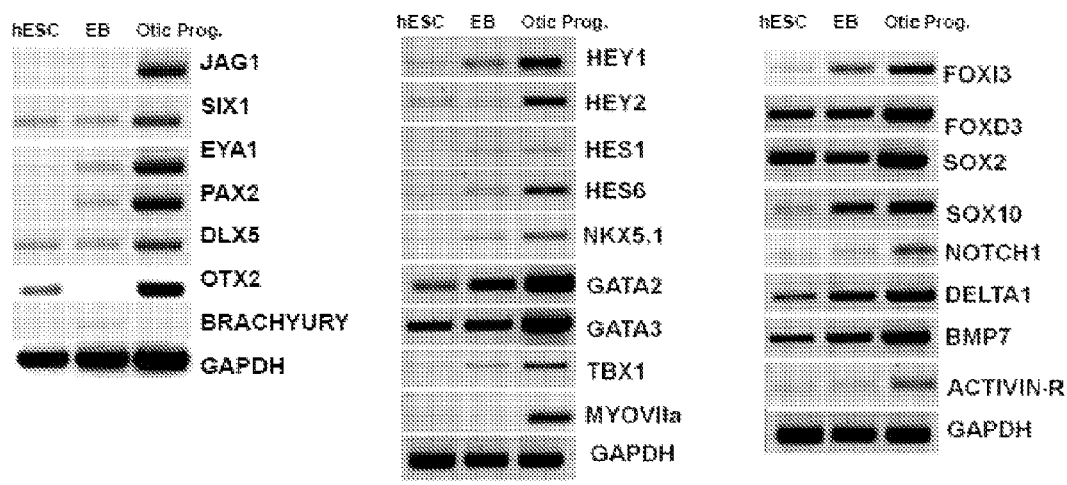
FIG. 27. Upregulation of otic progenitor cell markers. Expression of the indicated genes was assayed by RT-PCR.
Figure 28:
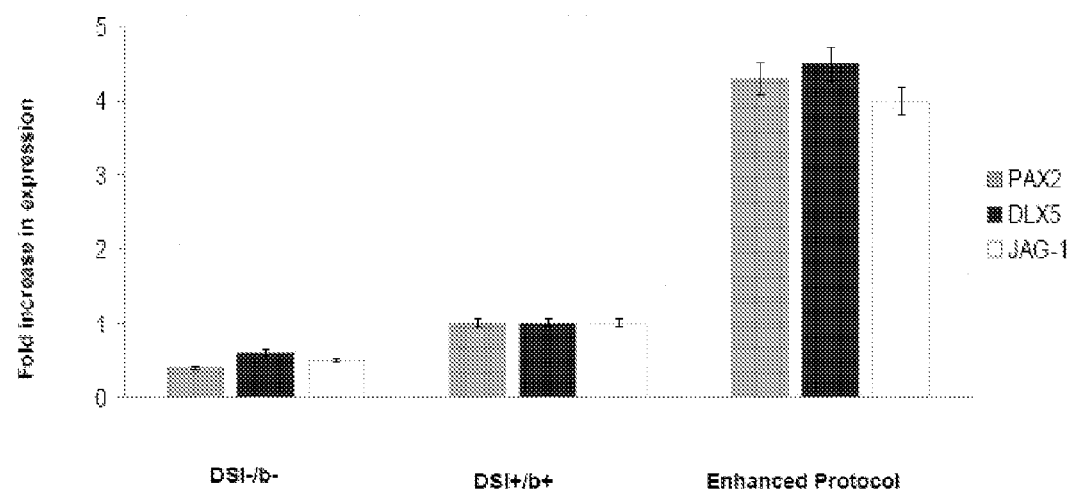
FIG. 28. Quantitative RT-PCR analysis of PAX2, DLX5 and JAG-1 in cultured otic progenitor cells.
Figure 29:
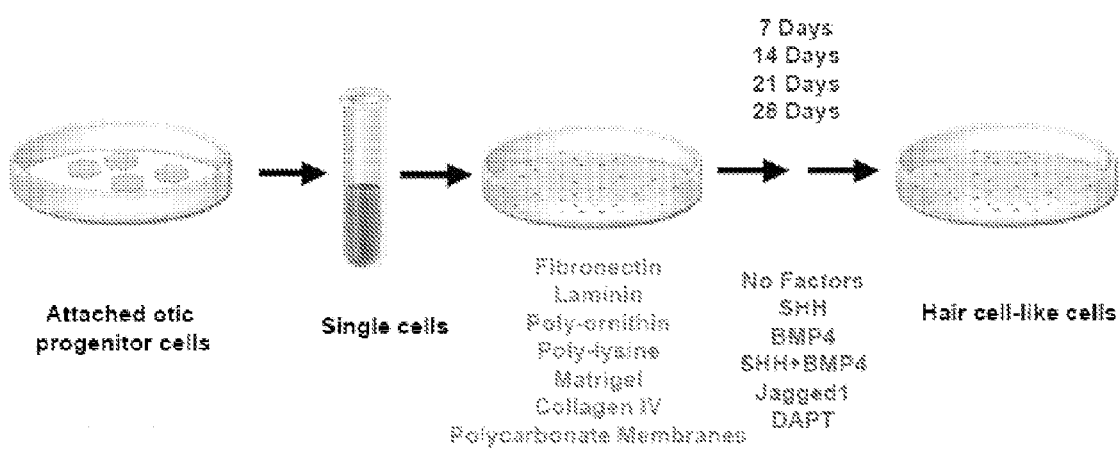
FIG. 29. Differentiation to hair cell-like cells in the absence of stromal cells. (A) Single cell suspensions of otic progenitor cells are cultured as a monolayer on a matrix composition such as fibronectin, laminin, poly-ornithin, poly-lysine, MATRIGEL™, collagen IC, or polycarbonate membranes. In some instances, cells are cultured in the presence of growth factors such as SHH, BMP, Jagged1 or DAPT in the early phase of culturing to expand the population of otic progenitor cells. In such cases, culture medium is then replaced with medium that does not contain growth factors, and the otic progenitor cells are allowed to differentiate into inner ear cells. (B) Single cell suspensions of otic progenitor cells are cultured as a monolayer on polycarbonate membranes in the presence of SHH to expand the population of otic progenitor cells. The culture medium is then replaced with medium that does not contain SHH or other growth factors, and the otic progenitor cells are allowed to differentiate into inner ear cells.
Figure 29:
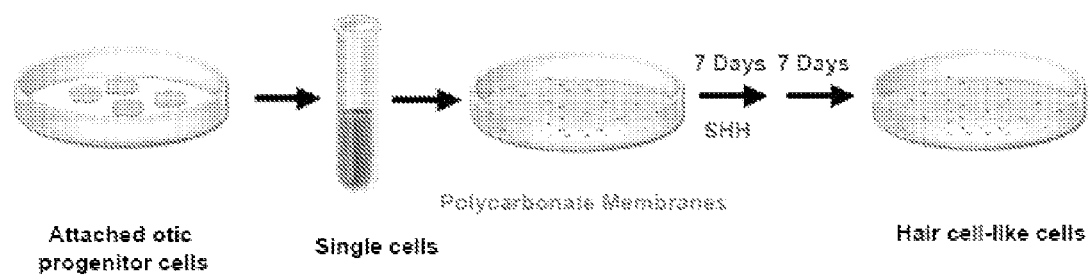
Figure 30:
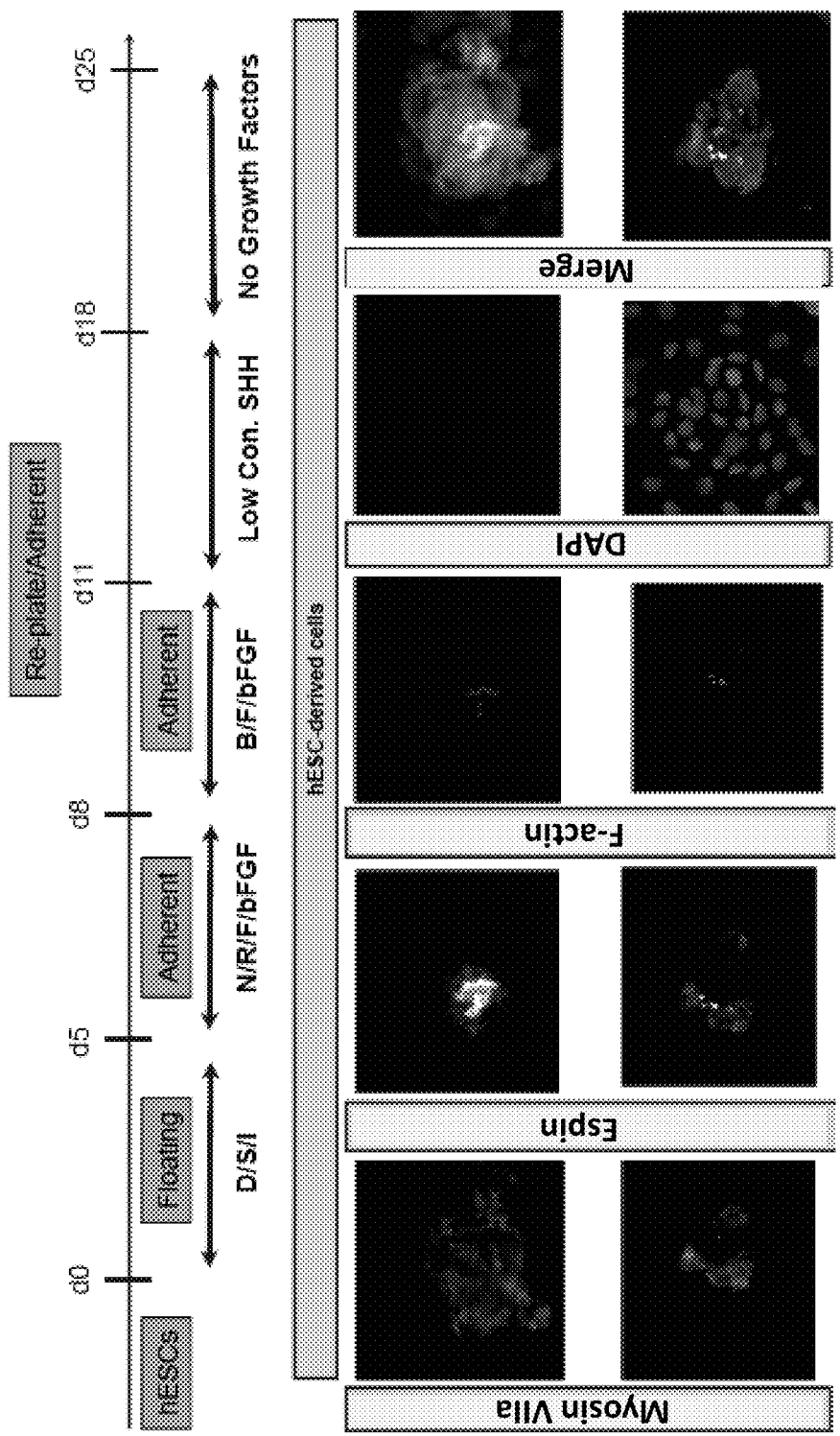
FIG. 30. Complete optimized protocol for the differentiation of hESCs to inner ear cells.

Voltage-dependent currents were also investigated in the same group of cells. Again, no differences between ESC- and iPSC derived cells were observed. A great deal of diversity was observed in the cell responses measured. FIG. 14 shows representative examples of the types of responses observed. Current magnitudes with K+ as the major intracellular ion ranged from 397 pA to 4982 pA with a mean of $2190\pm1595$ pA (n=24). Cells shown in FIG. 14A are distinguished by the presence of an inward current, likely Na+, where ten out of 30 cells tested were positive for this current. FIG. 14C shows an expanded view of the initial current response for a cell with an inward current. Additionally, two major types of outward currents were observed, those that activated rapidly and showed some level of inactivation and those that activated more slowly with little inactivation. The predominant response was a slowly activating, noninactivating conductance with no inward current. Most cells showed components of each to different degrees. Steady-state activation properties also varied considerably with half activating voltages ranging from 17 mV to 23 mV with the more negative activation associated with the inactivating currents, and the more depolarized with the more slowly activating, noninactivating currents. Experiments with Cs+ replacing K+ revealed two kinetically distinct components that were carried by Cs+ (FIG. 13B). About half of the cells had a rapidly activating component, while about 20% had a more slowly activating current, and 30% had no Cs+-permeant component at all.

Discussion

In this study, we utilized principles of early development to suppress the differentiation of ESCs and iPSCs along endo- and mesodermal lineages. The resulting presumptive ectoderm displayed competence to respond to otic-inducing FGFs. The generated otic progenitor cells were capable of differentiation into hair cell markerexpressing cells, independent of the substrate they were cultured on. The development of cytomorphological specializations, such as hair bundle-like protrusions, however, required coculture with fibroblast-like cells that were isolated from embryonic chicken utricles after removal of the sensory epithelial layers. In these cultures, the hair cell-like cells were organized in clusters, displayed hair bundle-like protrusions, and were surrounded by cells that showed features of inner ear supporting cells. Upon mechanical stimulation of bundles, the cells responded with currents reminiscent of immature hair cell transduction currents. Other currents detected in the young hair cell-like cells were variable in type and size. This observation suggests that voltage-dependent currents that are diagnostic for specific mature hair cell subtypes develop independently from hair bundles and mechanoelectrical transduction. We found no substantial differences between ESCs and iPSCs with respect to their ability to differentiate along the otic lineage or their differentiated hair cell-like function.

Guidance of ESCs and iPSCs toward the Otic Lineage.

Pluripotent cells were guided in a step-wise manner toward an otic fate. Exposure to bFGF or FGF3/10 revealed that embryoid bodyderived cultures, which were treated with Dkk1, SIS3, and IGF-1, were substantially more responsive to otic inducers than cultures that were only treated with Dkk1 and SIS3. IGF-1 therefore seems to anteriorize the ectoderm that was generated during embryoid body formation, increasing the number of cells capable of responding to otic-inducing FGFs. This anteriorizing effect of IGF signaling was previously observed in developing Xenopus embryos (Pera et al., 2001), used to promote anterior development of ESCs (Lamba et al., 2006), and increased responsiveness of anterior ectoderm to otic induction was reported in chicken embryos (Groves and Bronner-Fraser, 2000). It is interesting that the same logic that we applied to generate ectoderm that is responsive to inner ear inducers was utilized to guide ESCs toward retinal fate (Ikeda et al., 2005; Lamba et al., 2006; Osakada et al., 2008). In the case of retinal development, Pax6-positive precursors, often organized in neural rosettes, were observed. Our cultures also harbored Pax6-expressing cells that often occurred in rosettes (FIG. 7C). These Pax6-positive cells were clearly distinct from the Pax2-expressing inner ear progenitor cells, indicating that retinal and otic lineages appeared to develop independently in D/S/I and bFGF treated cultures.

Beside FGF signaling, activation of the canonical Wnt pathway has been proposed to further promote otic commitment of Pax2-expressing cells of the FGF-dependent pre-otic field of the chicken embryo (Ohyama et al., 2006). We did not observe an increase in the ability or efficiency of D/S/I and bFGF-treated cultures to generate hair cell-like cells when we supplemented the differentiation cultures with recombinant Wnt3a or LiCl (data not shown). An explanation for this result is that the cultures might already produce sufficient levels of Wnts. This speculation is supported by the observation that otic commitment, revealed by differentiation of hair cell marker-expressing cells, happens in the cultures without adding additional factors.

We previously have generated Pax2-expressing otic progenitors by using a protracted protocol that was based on selective survival of progenitors (Li et al., 2003). These cells were able to differentiate along the otic lineage after withdrawal of growth factors, and they displayed hair cell morphology when they were grafted into the developing inner ear of chicken embryos. In general, sensory cell types such as hair cell-like and photoreceptor-like cells generated by in vitro guidance of ESCs or, more recently, iPSCs (Hirami et al., 2009; Meyer et al., 2009) were characterized by immunocytochemistry. In-depth ultrastructural analysis of cytomorphological specializations and direct functional testing has not been applied to these cells. To test for these specializations and for function, we needed to determine culture conditions that promote the generation of hair bundles. Maintaining D/S/I and bFGF-treated ESCs and iPSCs on various substrates including fibronectin, gelatin, and MEF feeder cells confirmed that in vitro-generated otic progenitors are able to upregulate the hair cell marker myosin VIIa. Development of hair bundle-like structures and expression of hair bundle proteins such as espin (Zheng et al., 2000), however, did not occur on these substrates. We hypothesized that the cells need additional signals and we tested whether expanded embryonic chicken utricle stromal cells would be able to provide such signals. Both ESC- and iPSC-derived otic progenitor cell cultures responded to stromal cells by organizing into clusters that were reminiscent of inner ear sensory epithelia (FIG. 10). Experiments with stomal cell conditioned medium and coculture with fixed stromal cells indicate that the hair bundle-inducing activity is not present in conditioned media and that it is abolished by paraformaldehyde fixation. These results are compatible with a surface-linked and fixation-sensitive signal, but they do not exclude multiple factors or other more complex scenarios.

How Hair Cell-Like are ESC- and iPSC-Derived Hair Cell-Like Cells?

Coculture with utricle stromal cells led to formation of F-actin filled protrusions that were immunopositive for the hair bundle protein espin and single tubulin-filled kinocilia in cells that coexpressed myosin VIIa and nGFPAtoh1. When we analyzed clusters of nGFP-positive cells by SEM, we found an organization of hair bundle-bearing hair cell-like cells surrounded by cells that displayed short microvilli, reminiscent of hair and supporting cells. Hair bundles displayed many other features, such as interciliary links, asymmetric stereociliary tops, and filamentous links from stereociliary tops to the neighboring stereocilia, tapering at the base, and immunoreactivity to antibodies to cadherin 23. Although the hair bundles were of various shapes, we did not detect typical mature cochlear bundle morphologies. The bundle morphologies appeared more generic, as if specificity had not yet been assigned.

Current responses obtained from mechanically stimulated bundles were similar to those obtained from immature hair cells where the currents were small, current-displacement functions were broad, the presence of adaptation and the rates measured were quite variable, and directional sensitivity was often absent (Lelli et al., 2009; Michalski et al., 2009; Waguespack et al., 2007). The time course of maturation of mechanotransduction varies depending both on end organ and on location within the end organ such that in mammalian cochlea basal cells mature 2-3 days earlier than apical outer hair cells. Mechanotransduction in basal outer hair cells begins at postnatal day 0. Vestibular hair cells mature in waves but begin neonatally around E16 (Geleoc and Holt, 2003). A common feature of the maturation is that the current amplitudes begin small, less than 100 pA; adaptation is nonexistent or slow, progressively becoming faster and more complete; and directional sensitivity is initially absent, becoming progressively more apparent (Waguespack et al., 2007). Maturation of the current responses takes about 5 days (Waguespack et al., 2007). Measurements presented here would suggest that mechanotransduction was within 2 days of the maturation process, with the variability in responses indicating a range of maturation of up to about 2 days.

Both the morphological and electrophysiological data suggest a common signaling pathway to trigger the development of a mechanosensitive hair bundle; however, additional signaling is required to specialize the bundle as well as to specify hair cell subtypes such as auditory or vestibular, inner or outer hair cell, or type I or type II hair cell. Supporting the argument that additional signaling is required to further specialize cells to specific phenotypic hair cells were the wide range of basolateral responses observed. The array of voltage-dependent currents measured suggest a distinct lack of appropriate signaling needed to promote complete maturation into specific hair cell subtypes. In both auditory and vestibular hair cells, there is a pattern of maturation where cells have a particular set of outward currents that include outward potassium (though limited selectivity) and inward sodium currents (Geleoc et al., 2004; Marcotti et al., 1999; Marcotti et al., 2003; Marcotti and Kros, 1999; Oliver et al., 1997). Both of these are transiently expressed and replaced by more selective channel types that vary depending on hair cell type and location within the end organ. Because of this diversity of channels, present data do not allow for the type of hair cell to be identified. As already pointed out, the lack of specificity in the basolateral conductances does suggest that hair bundle formation and development of mechanoelectrical transduction occurs independently of basolateral subtype specification.

Our findings provide a useful assay to study signals involved in hair cell subtype specification, a topic that is largely unexplored, particularly in mammals. Likewise, the guidance method outlined here offers a platform for molecular studies on hair cells, which are difficult to obtain in large numbers. A single retina, for example, harbors more than 120 million photoreceptors that can be isolated fairly easily, whereas a single mammalian inner ear only yields a few tens of thousand hair cells, which are difficult to dissect. The fact that in vitro-generated hair cell-like cells display mechanosensitivity demonstrated that generation of replacement hair cells from pluripotent stem cells is feasible, a finding that justifies the development of stem cell-based treatment strategies for hearing and balance disorders.

Example 2

Generation of Human Inner Ear Sensory Hair Cells and Supporting Cells from Embryonic Stem Cell-Derived Otic Progenitor Cells Human embryonic stem cells are cultured in non-adherent conditions for a defined period of time (5-20 days, and preferably about 15 days) in a series of knockout serum replacement (KSR) Differentiation Media comprising a stepwise reduction in knockout serum replacement (KSR) (20% KSR for days 1-6), 15% KSR for days 7-12) and 10% KSR for days 13-15) and factors or compounds added that a) suppress the formation of endodermal and mesodermal cells, thereby enriching for ectodermal cell fate, and b) rostralize/anteriorize the cell population. Examples of factors and compounds that are effective for (a) include but are not limited to inhibitors of TGFbeta signaling such as SIS3 (specific inhibitor of Smad3) and inhibitors of Wnt signaling such as Dkk1, Fz8-Fc, or a small compound inhibitor such as IWP2. Examples of rostralizing factors for the purpose mentioned (b) would include such factors as IGF-1 and insulin. The result of this step is embryoid bodies that are enriched for ectodermal cells that are competent to respond to otic-inducing conditions. An enrichment of ectoderm that is competent to respond to otic induction may follow, e.g. by flow cytometric sorting with high or low throughput sorters in conjunction with specific cell surface markers. Cell surface markers include but are not limited to FGFR1, FGFR2, and FGFR3. Further enrichment may be achieved by using markers that are expressed on non-competent cells (negative enrichment).

The cells are then plated on Polyornithin/Laminin/Fibronectin-coated cell culture plastic dishes or membranes that include but are not limited to polycarbonate membranes, e.g. MILLIPORE ISOPORE™ membranes, in densities that allow monolayers to form. The cells are induced to begin to differentiate into otic progenitor cells over a period (2-5 days, and usually about 3 days) of culture in 10% KSR Differentiation Media and defined adherent conditions in the presence of BMP inhibitors (e.g. Noggin, Chordin, Dorsomorphin), Wnt signaling activators (e.g. Wnts, R-spondin1, GSKbeta modulators), FGF19, and FGF2 or combinations of other FGF growth factors that have been shown to play roles in otic induction (FGF3, FGF8, FGF10). As a result, the cells begin to express otic marker genes such as PAX2, PAX8, DLX5, OTX2, EYA1, SIX1, and JAG1.

A subsequent culturing step of about 2-5 days, and more usually 3 days, in the presence of combinations of BMPs or other TGFbetas, FGF19, and FGF2 or combinations of other FGF growth factors that have been shown to play roles in otic induction (FGF3, FGF8, FGF10) serves to stabilize the otic progenitor cell fate. The resulting cells stabilize expression of markers mentioned in the induction step above and also express/upregulate one or more of: FOXI3, SOX2, NOTCH1, DELTA1, BMP7, TBX1, GATA3, MYOVIIA, FOXD3, HEY1, HEY2, HES1, HES6, SOX10, ACTIVIN-R, NKX5.1. In the absence of any mechanical enrichment steps, the otic progenitor cell population that is produced will comprise about 35% marker-positive cells. Markers include the genes mentioned but are not limited to those described above.

In some instances, it may be desirable to enrich for the otic progenitor cells, for example by flow cytometric sorting with high or low throughput sorters in conjunction with specific cell surface markers. Cell surface markers include but are not limited to FGFR1, JAG1, DELTA1 and NOTCH1. Further enrichment is achieved by using markers that are expressed on non-otic cells (negative enrichment).

Otic progenitor cells may then be cultured in defined media for about 1-5 days, usually about 3 days, in 10% KSR Differentiation Media to promote expansion of the otic progenitor cell pool. SHH may or may not be added to promote proliferation. An additional culturing step may also be performed here, in which the cells are cultured for a defined period of time (usually 1-5 days, e.g. 2-4 days, preferably 4 days) in 10% KSR Differentiation Media comprising activators of BMP signaling, e.g. BMP4, and activators of FGF signaling, e.g. bFGF. The otic progenitor cells divide during this time period.

To induce the differentiation of the otic progenitor cells to inner ear cells, the otic progenitor cells are cultured for a period of 9 or more days in the absence of factors. For the first several days of this step (e.g. days 1-8, usually about days 1-6) the cells are cultured in 5% KSR Differentiation Media. For the latter days in this step (e.g. the last 1-5 days, usually the last about 3 days), the cells are cultured in 0% KSR Differentiation Media. The resulting cell population consists of undefined cells and of epithelial clusters of cells that express either inner ear supporting cells markers (P27(KIP1), PROX1, OTOA, or other markers) or cells that express inner ear sensory hair cell markers (HATH1, MYO6, MYO7A, ESPIN, or other markers). A fraction of the hair cells are functional and sensitive to ototoxic insults. Supporting cells either do not divide or divide only sporadically.

Screens may be conducted on the clusters of supporting cells and hair cells that are generated in the last step. Screens consist of testing whether a compound is toxic to hair cells (ototoxic), or whether a compound protects hair cells from other ototoxic insults such as aminoglycoside antibiotics or cisplatin or related substances, or whether a compound initiates regeneration of hair cells after or without preceding ototoxic treatment, measured by proliferation of supporting cells and re-occurrence of cells that express markers for hair cells.

It will be readily apparent to those of ordinary skill in the art in light of the teachings of this invention that certain changes, variations and modifications may be made thereto without departing from the spirit or scope of the appended claims. Such modifications include further enrichment of cells after each individual step such with flow cytometry, immunodepletion, or microfluidics-based technology; expansion of progenitor cells after individual steps; combination of enrichment and expansion and/or replacement of membranes of the last step with other substrates.

Materials and Methods

Media used for maintenance and otic differentiation of hESCs is listed in tables 2-6:

TABLE 2

HES media

|  | Volume (ml) |
|---|---|
| Knock out DMEM/F12 | 390 |
| KSR | 100 |
| Non-essential amino acid solution | 5 |
| Glutamax | 5 |
| 2-ME | 0.008 |

TABLE 3

20% KSR Differentiation Media

|  | Volume (ml) |
|---|---|
| GMEM | 375 |
| KSR | 100 |
| Non-essential amino acid solution | 5 |
| Pyruvate | 5 |
| N2 | 5 |
| B27 | 10 |

TABLE 4

15% KSR Differentiation Media

|  | Volume (ml) |
|---|---|
| GMEM | 400 |
| KSR | 75 |
| Non-essential amino acid solution | 5 |
| Pyruvate | 5 |
| N2 | 5 |
| B27 | 10 |

TABLE 5

10% KSR Differentiation Media

|  | Volume (ml) |
|---|---|
| GMEM | 425 |
| KSR | 50 |
| Non-essential amino acid solution | 5 |
| Pyruvate | 5 |
| N2 | 5 |
| B27 | 10 |

TABLE 6

0% KSR Differentiation Media

|  | Volume (ml) |
|---|---|
| GMEM | 475 |
| Non-essential amino acid solution | 5 |
| Pyruvate | 5 |
| N2 | 5 |
| B27 | 10 |

Handling of Human ES Cells and Initial Differentiation Steps.

Human ESCs require careful handling and daily maintenance. Dissociation of the cells into single cells should be avoided because the cells may die. Cultures are maintained at 37° C. in a humidified atmosphere of 5% $CO_2$. Cell passage is performed mechanically with needles. In our protocol for differentiation, hESCs colonies are dissociated into 5-20 cells per clump.

Low passage number hESCs are grown on mouse embryonic fibroblast (MEF) feeder layers. Before differentiation, the cells are passed several times in feeder-free conditions on MATRIGEL™-treated plates to avoid MEF cell to be present in further differentiation steps. To establish defined culture conditions for human ES cell unlike mouse ES cells, we do not include fetal bovine serum (FBS) in our media. Instead, we use knock-out serum replacement (KSR). For differentiation, hESCs are incubated in the presence of Dkk-1 and SIS-3 and IGF-1 for 15 days in a floating culture and are subsequently plated onto Laminin-, Fibronectin-, and Poly-ornithin-coated dishes, which support adhesion of cell aggregates and subsequent differentiation. Plating a high density of cells is not recommended for long-term cultures since the cells could become overly confluent. In the adherent culture system, differentiating cells will migrate out from the aggregates.

Human ES cells are maintained as described. The cells are cultured on mouse embryonic fibroblasts (MEFs), colonies are cleaned daily from differentiating cells, and passed every 5 to 7 days.

Figure 31:
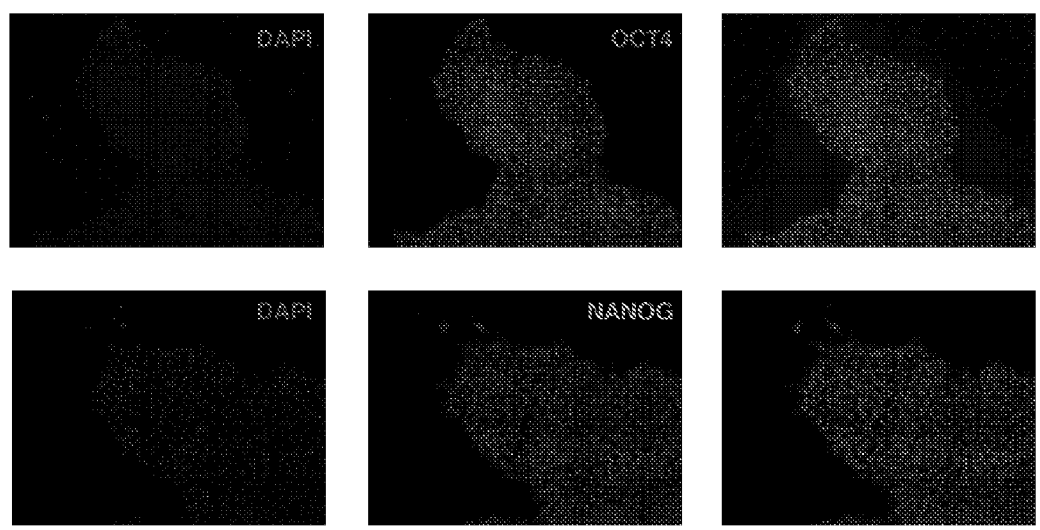
FIG. 31. hESCs grown on MATRIGEL™, quality controlled with antibody staining for Oct4 and Nanog.

To generate a pure hESC population at the onset of the experiment, the cells are passed to MATRIGEL™-coated dishes. On MATRIGEL™, the hESCs are grown in freshly conditioned media taken daily from MEF cultures, and are passed every 4-6 days. Immunohistochemistry for Oct4 and Nanog serves as a quality control for hESCs (FIG. 31).

Differentiation of Human ES Cells Toward Otic Progenitors.

At day 0 (D0), the media is aspirated from the feeder-free hESCs culture 6-well dishes and 2 ml of PBS is added into each well. The PBS is then aspirated and 2 ml of pre-warmed Dispase mix is added. The cells are incubated at 37° C. for 5-7 min. The cells are monitored with an inverted microscope to verify that the edges of the colonies are starting to detach.

Using a cell scraper, the colonies are carefully scraped and detached mechanically. The detached cell clumps are carefully transferred to a 15 ml tube and centrifuged at 150 g for 5 min. The supernatant is aspirated and an appropriate amount of HES media containing DKK1 (5-100 ng/ml), IGF-1 (1-10 ng/ml) and SIS-3 is added at 1-30 µM to the cell pellet. The dish is incubated at 37° C. in a humidified atmosphere of 5% $CO_2$.

The cells are dissociated into clusters of ~10-20 cells with gentle pipetting. A 5 ml glass pipet is used, and the cells are pipetted for 4 to 6 times. The cell suspension is plated onto a 6-well plate of an ultra-low adhesive cell culture plate at a density of 30-100 clusters per well. The dish is incubated at 37° C. in a humidified atmosphere of 5% $CO_2$.

Producing Preplacodal Ectodermal Cells.

Figure 32:
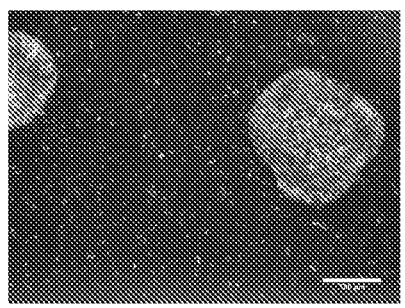
FIG. 32. hESCs on MATRIGEL™ at day 0 and EBs on day 4.
Figure 32:
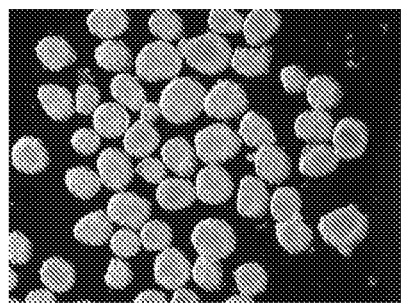

At day 3, the media is replaced with 20% KSR Differentiation media comprising DKK1 (5-100 ng/ml), IGF-1 (1-10 ng/ml) and SIS-3 (1-30 µM). This can be done by collecting all the embryoid bodies (EBs) into a 15 ml tube and allowing the EB to sink by gravity. The supernatant is carefully aspirated, and fresh media is added to the EBs. EBs are then transferred back into a well of an ultra-low adhesive 6-well plate. FIG. 32 provides an image of EBs in culture at this time.

On day 6 and 9, the media is replaced with 15% KSR Differentiation media containing DKK1 (5-100 ng/ml), IGF-1 (1-10 ng/ml) and SIS-3 (1-30 μM). This can be done as explained earlier by collecting all the embryoid bodies (EBs) into a 15 ml tube and allowing the EB to sink by gravity. The supernatant is carefully aspirated, and fresh media is added to the EBs. EBs are then transferred back into a well of an ultra-low adhesive 6-well plate.

On day 12, the media is replaced with 10% KSR Differentiation media containing DKK1 (5-100 ng/ml), IGF-1 (1-10 ng/ml) and SIS-3 (1-30 μM). This can be done as explained earlier.

Induction of Otic Progenitor Cells.

At day 15, EBs are transferred into a 15 ml tube and allowed to sink to the bottom of the tube by gravity. 10% KSR Differentiation Media comprising 10% KSR (knock-out serum replacement), bFGF (5-25 ng/ml), FGF19 (5-25 ng/ml), Rspondin-1 (5-50 ng/ml), and Noggin (5-100 ng/ml) is added. EBs are transferred into a Laminin-, Fibronectin-, Poly-ornithin-coated chamber slide at 5-7 aggregates per well. Half of the media is replaced every day thereafter with freshly prepared media.

Stabilization of the Otic Progenitor Cell Fate.

At day 18, all of the media is replaced with 10% KSR Differentiation Media comprising bFGF (5-25 ng/ml), FGF19 (5-25 ng/ml) and BMP4 (1-20 ng/ml). Half of the media is replaced every day thereafter with freshly prepared media.

Figure 33:
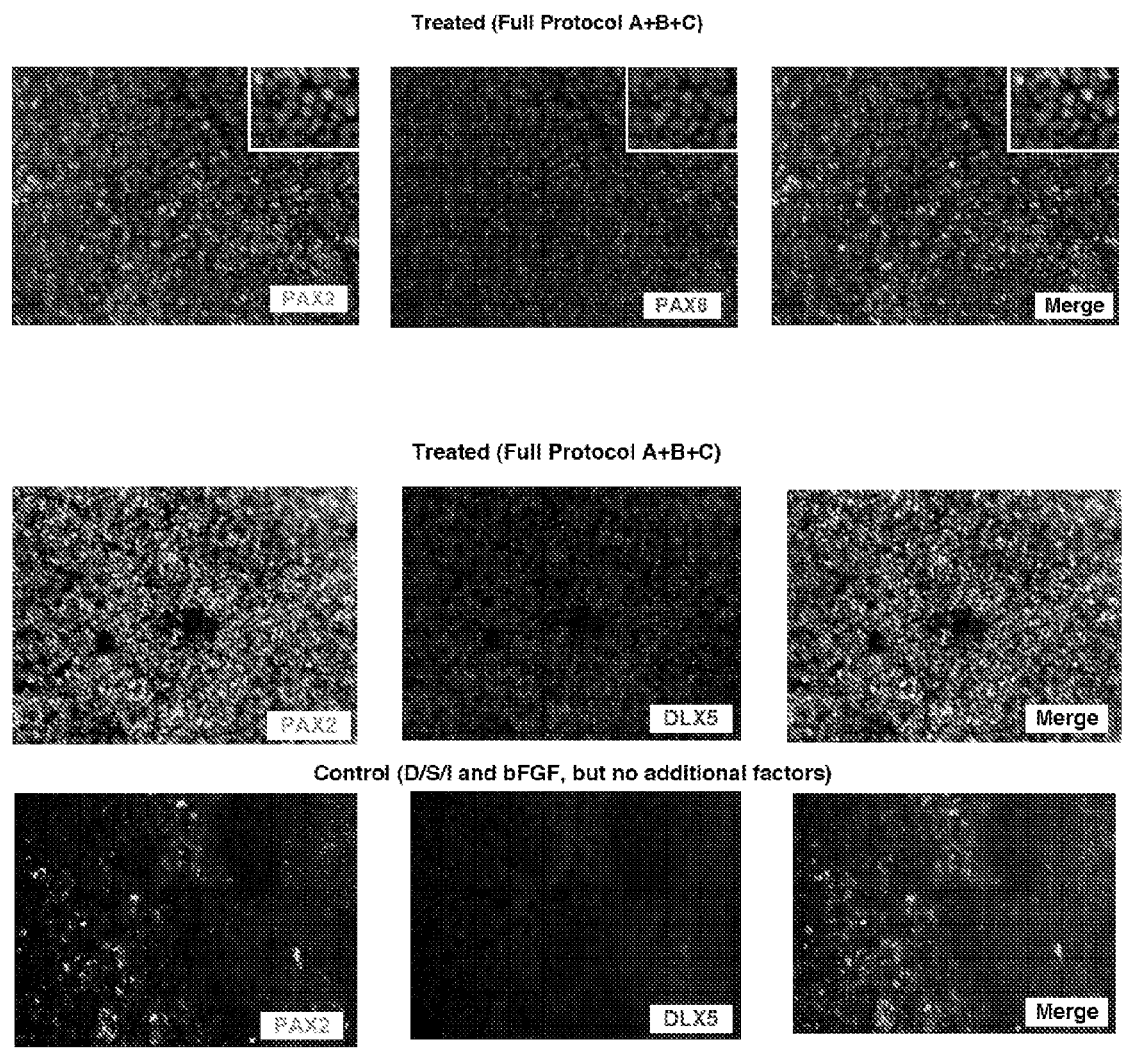
FIG. 33. Human ES cell-derived otic progenitor cells stained for Pax2, Pax8 and Dlx5.
Figure 34:
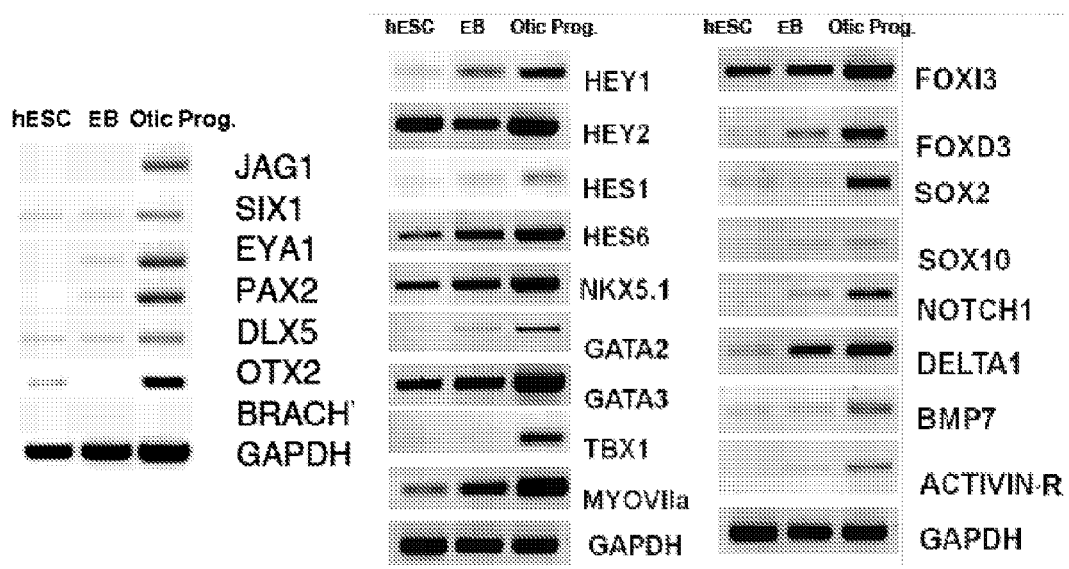
FIG. 34. Semi-quantitative RT-PCR of various otic markers on hESCs, EBs, and otic progenitor cells on day 11.

At day 21, a large fraction of the cells expressed otic progenitor cell markers. Quality control experiments demonstrating this are shown in FIGS. 33 and 34. These include an immunohistochemical assessment of expression of Pax2, Pax8 and Dlx5 in human ES cell-derived otic progenitor cells (FIG. 33), and an assessment of the expression of various otic markers on hESCs, EBs, and otic progenitor cells on day 11 by semi-quantitative RT-PCR (FIG. 34). Primers used in the RT-PCR reaction are listed in table 7 below.

TABLE 7

Primers used for RT-PCR on human cells.

| GENE NAME | SEQUENCE | SEQ ID NO. |
|---|---|---|
| SIX1 F | TCACCACCACCCAGGTCAGC | 29 |
| SIX1 R | CCCTGCAGCAGAAGGACCGA | 30 |
| EYA1 F | CGCGTACCCATCCAGGAGCA | 31 |
| EYA1 R | GGGCCACTGGGGGATTCACT | 32 |
| FOXI3 F | TCCCCTTCTACCAGCGCAGC | 33 |
| FOXI3 R | TCCCAGCAGCCACTGTGGAG | 34 |
| MSX1 F | AGTGTCCCCTTCGCTCCTGC | 35 |
| MSX1 R | GCTTGGCGGCCATCTTCAGC | 36 |
| MSX2 F | CCGCCTCGGTCAAGTCGGAA | 37 |
| MSX2 R | GCGAGGAGCTGGGATGTGGT | 38 |
| SIX4 F | CCAGCCCCTTTTCCCCTGGA | 39 |
| SIX4 R | GGGCAGCTGCAGTGGAGAGA | 40 |
| FOXD3 F | AGCACGGCGCAGTCGTTTCT | 41 |

TABLE 7-continued

Primers used for RT-PCR on human cells.

| GENE NAME | SEQUENCE | SEQ ID NO. |
|---|---|---|
| FOXD3 R | TTGGGGGCTCAGGGGAAAGG | 42 |
| PAX5 F | GTGACGCAGGTGTCCTCGGT | 43 |
| PAX5 R | TCTCCCCGCATCTGCTTCCG | 44 |
| HEY1 F | CGCCGACGAGACCGGATCAA | 45 |
| HEY1 R | GTTCTGGGGCAGCAACAGCG | 46 |
| HEY2 F | ACCTGAGCTCCGTGGAAGGC | 47 |
| HEY2 R | GCTGCTGCGTTTGGGGGAAG | 48 |
| NKX5.1 F | CGACCTGGCTTTCCCTCGCT | 49 |
| NKX5.1 R | CTTGTGATCGGGGTCGGCCT | 50 |
| TBX1 F | TCACCGCGGTCACTGCCTAC | 51 |
| TBX1 R | GGGAGCCCCAGGTTCACACA | 52 |
| TBX2 F | CGACTTCCCCATGTCCGCCT | 53 |
| TBX2 R | ACATCCGCCTCCCGGACTTG | 54 |
| HES6 F | CGTGTGGGCCGTGAGGATGA | 55 |
| HES6 R | TCCGTCCAGGGGCTCTAGGT | 56 |
| DACH1 F | CAACCCCGTCCCCAGTGGAA | 57 |
| DACH1 R | TCACTCCTGGCTGGATGGCG | 58 |
| OTX1 F | CCACCCGTTGAGCCAGTCCT | 59 |
| OTX1 R | CGGCAGTGCAGGCAATGGAC | 60 |
| GATA3 F | GTCCAGCACAGGCAGGGAGT | 61 |
| GATA3 R | ATGTGTCTGGAGAGGGCGGC | 62 |
| GATA6 F | CGACAGCCCTCCATACGGCA | 63 |
| GATA6 R | CCAGCAGGTCTGCACTGGGA | 64 |
| ACTIVINR1 F | AAGCCGTGGAGTGCTGCCAA | 65 |
| ACTIVINR1 R | GCCCCTCCACACCTCACCAT | 66 |
| DLX3 F | CTGGACACACACCCCTGCCT | 67 |
| DLX3 R | GTTGGTGGGGTCGTCCAGGT | 68 |
| SOX3 F | GGGAGGCGCAGGCAAGAGTA | 69 |
| SOX3 R | CTTGGGGTTCTCCAGGGCCA | 70 |
| NOTCH1 F | AGACACTGCCTGGGCTGACC | 71 |
| NOTCH1 R | GCGGGGACAGGACCAAAGGA | 72 |
| DELTA1 F | CGAGTGTGACCCCAGCCCTT | 73 |
| DELTA1 R | CCATTGTGGCAGGGTGCGTG | 74 |
| HES1 F | GCTGCTACCCCAGCCAGTGT | 75 |
| HES1 R | CGTGGACAGGAAGCGGGTCA | 76 |
| H-OCT4 F | AGTGAGAGGCAACCTGGAGA | 77 |
| H-OCT4 R | GTGAAGTGAGGGCTCCCATA | 78 |

TABLE 7-continued

Primers used for RT-PCR on human cells.

| GENE NAME | SEQUENCE | SEQ ID NO. |
|---|---|---|
| H-REX1 F | AGAATTCGCTTGAGTATTCTGA | 79 |
| H-REX1 R | GGCTTTCAGGTTATTTGACTGA | 80 |
| H-GAPDH F | GTACTCAGCGCCAGCATCG | 81 |
| H-GAPDH R | AGCCACATCGCTCAGACACC | 82 |
| H-PAX6 F | TGAGGGCTGTGTGCTGAGGG | 83 |
| H-PAX6 R | CCGCTCCCACGTCACTCCTT | 84 |
| H-BRACHURY F | TCACCCTACCCCAGCCCCTA | 85 |
| H-BRACHURY R | GCTGGCATTGTGGCTCACGG | 86 |
| H-KLK1 F | GGAACCCGAAGTGGGGAGCA | 87 |
| H-KLK1 R | GCCACCTTCCAGGTGTCCGA | 88 |
| H-SERPINA1 F | AGACCCTTTGAAGTCAAGGACACCG | 89 |
| H-SERPINA1 R | CATTGCTGAAGACCTTAGTGATGC | 90 |
| H-KERATIN 5 F | TCAAGGATGCCAGGAACAAG | 91 |
| H-KERATIN 5 R | GCTTGCACTGAAGCCAGAG | 92 |
| H-HS KERATIN F | TCCTGCCGCTGTGGAGTCTG | 93 |
| H-HS KERATIN R | CGGAGTTGGCTGGCAGGAGT | 94 |
| H-HCG F | GTCAACACCACCATCTGTGC | 95 |
| H-HCG R | GGCCTTTGAGGAAGAGGAGT | 96 |
| H-ECADHERIN F | TTCCCTCGACACCCGATTCAAAGT | 97 |
| H-ECADHERIN R | AGCTGTTGCTGTTGTGCTTAACCC | 98 |
| H-KERATIN14 F | CTCCGCTGCGAGATGGAGCA | 99 |
| H-KERATIN14 R | AAGGACCTGCTCGTGGGTGG | 100 |
| H-SOX10 F | GCCTGTTCTCCTGGGGCTTTGCTGC | 101 |
| H-SOX10 R | CATCCACCTCACAGATCGCCTACAC | 102 |
| H-DLX5 F | CTCCCAGTCTCCTCCTCGCC | 103 |
| H-DLX5 R | TGCGGACGTCTGGAACGGAG | 104 |
| H-NESTIN F | GCGTTCCCTGCTGAGACCCT | 105 |
| H-NESTIN R | TGAGGCCCAGGGGCATCTTC | 106 |
| H-PAX2 F | TGGGGGCGTCAGGTCTTTCC | 107 |
| H-PAX2 R | CAGGCGAAGGACTGGCAGGA | 108 |
| H-BMP7 F | AGGGCAAGCACAACTCGGCA | 109 |
| H-BMP7 R | CATGTCGGCGTCGGTGAGGA | 110 |
| H-JAG1 F | CGGGAGGTGGAAGAGGAGGG | 111 |
| H-JAG1 R | GCCGCGTCCCGGCTCTAATA | 112 |
| H-OTX2 F | GCAGAGGTCCTATCCCATGA | 113 |
| H-OTX2 R | CTGGGTGGAAAGAGAAGCTG | 114 |
| H-ATOH1 F | ACGCTCTGCACTTCTCGACT | 115 |
| H-ATOH1 R | ACTTGCCTCATCCGAGTCAC | 116 |
| H-MYO7A F | CAGCCACTGCTCTACCATGA | 117 |
| H-MYO7A R | GCAGCTCCCTCTTGTACGTC | 118 |

On day 24, the media is replaced with 10% KSR Differentiation Media comprising bFGF (5-25 ng/ml) and BMP4 (1-20 ng/ml). No other factors are typically added.

On day 27 and 30, the media is replaced with 5% KSR Differentiation Media without any additional factors. The cells are cultured at 37° C. in a humidified atmosphere of 5% $CO^2$ for 72 h without changing media.

On day 33, the media is replaced with freshly prepared 0% KSR Differentiation Media.

Figure 35:
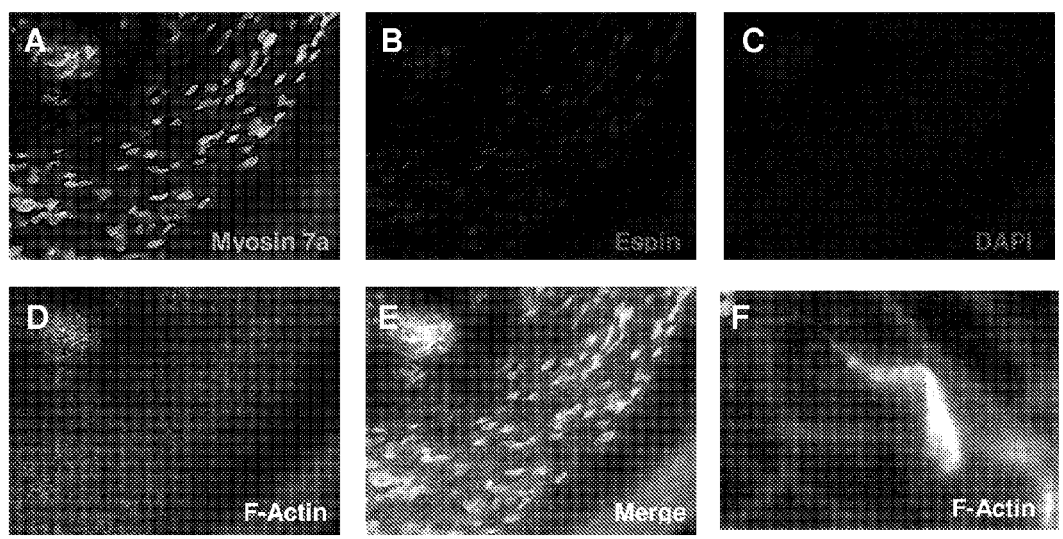
FIG. 35. Epithelial patch of nascent human ES cell-derived hair cell-like cells that express (A) Myosin 7a; (B) Espin; (C) DAPI; and (D) F-Actin. (E) Merged staining. (F) Higher magnification of a human hair cell like cell stained with F-actin; a hair bundle-like protrusion is visible.
Figure 36:
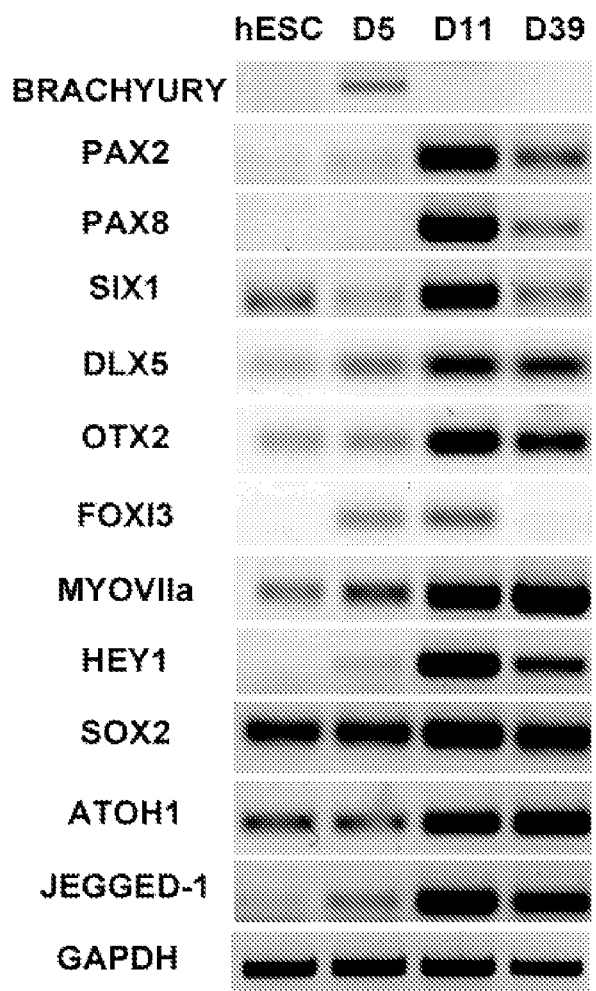
FIG. 36. Characterization of cells at different time points of the protocol by RT-PCR.
Figure 37:
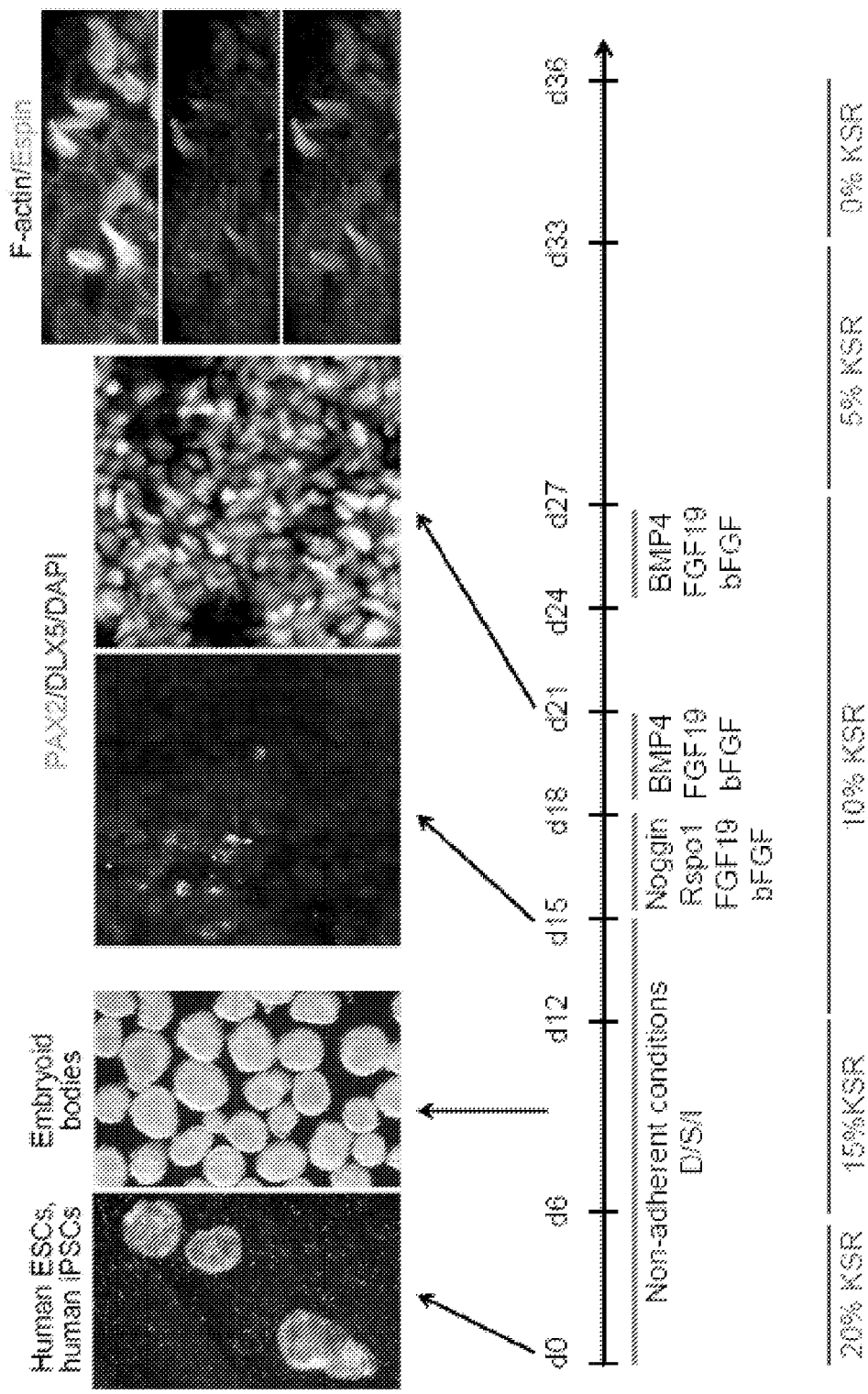
FIG. 37. Otic guidance protocol for human ESCs and iPSCs. After inhibition of mesoderm and endoderm formation in medium supplemented with Dkk1, SIS3, and IGF-1 (D/S/I), the cells are subjected to stabilization of preplacodal state and simultaneous induction of otic fate with FGFs. A later step of incubation with BMP4 and bFGF may be performed to promote the formation of hair bundles. Knockout serum replacement (KSR) may be reduced throughout the culture period from 20% to zero. 3-dimensional inner ear sensory epithelia can be identified after 36 days in culture (d36).
Figure 38:
FIG. 38. Human ES cell-derived inner ear sensory epithelial patches display hair bundle-like protrusions. (A) Shows that the protrusions are F-actin-rich by visualization with TRITC-conjugated phalloidin. (B) Shows that the hair budges-like structures co-express the stereociliary protein espin. (C) is a merge. The scale bar approximately indicates 5 μm.
Figure 39:
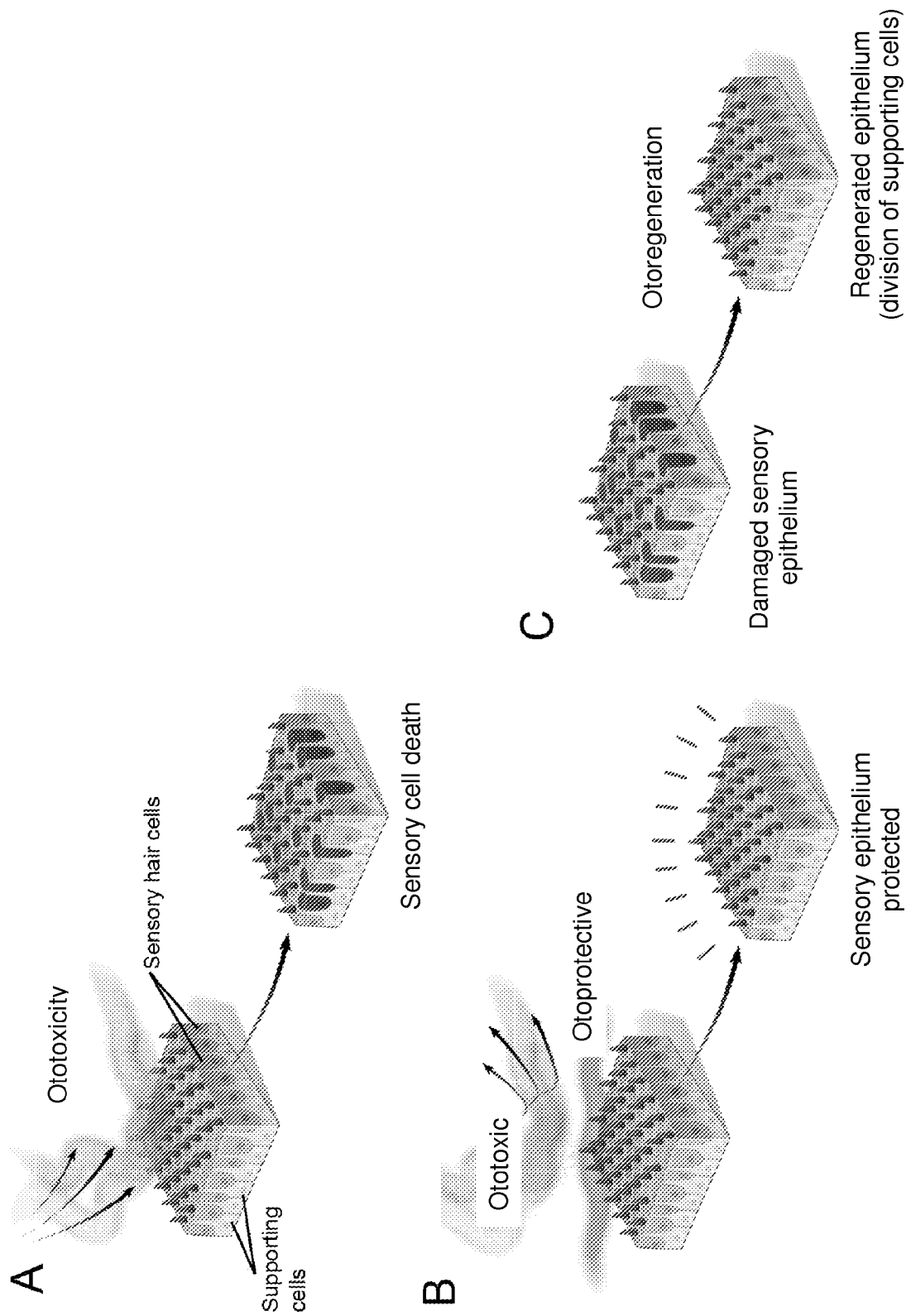
FIG. 39. Schematic drawings of examples of screens that may be performed using cells prepared by the subject methods. (A) ototoxicity screens, (B) otoprotection screen, (C) otoregeneration screens.

On day 36, the cells can be stained with hair and supporting cell markers (see FIGS. 35 and 36) and used for further experiments.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of the present invention is embodied by the appended claims.

That which is claimed is:

1. A method of screening a candidate agent for an effect on inner ear cells, the method comprising:
   a. culturing pluripotent stem cells in the presence of an ectoderm rostralizinq factor and at least one factor that suppresses the formation of endoderm and mesoderm thereby producing a population comprising preplacodal ectodermal cells;
   b. culturing the population comprising preplacodal ectodermal cells under adherent conditions in the presence of fibroblast growth factor (FGF) thereby producing a population comprising otic progenitor cells;
   c. culturing the population comprising otic progenitor cells under adherent conditions thereby producing inner ear cells;
   d. contacting the inner ear cells with a candidate agent; and
   e. comparing the viability, function and/or regenerative response of the inner ear cells contacted with the candidate agent to the viability, function and/or regenerative response of inner ear cells that were not contacted with the candidate agent;
   wherein a difference in viability, function and/or regenerative response of inner ear cells contacted with the candidate agent compared to inner ear cells that were not contacted with the candidate agent indicates that the candidate agent has an effect on inner ear cells.

2. The method according to claim 1, wherein the effect is toxicity,
   wherein the comparing comprises comparing the viability and/or function of the inner ear cells contacted with candidate agent to the viability and/or function of inner ear cells that were not contacted with the candidate agent, and
   wherein a reduction in viability and/or function of inner ear cells contacted with the candidate agent compared to inner ear cells that were not contacted with the candidate agent indicates that the candidate agent is toxic to inner ear cells.

3. The method according to claim 1, wherein the effect is protection from the toxicity of a toxic agent,
   wherein the method comprises contacting the inner ear cells with a toxic agent prior to contacting the inner ear cells with the candidate agent,
   wherein the comparing comprises comparing the viability and/or function of the inner ear cells contacted with the toxic agent and candidate agent to the viability and/or function of inner ear cells that were contacted with the toxic agent and were not contacted with the candidate agent,
   wherein an enhanced viability and/or function of inner ear cells contacted with the candidate agent compared to inner ear cells that were not contacted with the candidate agent indicates that the candidate agent protects inner ear cells from the toxicity of the toxic agent.

4. The method according to claim 1, wherein the effect is promoting otoregeneration,
   wherein the comparing comprises comparing the regenerative response of the inner ear cells contacted with candidate agent to the regenerative response of inner ear cells that were not contacted with the candidate agent, and
   wherein an enhancement in the regeneration of inner ear cells contacted with the candidate agent compared to inner ear cells that were not contacted with the candidate agent indicates that the candidate agent promotes otoregeneration.

5. The method according to claim 1, wherein the at least one factor that suppresses the formation of endodermal and mesoderm is selected from an inhibitor of Wnt signaling and an inhibitor of TGFB signaling.

6. The method according to claim 1, wherein the at least one factor that suppresses the formation of endodermal and mesoderm includes at least one inhibitor of Wnt signaling and at least one inhibitor of TGFB signaling.

7. The method according to claim 1, wherein the at least one ectoderm rostralizing factor is a factor that activates IGF signaling.

8. The method according to claim 1, wherein the at least one ectoderm rostralizing factor is IGF or insulin.

9. The method according to claim 1,
   wherein step b) comprises:
      culturing the population comprising preplacodal ectodermal cells under adherent conditions in the presence of at least one FGF and at least one additional factor that promotes the induction of otic progenitor cells thereby producing the population comprising otic progenitor cells; and wherein step c) comprises:
      culturing the population comprising otic progenitor cells under adherent conditions in the presence of FGF and at least one additional factor that promotes the stabilization of otic progenitor cells.

10. The method according to claim 9, wherein the at least one additional factor that promotes the induction of otic progenitor cells is selected from the group consisting of an inhibitor of BMP signaling, an activator of Wnt signaling, and FGF19.

11. The method according to claim 9, wherein the at least one additional factor that promotes the stabilization of otic progenitor cells is selected from the group consisting of an activator of BMP signaling and FGF19.

12. The method according to claim 1, wherein the method further comprises mechanically enriching the population comprising preplacodal ectodermal cells prior to step b).

13. The method according to claim 1, wherein the method further comprises mechanically enriching the population comprising otic progenitor cells for otic progenitor cells prior to step (c).

14. The method according to claim 1, wherein the otic progenitor cells are expanded prior to step (c).

15. The method according to claim 1, wherein the pluripotent stem cells are human stem cells, and culturing the otic progenitor cells further comprises culturing in the absence of feeder cells.

16. The method according to claim 1, wherein the pluripotent stem cells are rodent stem cells, and culturing the otic progenitor cells further comprises culturing in the presence of feeder cells.

17. The method according to claim 1, wherein the pluripotent stem cells are induced pluripotent stem cells (iPSCs).

18. The method according to claim 17, wherein the iPSCs are human iPSCs.

19. The method according to claim 17, wherein the iPSCs are rodent iPSCs.

* * * * *

UNITED STATES PATENT AND TRADEMARK OFFICE
CERTIFICATE OF CORRECTION

| | | |
|---|---|---|
| PATENT NO. | : 9,157,064 B2 | Page 1 of 1 |
| APPLICATION NO. | : 13/980837 | |
| DATED | : October 13, 2015 | |
| INVENTOR(S) | : Heller et al. | |

It is certified that error appears in the above-identified patent and that said Letters Patent is hereby corrected as shown below:

In the specification

Please replace Column 1, lines 14-21 with:

--GOVERNMENT RIGHTS

This invention was made with Government support under contracts DC006167 and DC010363 awarded by the National Institutes of Health. The Government has certain rights in the invention.--

Signed and Sealed this
Seventh Day of June, 2016

Michelle K. Lee
*Director of the United States Patent and Trademark Office*